(12) United States Patent
Slamon et al.

(10) Patent No.: US 6,929,910 B2
(45) Date of Patent: Aug. 16, 2005

(54) DIAGNOSTIC AND THERAPEUTIC METHODS USING THE H37 TUMOR SUPPRESSOR GENE

(75) Inventors: Dennis J. Slamon, Woodland Hills, CA (US); Juliana J. Oh, Rowland Heights, CA (US)

(73) Assignee: The Regents of the University of California, Oakland, CA (US)

( * ) Notice: Subject to any disclaimer, the term of this patent is extended or adjusted under 35 U.S.C. 154(b) by 409 days.

(21) Appl. No.: 09/957,763

(22) Filed: Sep. 21, 2001

(65) Prior Publication Data

US 2003/0225008 A1 Dec. 4, 2003

Related U.S. Application Data

(63) Continuation-in-part of application No. 09/553,242, filed on Apr. 19, 2000, now abandoned.

(51) Int. Cl.$^7$ .......................... C12Q 1/68; G01N 33/53; C07H 21/02; C07H 21/04
(52) U.S. Cl. .......................... 435/6; 435/7.1; 536/23.1; 536/23.5; 536/24.31
(58) Field of Search .................... 435/6, 7.1; 536/23.1, 536/23.5, 24.31; 530/350; 424/130.1

(56) References Cited

U.S. PATENT DOCUMENTS

| | | |
|---|---|---|
| 5,559,011 A | 9/1996 | Kapoor et al. |
| 6,129,914 A | 10/2000 | Weiner et al. |

OTHER PUBLICATIONS

J. Oh et al, "Identification of Differentially Expressed Genes Associated with HER-2/neu Overexpression in Human Breast Cancer Cells," Nucleic Acids Research, 1999, 27(20): 4008–4017.
H. Edamatsu et al., "LUCA15, A Putative Tumour Suppressor Gene Encoding an RNA–Binding Nuclear Protein, Is Down–Regulated in Ras–Transformed Rat–1 Cells," Genes to Cells, Oct. 2000, 5(10): 849–858, abstract only.
M.C. Daly et al. (1993) "A homozygous deletion on chromosome 3 in a small cell lung cancer cell line correlates with a region of tumor suppressor activity", Oncogene 8:1721–1729.
H.A. Drabkin et al. (1999) "DEF–3(g16/NY–LU–12), an RNA binding protein from the 3p21.3 homozygous deletion region in SCLC", Oncogene 18:2589–2597.

A.O. Gure et al. (1998) "Human Lung Cancer Antigens Recognized by Autologous Antibodies: Definition of a Novel cDNA Derived from the Tumor Suppressor Gene Locus on Chromosome 3p21.3", Cancer Research pp. 1034–1041.
A. McNeill Killary et al. (1992) "Definition of a tumor suppressor locus within human chromosome 3p21–p22", Proc. Natl. Acad. Sci. USA 89:10877–10881.
K. Kok et al. (1987) "Deletion of a DNA sequence at the chromosomal region 3p21 in all major types of lung cancer", Nature 330(10):578–581.
M.J. Scanlan et al. (1999) "Antigens Recognized by Autologous Antibody in Patients with Renal–Cell Carcinoma", Int. J. Cancer 84:456–464.
T. Timmer et al. (1999) "A comparison of genomic structures and expression patterns of two closely related flanking genes in a critical lung cancer region at 3p21.3", European Journal of Human Genetics 7:478–486.
T. Timmer et al. (1999) "An Evolutionary Rearrangement of the Xp11.3–11.23 Region in 3p21.3, a Region Frequently Deleted in a Variety of Cancers", Genomics 60–238–240.
M.C. Todd et al. (1996) "An 80 Kb P1 clone from chromosome 3p21.3 suppresses tumor growth in vivo", Oncogene 13:2387–2396.
M–H. Wei et al. (1996) "Construction of a 600–Kilobase Cosmid Clone Contig and Generation of a Transcriptional Map Surrounding the Lung Cancer Tumor Suppressor Gene (TSG) Locus on Human Chromosome 3p21.3: Progress toward the Isolation of a Lung Cancer TSG$^1$", Cancer Research 56:1487–1492.
N.L. Chitkara et al., "Effect of Guinea–Pig–Organ Extract on Growth of Mycobacterium H37 RV,"Indian J. Path Microbiol, Oct. 1976, 19(4):211–221.
G. Contreas et al., "Novel Islet, Duct, and Acinar Cell Markers Defined by Monoclonal Autoantibodies from Prediabetic BB Rats," Pancreas, Sep. 1990, 5(5):540–547.
J.J. Oh et al., "A Candidate Tumor Suppressor Gene, H37, from the Human Lung Cancer Tumor Suppressor Locus 3p21.3$^1$," Cancer Res Jun. 1, 2002, 62:3207–3213.

*Primary Examiner*—Joseph Woitach
(74) *Attorney, Agent, or Firm*—Gates & Cooper LLP

(57) ABSTRACT

The present invention relates to the identification of the H37 tumor suppressor gene and methods of diagnosing and treating a disease or disorder characterized by abnormal cellular proliferation, such as a tumor or cancer. Diagnosis is accomplished examining or monitoring cells for perturbations in H37 expression or function. Treatment is accomplished by inserting a host cell compatible H37 expression vector or an effective amount of H37 protein into a cell or cells in need of treatment.

9 Claims, 23 Drawing Sheets

```
GGCACGAGCCGCCGAACCTTGTTGGAGGTTCTGGGGCGCAGAACCGCTACTGCTGCTTCGGTCTCTCC
TTGGGAAAAAATAAAATTTGAACCTTTTGGAGCTGTGTGCTAAATCTTCAGTGGGACAATGGGTTCAG
ACAAAAGAGTGAGTAGAACAGAGCGTAGTGGAAGATACGGTTCCATCATAGACAGGGATGACCGTGAT
GAGCGTGAATCCCGAAGCAGGCGGAGGGACTCAGATTACAAAAGATCTAGTGATGATCGGAGGGGTGA
TAGATATGATGACTACCGAGACTATGACAGTCCAGAGAGAGAGCGTGAAAGAAGGAACAGTGACCGAT
CCGAAGATGGCTACCATTCAGATGGTGACTATGGTGAGCACGACTATAGGCATGACATCAGTGACGAG
AGGGAGAGCAAGACCATCATGCTGCGCGGCCTTCCCATCACCATCACAGAGAGCGATATTCGAGAAAT
GATGGAGTCCTTCGAAGGCCCTCAGCCTGCGGATGTGAGGCTGATGAAGAGGAAAACAGGTGTAAGCC
GTGGTTTCGCCTTCGTGGAGTTTTATCACTTGCAAGATGCTACCAGCTGGATGGAAGCCAATCAGAAA
AAGTTGGTGATTCAAGGAAAGCACATTGCAATGCATTATAGCAATCCCAGACCTAAGTTTGAAGATTG
GCTTTGTAACAAGTGCTGCCTTAACAATTTCAGGAAAAGACTAAAATGCTTCCGATGTGGAGCAGACA
AGTTTGACTCTGAACAGGAAGTGCCTCCTGGAACCACAGAGTCGGTTCAGTCTGTGGATTACTACTGT
GATACGATCATTCTTCGGAACATAGCTCCGCACACTGTGGTGGATTCCATCATGACAGCACTGTCTCC
TTACGCGTCTTTAGCTGTCAATAACATCCGCCTCATAAAAGACAAACAGACCCAGCAGAACAGAGGCT
TCGCATTTGTGCAGCTGTCCTCTGCAATGGATGCTTCTCAGCTGCTTCAGATATTACAGAGTCTCCAT
CCTCCTTTGAAAATTGATGGCAAAACTATTGGGGTTGATTTTGCAAAAAGTGCCAGAAAAGACTTGGT
CCTCTCAGATGGTAACCGCGTCAGCGCCTTCTCTGTAGCTAGTACGGCTATTGCTGCTGCTCAGTGGT
CATCCACCCAGTCTCAAAGTGGTGAAGGAGGCAGTGTTGACTACAGTTATCTGCAACCAGGTCAAGAT
GGCTATGCCCAATATGCTCAGTATTCACAGGATTATCAGCAGTTTTATCAACAACAAGCTGGAGGATT
GAATCTGATGCATCATCTGCATCAGGCACAGCAGTGACCACCACCTCAGCGGCTGTAGTGTCCCAGA
GTCCTCAGCTGTATAATCAAACCTCCAATCCACCTGGCTCTCCGACTGAGGAAGCACAGCCTAGCACT
AGCACAAGTACACAGGCCCCAGCCGCTTCCCCTACTGGTGTAGTTCCTGGTACCAAATATGCAGTACC
TGACACGTCCACTTACCAGTATGATGAATCTTCAGGATATTACTATGATCCGACAACAGGGCTCTATT
ATGACCCCAACTCGCAATACTACTATAATTCCTTGACCCAGCAGTACCTTTACTGGGATGGGGAAAAA
GAGACCTACGTGCCAGCTGCAGAGTCTAGCTCCCACCAGCAGTCGGGCCTGCCTCCTGCAAAAGAGGG
GAAAGAGAAGAAGGAGAAACCCAAGAGCAAAACAGCCCAGCAGATTGCCAAAGACATGGAACGCTGGG
CTAAGAGTTTGAATAAGCAGAAAGAAAACTTTAAAAATAGCTTTCAGCCTGTCAATTCCTTGAGGGAA
GAAGAAAGGAGAGAATCTGCTGCAGCAGACGCTGGCTTTGCTCTCTTTGAGAAGAAGGGAGCCTTAGC
TGAAAGGCAGCAGCTCATCCCAGAATTGGTGCGAAATGGAGATGAGGAGAATCCCCTCAAAAGGGGTC
TGGTTGCTGCTTACAGTGGTGACAGTGACAATGAGGAGGAGCTGGTGGAGAGACTTGAGAGTGAGGAA
GAGAAGCTAGCTGACTGGAAGAAGATGGCCTGTCTGCTCTGCCGGCGCCAGTTCCCGAACAAAGATGC
CCTAGTCAGGCACCAGCAACTCTCAGACCTTCACAAGCAAAACATGGACATCTACCGACGATCCAGGC
TGAGCGAGCAGGAGCTGGAAGCCTTGGAGCTAAGGGAGAGAGAGATGAAATACCGAGACCGAGCTGCA
GAAAGACGGGAGAAGTACGGCATTCCAGAACCTCCAGAGCCCAAGCGCAAGAAGCAGTTTGATGCCGG
CACTGTGAATTACGAGCAACCCACCAAAGATGGCATTGACCACAGTAACATTGGCAACAAGATGCTGC
AGGCCATGGGCTGGCGGGAAGGCTCTGGCTTGGGACGAAAGTGTCAAGGCATTACGGCTCCCATTGAG
GCTCAAGTTCGGCTAAAGGGAGCTGGCCTAGGAGCCAAAGGCAGCGCATATGGTTTGTCGGGCGCCGA
TTCCTACAAAGATGCTGTCCGGAAAGCCATGTTTGCCCGGTTCACTGAGATGGAGTGAGAGAGAGAGA
GAGAGAGAGATGACAAGGAGCACAAGAAGTGGTCCATCTCCCGAATTCGCTGTTACCGCCTGTCTCTT
TAAGGGCATGCCTTGTGCTGTTAATAGATCTTAGGGTGAACCACTTCATTCTGCAGGGTTCTCCCTCC
CACCTTAAAGAAGTTCCCCTTATGTGGGTTGCCTGGTGAATGGCCTTCCTTCCCGCCAGAGGGCTTGT
GAACAGACCGGAGAGGACAGTGGATTGTTTATACTCCAGTGTACATAGTGTAATGTAGCGTGTTTACA
TGTGTAGCCTATGTTGTGGTCCATCAGCCCCTCACATTCCTAGGGGTTTGAGATGCTGTAGGTGGTAT
GTGACACCAAAGCCACCTCTGTCATTTGTTGTGATGTCTTTTCTTGGCAAAAGCCTTGTGTATATTTG
TATATTACACATTTGTACAGAATTTTGGAAGATTTTCAGTCTAGTTGCCAAATCTGGCTCCTTTACAA
AAGAAATACCTTGAGAAAAAAAAAAAAAAAAAA
```

FIG. 1A

```
MGSDKRVSRTERSGRYGSIIDRDDRDERESRSRRRDSDYKRSSDDRRGDRY
DDYRDYDSPERERERRNSDRSEDGYHSDGDYGEHDYRHDISDERESKTIML
RGLPITITESDIREMMESFEGPQPADVRLMKRKTGVSRGFAFVEFYHLQDA
TSWMEANQKKLVIQGKHIAMHYSNPRPKFEDWLCNKCCLNNFRKRLKCFRC
GADKFDSEQEVPPGTTESVQSVDYYCDTIILRNIAPHTVVDSIMTALSPYA
SLAVNNIRLIKDKQTQQNRGFAFVQLSSAMDASQLLQILQSLHPPLKIDGK
TIGVDFAKSARKDLVLSDGNRVSAFSVASTAIAAAQWSSTQSQSGEGGSVD
YSYLQPGQDGYAQYAQYSQDYQQFYQQQAGGLESDASSASGTAVTTTSAAV
VSQSPQLYNQTSNPPGSPTEEAQPSTSTSTQAPAASPTGVVPGTKYAVPDT
STYQYDESSGYYYDPTTGLYYDPNSQYYYNSLTQQYLYWDGEKETYVPAAE
SSSHQQSGLPPAKEGKEKKEKPKSKTAQQIAKDMERWAKSLNKQKENFKNS
FQPVNSLREEERRESAAADAGFALFEKKGALAERQQLIPELVRNGDEENPL
KRGLVAAYSGDSDNEEELVERLESEEEKLADWKKMACLLCRRQFPNKDALV
RHQQLSDLHKQNMDIYRRSRLSEQELEALELREREMKYRDRAAERREKYGI
PEPPEPKRKKQFDAGTVNYEQPTKDGIDHSNIGNKMLQAMGWREGSGLGRK
CQGITAPIEAQVRLKGAGLGAKGSAYGLSGADSYKDAVRKAMFARFTEME
```

FIG. 1B

*In vitro* translation of the H37 cDNA

H37 mRNA transcript level achieved in transfection

Growth Comparison of NCI H740 Cells (view of entire flasks)

H37 transfectant vector control

H37 transfectant vector control

Growth Comparison of NCI H740 Cells
(close-up view of colonies)

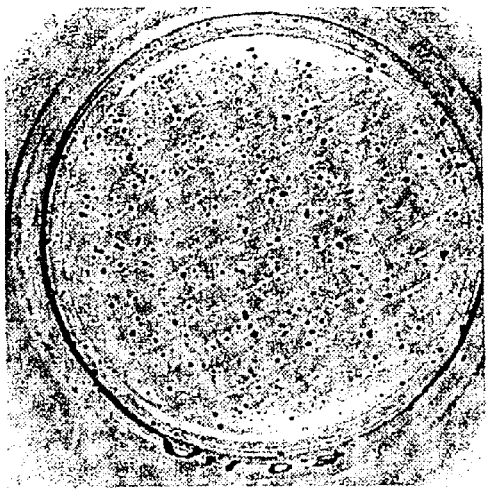
FIG. 11C H37.clone C
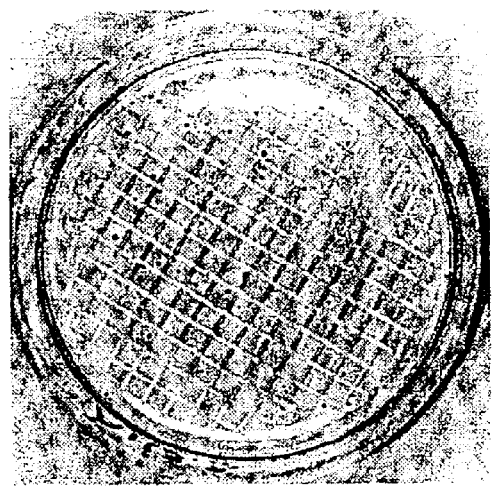
A9 Soft Agar Colony Assay
FIG. 11B H37.clone A
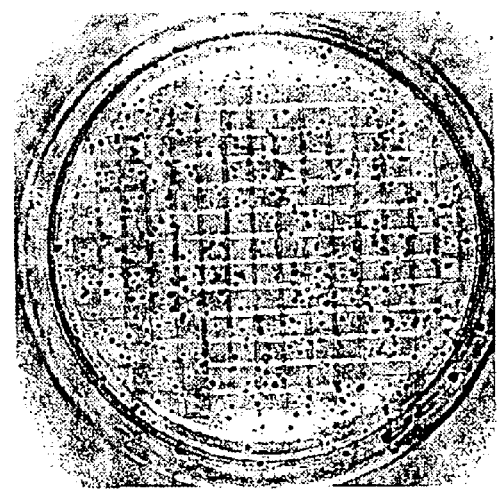
FIG. 11A vector control

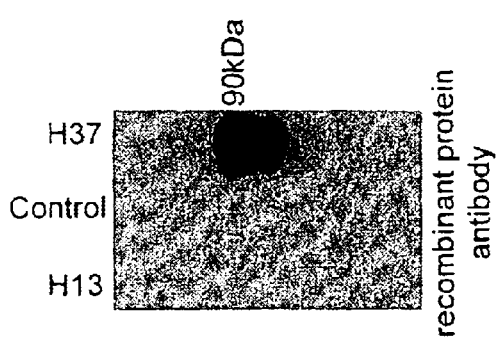

FIG. 15B

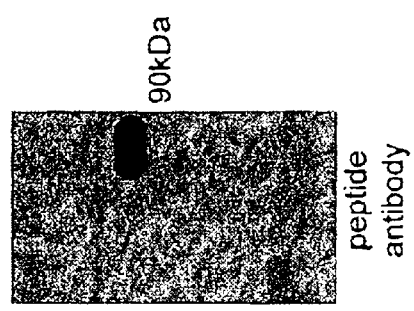

FIG. 15C

Generation of polyclonal antibodies recognizing H37 protein
(both peptide and recombinant protein antibodies)

over-all scheme recombinant protein subclone the H37 cDNA (a.a. #408~815) into the maltose binding protein fusion vector → expression of fusion protein in E. coli. → protein purification via amylose resin column peptide synthesis of 17-mer peptide (a.a. #27~43)

→ injection into rabbits & serum collection

FIG. 15A

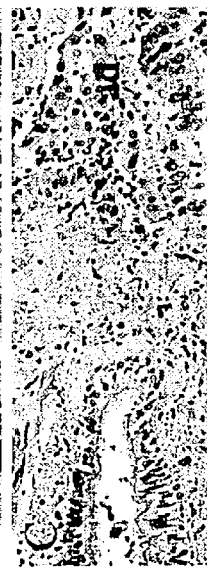
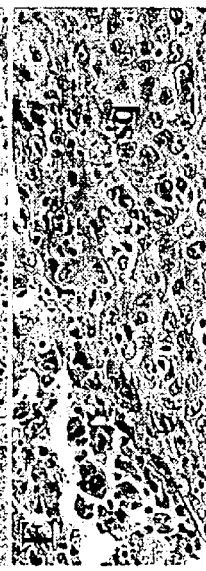
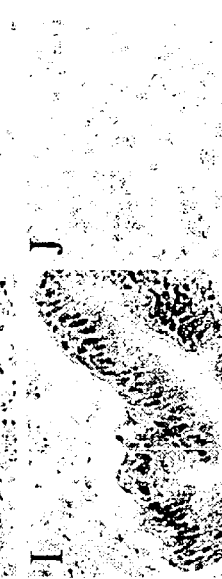
FIG. 18A  FIG. 18B  FIG. 18C  FIG. 18D  FIG. 18E  FIG. 18F  FIG. 18G  FIG. 18H  FIG. 18I  FIG. 18J

```
  1  MGSDKRVSRT  ERSGRYGSII  DRDRDRERES  RSRRRDSDYK  RSSDDRRGDR
 51  YDDYRDYDSP  ERERERRNSD  RSEDGYHSDG  DYGEHDYRHD  ISDERESKTI
101  MLRGLPITIT  ESDIREMMES  FEGPQPADVR  LMKRKTGVSR  GFAFVEFYHL
151  QDATSWMEAN  QKKLIQGKH  IAMHYSNPRP  KFEDWLCNKC  CLNNFRKRLK
201  CFRCGADKFD  SEQEVPPGTT  ESVQSVDYC   DTIILRNIAP  HTVVDSIMTA
251  LSPYASLAVN  NIRLIKDKQT  QQNRGFAFVQ  LSSAMDASQL  LQILQSLHPP
301  LKIDGKTIGV  DFAKSARKDL  VLSDGNRVSA  ESVASTAIAA  AQWSSTQSQS
351  GEGGSVDYSY  LQPGQDGYAQ  YAQYSQDYQQ  FYQQQAGGLE  SDASSASGTA
401  VTTTSAAVVS  QSPQLYNQTS  NPPGSPTEEA  QPSTSTSTQA  PAASPTGVVP
451  GTKYAVPDTS  TYQYDESSGY  YDPTTGLYY   DPNSQYYYNS  LTQQYLYWDG
501  EKETYVPAAE  SSSHQQSGLP  PAKEGKEKKE  KPKSKTAQQI  AKDMERWAKS
551  LNKQKENFKN  SFQPVNSLRE  EERRESAAAD  AGFALFEKKG  ALAERQQLIP
601  ELVRNGDEEN  PLKRGLVAAY  SGDSDNEEEL  VERLESEEEK  LADWKKMACL
651  LCRROFPNKD  ALVRHQQLSD  LHKQNMDIYR  RSRLSEQELE  ALELREREMK
701  YRDRAAERRE  KYGIPEPPEP  KRKQFDAGT   VNYEQPTKDG  IDHSNIGNKM
751  LQAMGWREGS  GLGRKCQGIT  APIEAQVRLK  GAGLGAKGSA  YGLSGADSYK
801  DAVRKAMFAR  FTEME
```

FIG. 19A

```
H37     112  S  DIREMMES  FEEGPQPADV RLMKRKT-  GVSRGFAFVEF
5DEF-3  470  E  EILNAFRTP  DGMPVKNLQ  KEYNT-   GYDYGYVCVEF
6S1-1    66  A  EIRGQLQS   H-GV-QARE  VLMRNKS    SRGFAFVEF
7sxl    139  R  ELYALFRAI  -G-PINTCR  IMRDYKT   GYSFGYAFVDF H37     149  Y  HLQDATSW   MEANQKKL   VIQGKHIAMH  YSN
DEF-3   507  S  LLEDATIG   CMEANQGT   LMIHQDKEVTL EYVS
S1-1    103  S  HLQDATRW   MEANQHSL   NILGQKVSMH  YSD
sxl     176  T  SEMDSQRA   LFKVLNG-   ITVRNKRLK
```

FIG. 19B

DIAGNOSTIC AND THERAPEUTIC METHODS USING THE H37 TUMOR SUPPRESSOR GENE

This application is a continuation-in-part of U.S. patent application Ser. No. 09/553,242 filed Apr. 19, 2000 now abandoned, the entire contents of which are incorporated herein by reference.

This invention was made in part with United States government support under Grant No. DAMD17-94J4234, awarded by the Department of Defense, and Grant No. CA32737, awarded by National Institutes of Health. The Government has certain rights in the invention.

FIELD OF THE INVENTION

The invention described herein relates to diagnostic and therapeutic methods relating to the H37 tumor suppressor gene.

BACKGROUND OF THE INVENTION

Cancers are the second most prevalent cause of death in the United States, causing 450,000 deaths per year. One in three Americans will develop cancer, and one in five will die of cancer. While substantial progress has been made in identifying some of the likely environmental and hereditary causes of cancer, there is a need for substantial improvement in the diagnosis and therapy for cancer and related diseases and disorders.

A number of so-called cancer genes, i.e., genes that have been implicated in the etiology of cancer, have been identified in connection with hereditary forms of cancer and in a large number of well-studied tumor cells. Cancer genes are broadly classified into "oncogenes" which, when activated, promote tumorigenesis, and "tumor suppressor genes" which, when damaged, fail to suppress tumorigenesis. While these classifications provide a useful method for conceptualizing tumorigenesis, it is also possible that a particular gene may play differing roles depending upon the particular allelic form of that gene, its regulatory elements, the genetic background and the tissue environment in which it is operating.

Typically, tumor suppressor genes are genes that, in their wild-type alleles, express proteins that suppress abnormal cellular proliferation. When the gene coding for a tumor suppressor protein is mutated or deleted, the resulting mutant protein or the complete lack of tumor suppressor protein expression may fail to correctly regulate cellular proliferation, and abnormal cellular proliferation may take place, particularly if there are coincidental perturbations of other cellular regulatory mechanisms.

A number of well-studied human tumors and tumor cell lines have been shown to have missing or nonfunctional tumor suppressor genes. Examples of tumor suppression genes include, but are not limited to, the retinoblastoma susceptibility gene or RB gene, the p53 gene, the deleted in colon carcinoma (DCC) gene and the neutofibromatosis type 1 (NF-1) tumor suppressor gene. Loss of function or inactivation of tumor suppressor genes may play a central role in the initiation and/or progression of a significant number of human cancers.

While the identification tumor suppressor genes such as RB, p53, DCC and NF-1 facilitates efforts to diagnose and treat cancers, there is need for the identification of additional tumor suppressor genes in order to further improve diagnosis and therapy.

SUMMARY OF THE INVENTION

The present invention relates to a gene designated H37 which is identified herein as a novel tumor suppressor gene. This discovery allows one to employ a variety of methods for diagnosing and treating a disease or disorder characterized by abnormal cellular proliferation which involves H37.

As described herein, the status of H37 tumor suppressor gene may be evaluated in various cells by a variety of methods well known in the art. The evaluation of the status of the H37 gene provides information useful in diagnostic and prognostic protocols to assess the status of cells which may have disregulated growth. In preferred embodiments, the invention consists of methods for detecting evidence of disregulated growth in a cell such as a cell suspected of being cancerous. In these methods the status of the H37 gene is examined by any of a number of art accepted protocols such as a genomic Southerns to evaluate gross perturbations of genomic DNA, Northern and PCR analysis to evaluate the levels H37 mRNAs or immunological methods to examine H37 proteins. Such protocols are used to examine the level of H37 expression as well as the presence or absence of mutations within the H37 mRNA or proteins. In this context, these methods are used to compare the status of H37 in the test cell to the status of H37 gene in a corresponding normal cell or to a specific known standard, where an alteration in the status of H37 gene in the test cell relative to the normal cell provides evidence of disregulated growth within the test cell.

In specific illustrative embodiments of these methods, the status of the H37 gene is determined by a protocol selected from the group consisting of Southern hybridization, Northern hybridization, Western blotting, polymerase chain reaction and polynucleotide sequencing. In a preferred embodiment of this method, the status of H37 gene is examined by evaluating the level of mRNA transcripts within the cell. In another preferred embodiment, the cell analyzed in this method is from a biopsied tissue sample. In a specific embodiment of this method, the test cell is a human cell. In a more specific embodiment of this method, the test cell is suspected of being a tumor cell. In a highly preferred embodiment, the test cell suspected of being a tumor is selected from the group consisting of a lung cell, a breast cell, or a cervical cell.

A related embodiment of this method consists of evaluating a neoplasm in a patient by determining the quantity of functional H37 gene products in cells from neoplastic tissue of the patient, and comparing the quantity of functional H37 gene products in neoplastic cells to the quantity of functional H37 gene products in non-neoplastic cells of the patient, wherein a reduced quantity of functional H37 gene products in the neoplastic cells is indicative of an altered prognosis. In specific illustrative embodiments of these methods, the status of functional H37 gene products is evaluated by a protocol selected from the group consisting of Southern hybridization, Northern hybridization, Western blotting, polymerase chain reaction and polynucleotide sequencing. In another preferred embodiment, the neoplastic cell analyzed in this method is from a biopsied tissue sample. In a specific embodiment of this method, the neoplastic cell is a human cell. In a highly preferred embodiment, neoplastic cell is selected from the group consisting of a breast cell, a lung cell or a cervical cell.

Methods involving the H37 gene may be utilized in a therapeutic context in a manner analogous to therapeutic methods used with other tumor suppressor genes such as RB and p53. In an illustrative embodiment, the invention consists of a method of inhibiting proliferation of a cell comprising introducing into the cell an expression vector which comprises a polynucleotide that encodes a polypeptide having an amino acid sequence as shown in SEQ ID NO: 2;

wherein following the introduction, the polypeptide is expressed in the tumor cell so that proliferation of the cell is inhibited. In a specific embodiment, the polynucleotide of this method comprises the nucleotide sequence as shown in SEQ ID NO: 1 from nucleotide (ATG, nt #127–129) to and including (TGA, nt #2572–2574). Specific embodiments of H37 proteins comprise a polypeptide having the amino acid sequence of human H37 as shown in FIG. 1. Alternatively, embodiments of H37 proteins comprise variant polypeptides having alterations in the amino acid sequence of human H37 as shown in FIG. 1.

In a preferred embodiment of this method of inhibiting proliferation of a cell, the cell in which the H37 or H37 variant is introduced is a human tumor cell. In a highly preferred embodiment, the tumor cell is a lung carcinoma cell, a breast carcinoma cell or a cervical carcinoma cell. In yet another embodiment of this invention, the expression vector is a viral vector. In a specific embodiment of this invention, the viral vector is a cytomegalovirus vector, a retroviral vector, an adenoviral vector or a herpes viral vector. Alternatively, the expression vector is a plasmid. In yet another embodiment of this invention, the H37 polynucleotide is operably linked to a H37 gene enhancer or promoter, a retroviral long-terminal repeat, a cytomegalovirus promoter, a β-actin promoter, a glucocorticoid-inducible promoter, a SV40 early region promoter or a herpes simplex virus thymidine kinase promoter. In yet another embodiment of this invention, the expression vector is introduced into the cell by viral infection, liposome-mediated transfection, polybrene-mediated transfection or CaPO$_4$-mediated transfection. In one specific embodiment of this invention, the expression vector is introduced into the cell in vitro. In another specific embodiment of the invention, the expression vector is introduced into the cell in vivo.

BRIEF DESCRIPTION OF THE FIGURES

FIGS. 1A and 1B show the nucleotide (SEQ ID NO: 1) and amino acid (SEQ ID NO: 2) sequences of H37.

FIGS. 11A–11C are photographs showing the results of a soft agar colony assay of A9 cells transfected with H37 as compared to vector control cells.

FIG. 15A is a schematic showing the generation of antibodies to H37.

FIGS. 15B and C show a Western blot on in vitro translated H37 using antibodies generated with both recombinant H37 protein as well as H37 peptide (control=64 Kd luciferase; in vitro translation reaction control, H13=30 Kd "unrelated" gene product).

FIGS. 18A–18J show an immunohistochemical analysis of H37 in normal and cancer cells of the three different subtypes of NSCLC. FIGS A and B show H&E and immunostaining of normal bronchial epithelia showing nuclear staining of H37 protein. FIGS C and D show an example of adenocarcinoma (ad), H&E (C) and inmunostaining (D) of corresponding area showing reduced H37 protein in the tumor cells compared with adjacent normal epithelia. FIGS E, F, and G show an example of squamous cell carcinoma (sq), comparing immunostaining of H37 in normal epithelia (F) vs. reduced staining of the protein in tumor cells (G), both taken from the same slide. (E), H&E staining of the tumor area shown in G. FIGS H, I, and J show an example of large cell undifferentiated carcinoma (ud), comparing immunostaining of H37 in normal epithelia (I) vs. reduced staining of the protein in tumor cells Q), both taken from the same slide. (H), H&E staining of the tumor area shown in J.

FIGS. 19A–19C show that the H37 protein contains functional motifs which include two RNA binding domains, two zinc finger motifs and a bipartite nuclear localization signal (FIGS. 19A and 19B) and has different transcripts representing alternative splice variants (FIG. 19C). Homology studies demonstrate that H37 is related to Drosophila sex-lethal (SEQ ID NO: 7) (Bell et al., Cell 55, 1037–46 (1988)), mouse S1-1 (SEQ ID NO: 6) (Inoue et al., N.A.R. 24, 2990–7 (1996), and the human DEF-3 proteins (SEQ ID NO: 5) (Drabkin et al., Oncogene 18, 2589–97 (1999) sharing RNA recognition motif domains (FIG. 19B). H37 is expressed predominantly in heart, skeletal muscle, kidney and placental tissues (FIG. 19C). Two different transcripts representing alternative splice variants of 3.1 kb and 6.5 kb were detected in cells expressing the gene (FIG. 19C).

DETAILED DESCRIPTION OF THE INVENTION

Figure 2:
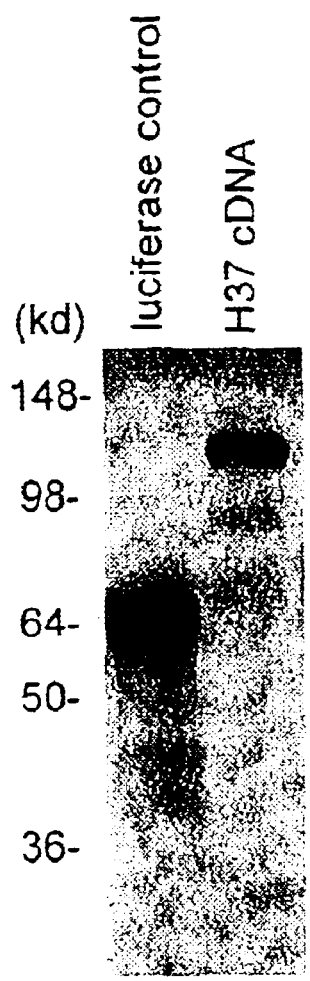
FIG. 2 shows a protein gel containing the in vitro translation product of the H37 cDNA.
Figure 3A:
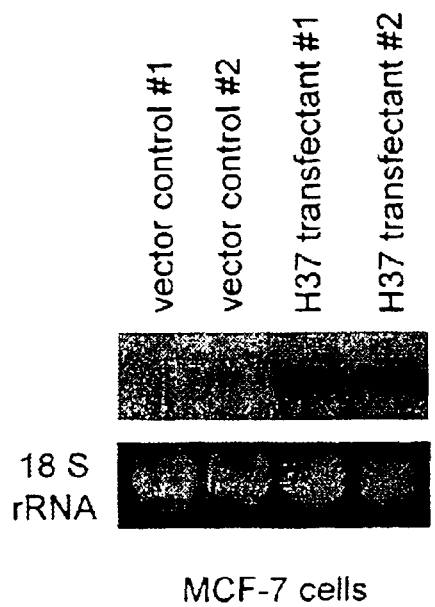
FIGS. 3A and 3B are Northern blots showing the H37 mRNA transcript levels achieved in MCF-7 and CaOv-3 cells transfected with the H37 cDNA.
Figure 3B:
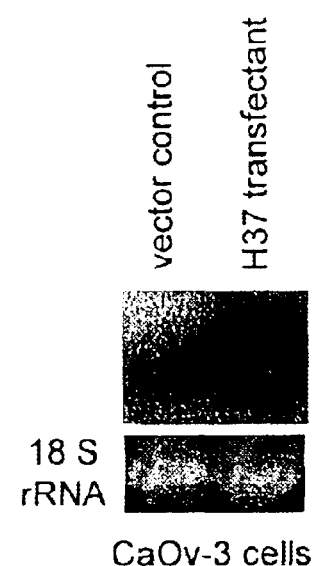
Figure 4:
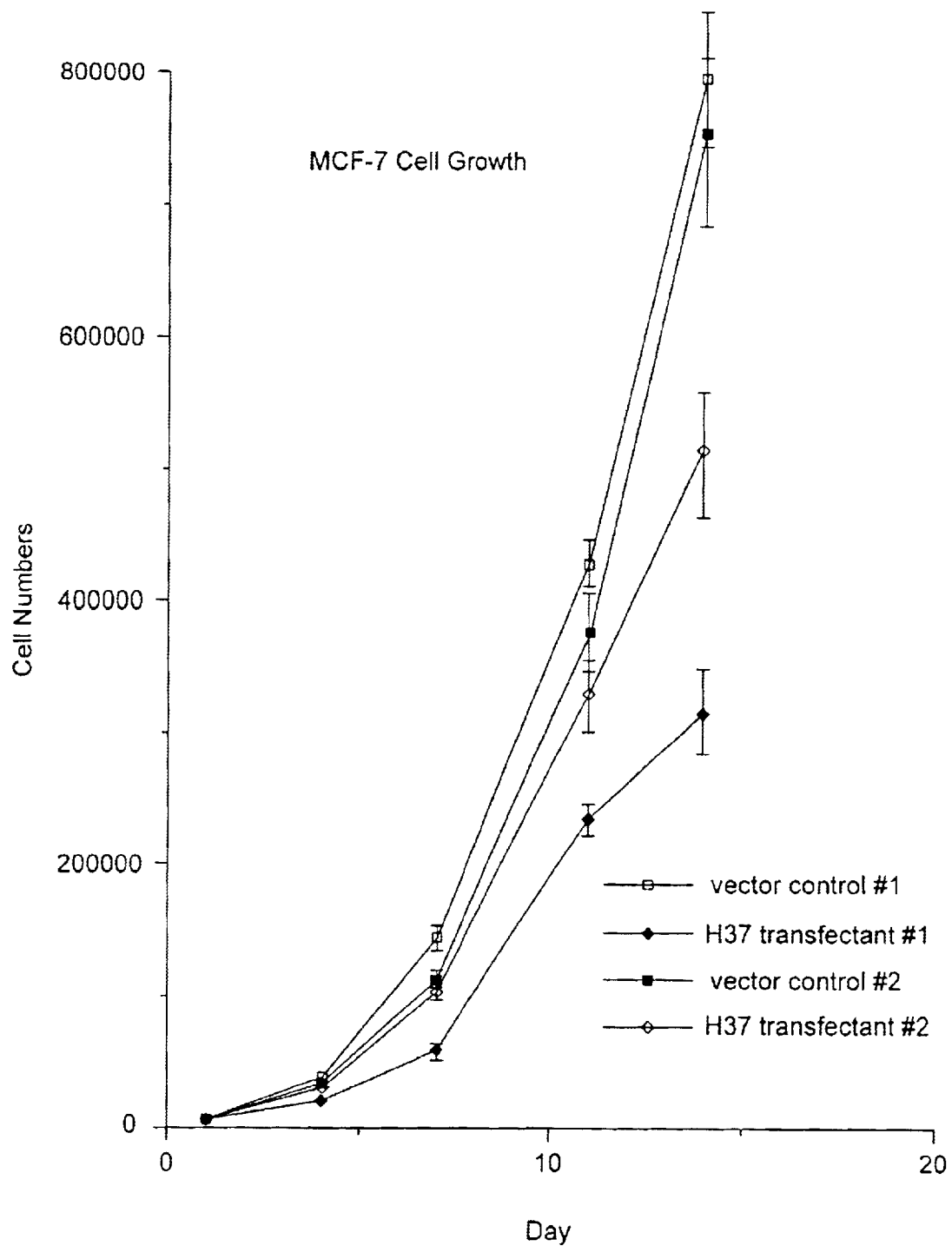
FIG. 4 shows a graph of the growth of MCF-7 cells transfected with H37 as compared to vector control cells.
Figure 5:
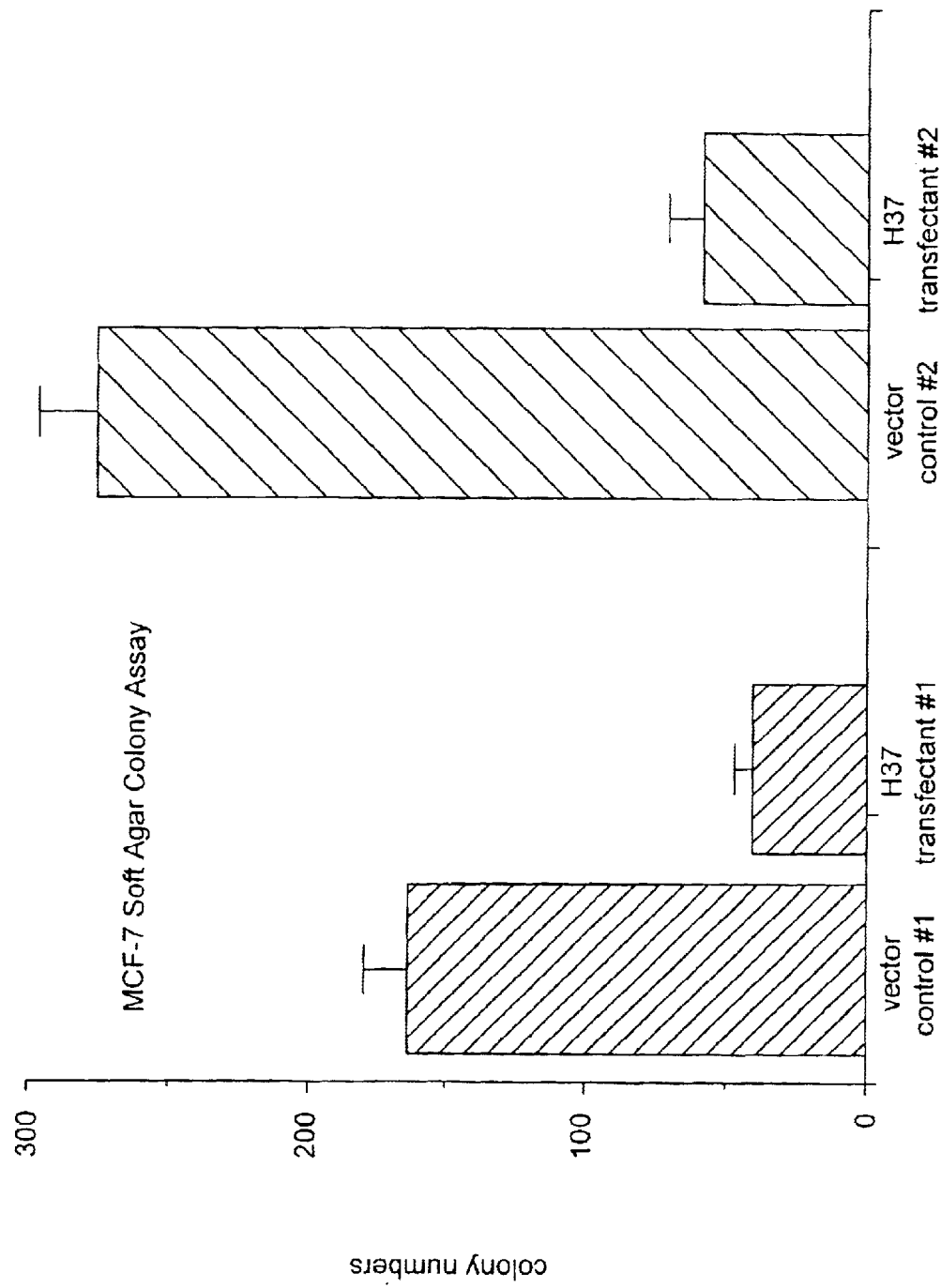
FIG. 5 is a bar graph of a soft agar colony assay of MCF-7 cells transfected with H37 as compared to control cells.
Figure 6:
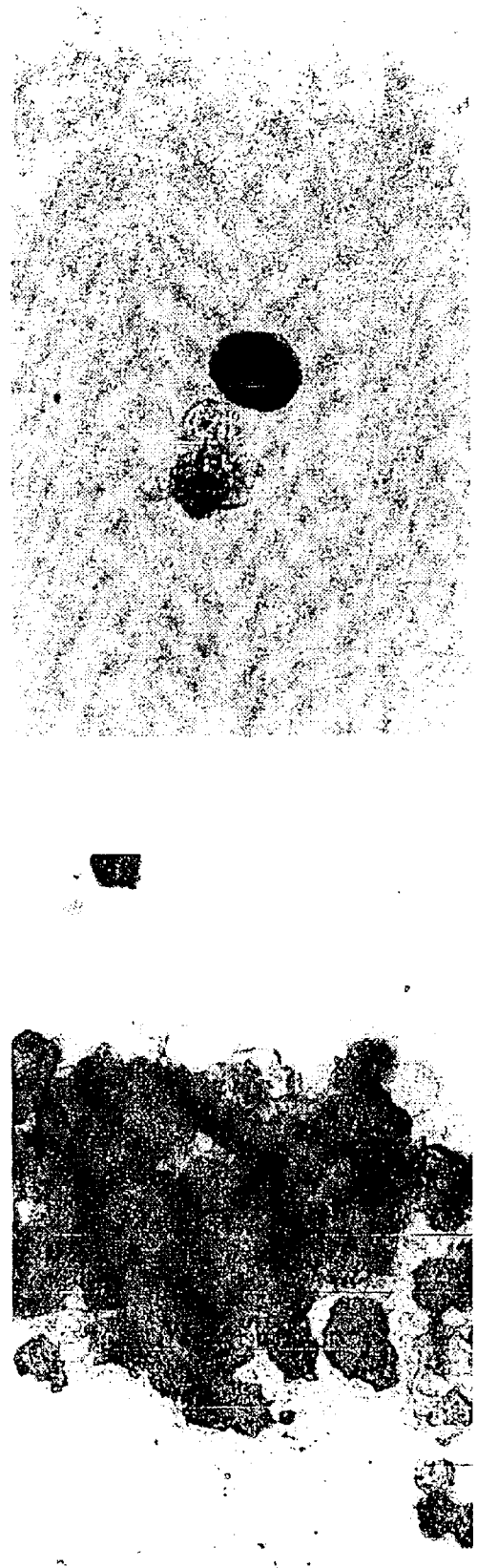
FIGS. 6A and 6B are photographs showing the results of a soft agar colony assay of MCF-7 cells transfected with H37 as compared to vector control cells (close-up views of single representative colonies).
Figure 7:
FIG. 7 is a photograph showing the results of a soft agar colony assay of CaOv-3 cells transfected with H37 as compared to vector control cells (view of entire plates).

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the rat. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

As used herein, the terms "hybridize", "hybridizing", "hybridizes" and the like, used in the context of polynucleotides, are meant to refer to conventional hybridization conditions. "Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured nucleic acid sequences to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, are exemplified by: (1) hybridization in 50% formamide, 2×SSC, 0.1% SDS, 10 mg/ml salmon sperm DNA, and 10% dextran sulfate, at 42° C. for 16 hours followed by a washing in 2×SSC, 0.1% SDS at 25° C. for 10 min (three times), and washed in the same solution at 65° C. for 5 min (twice) and are generally identified by, but not limited to, those that: (2) employ conditions of low ionic strength and high temperature for washing, for example 0.015 M sodium chloride/0.0015 M sodium citrate/0.1% sodium dodecyl sulfate at 50° C.; (3) employ during hybridization a denaturing agent, such as formamide, for example, about 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (4) employ 50% formamide, about 2–5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium. citrate) and 50% formamide at 55° C., followed by a high-stringency wash consisting of 0.1×SSC containing EDTA at 55° C.

As disclosed herein, the "H37 gene", a term which refers to the gene whose nucleic acid sequence is shown in SEQ ID NO. 1 and whose amino acid sequence is shown in SEQ ID NO. 2 functions as tumor suppressor. The H37 gene was initially identified in a differential screening experiment as one of the genes whose expression levels change in association with HER-2/neu proto-oncogene overexpression (Nucleic Acids Res. 1999 Oct. 15;27(20):4008–17). When the H37 gene sequence was compared with genes in the GenBank database, it was found to have been previously isolated as LUCA15 (see e.g. Oncogene 1999 Apr. 22; 18(16):2589–97) and RBM5 (see e.g. Eur J Hum Genet 1999 May–June; 7(4):478–86; Genomics, 1999 Sep. 1;60 (2):238–40). As disclosed herein, the introduction of H37 cDNA into human breast cancer cells reduces the cell growth in vitro and suppressed anchorage-independent growth. The transfection of a H37 cDNA into one of the homozygous deletion lung cancer cell line resulted in a very low yield of H37-expressing clones. H37 also suppressed anchorage independent growth of A9 mouse fibrosarcoma cells and inhibited tumor formation in nude mice.

Interestingly, H37 localizes to chromosome 3, region 3p21–22, an area of the genome where Loss of Heterozygosity (LOH) occurs in 100% Small Cell Lung Cancer (SCLC) cell lines, >90% of non-SCLC cell lines, and >90% of primary lung cancers (Gazdar et al., Cold Spring Harbor Symp. Quant. Biol., 59: 565–573, (1994). These cytogenetic observations have led lung cancer geneticists to believe that this region may contain one or more tumor suppressor genes which contribute to the development and/or progression of lung cancers. The chromosomal 3p deletion has been also seen in various other types of human malignancies (3p21 region being most frequently implicated) including breast, cervix, bladder, kidney, and head and neck cancers, therefore, this putative gene has been thought to be a potential "general" tumor suppressor gene which may be involved in many types of cancers. After several years of persistent efforts to find this candidate tumor suppressor gene(s), the region of interest has been specifically narrowed down to chromosome 3p21.3 (approx. 370 kb). This observation is based on the discovery of three lung cancer cell lines containing homozygous deletion in this region (i.e. NCI H740, NCI H1450, and GLC 20), and H37 (LUCA15) is one of 20–30 genes contained in the 3p21.3 tumor suppressor locus (Cancer Res. 1996 April; 156:1487–1492).

In this context, researchers have already identified a number of candidate tumor suppressor genes which localize to this region of chromosome 3. For example Kiss et al. suggest that the human C3CER1-located LIMD1 gene has a role in tumor suppression. Hum Genet. 1999 December; 105(6):552–9. Moreover, Frost et al., suggest that the N-acetyltransferase functions of Fus-2 may be relevant to its potential role in cancer. Oncogene 2000 January 6;19(1):161–3. In addition, Daigo et al. provide data which suggests that the aberrant transcription of a gene designated DLC1 (deleted in lung cancer 1), may be involved in carcinogenesis of the lung, esophagus, and kidney. Cancer Res Apr. 15, 1999; 59(8):1966–72.

In addition, in their search for a tumor suppressor gene in the 3p21.3 region, Timmer et al. (Eur J Hum Genet. 1999 May–June; 7(4):478–86) isolated two genes, RBM5 (H37) and RBM6, noting that H37 maps to the region which is homozygously deleted in the small cell lung cancer cell line GLC20 and RBM6 crosses the telomeric breakpoint of this deletion. A sequence comparison in this paper revealed that at the amino acid level both genes show 30% identity. Timmer et al., further note that they contain two zinc finger motifs, a bipartite nuclear signal and two RNA binding motifs, suggesting that the proteins for which H37 and RBM6 are coding have a DNA/RNA binding function and are located in the nucleus. Northern and Southern analysis of H37 and RBM6 performed by Timmer et al. did not reveal any abnormalities. In addition, by SSCP analysis of 16 lung cancer cell lines Timmer et al. found only a single, presumably neutral mutation in H37.

In contrast to their findings with H37, Timmer et al. provide evidence that RBM6 is a tumor suppressor gene. In particular, by RT-PCR Timmer et al. demonstrated the existence of two alternative splice variants of RBM6, one including and one excluding exon 5, in both normal lung tissue and lung cancer cell lines. Exclusion of exon 5 results in a frameshift which would cause a truncated protein of 520 amino acids instead of 1123 amino acids. Timmer et al. further note that in normal lung tissue, the relative amount of the shorter transcript was much greater than that in the lung tumor cell lines, which provides evidence that RBM6 is a tumor suppressor and that its tumor suppressor function may be attributed to the derived shorter protein.

In view of the teachings in the art (e.g. Timmer et al.), it was a surprising and unexpected finding that H37 is a tumor suppressor gene. As illustrated in the Examples below, cells transfected with H37 (and therefore overexpressing its gene products) grow at a much slower rate as compared to the control counterparts. This tumor suppressive effect of H37 is demonstrated in human breast, ovary, lung cancer cell lines as well as a mouse fibrosarcoma cell line via a number of art accepted methods such as cell counting experiments and soft agar colony assays (FIGS. 4–12).

Figure 8:
FIG. 8 is a photograph showing suppressed growth of NCI H740 cells transfected with H37 as compared to vector control cells (view of entire flasks).
Figure 9B:
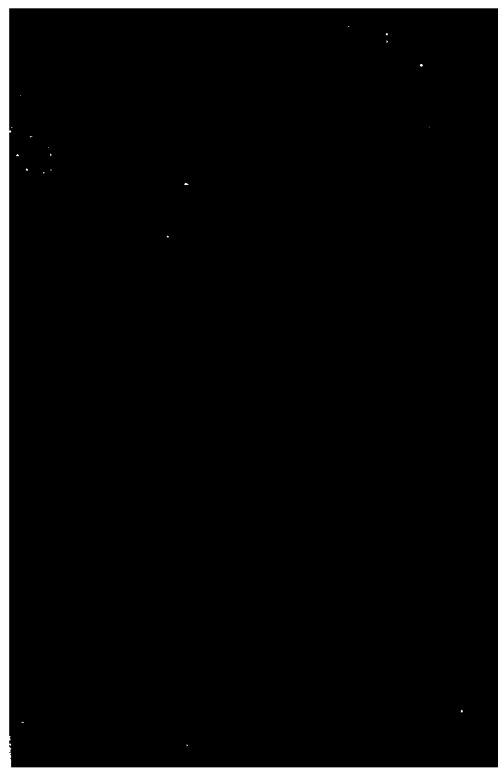
FIGS. 9A and 9B ate close-up view of NCI H740 cell colonies transfected with H37 as compared to vector control cells.
Figure 9A:
Figure 10:
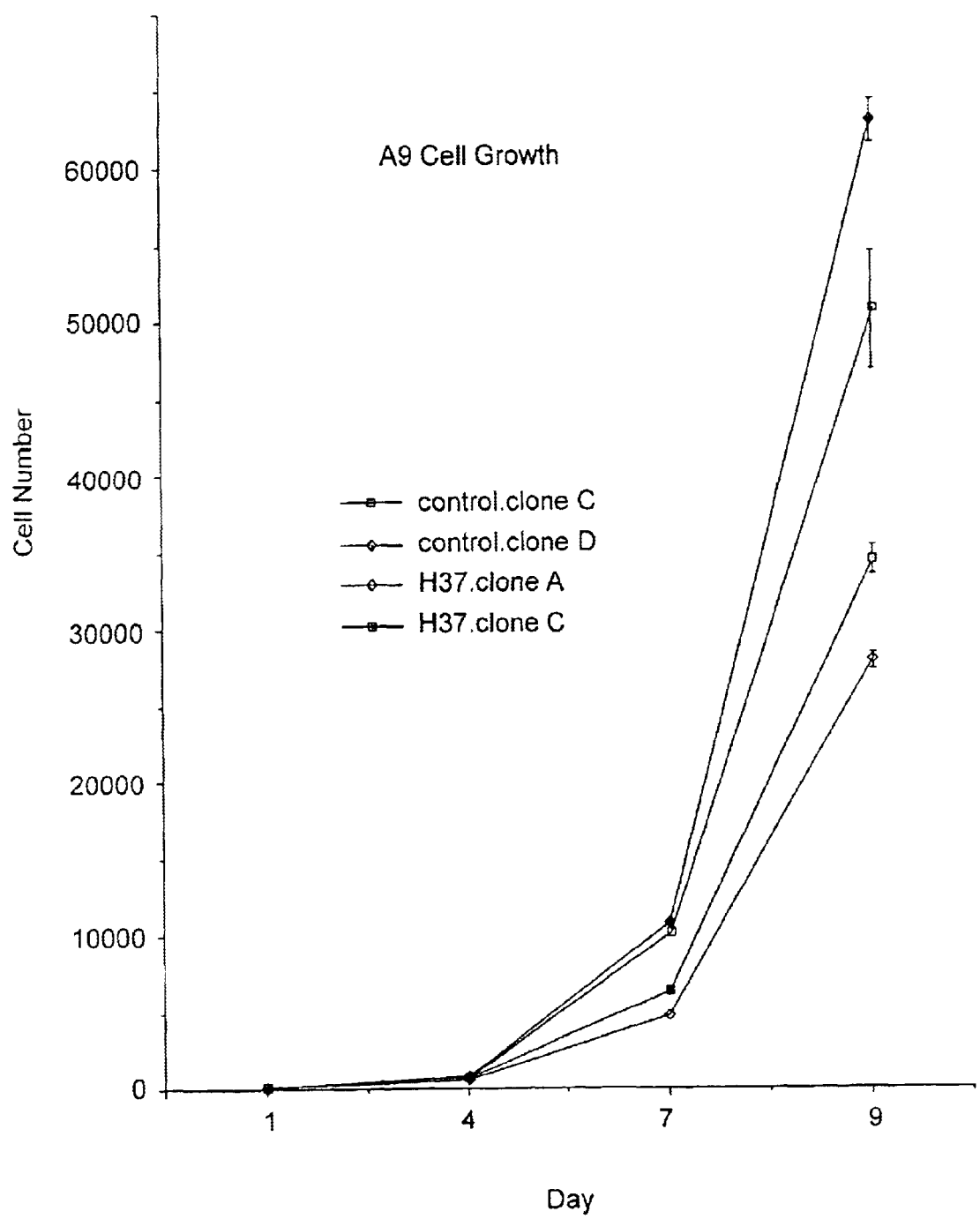
FIG. 10 shows a graph of the growth of A9 cells transfected with H37 as compared to vector control cells (see FIG. 16 for H37 expression level of each clone used).
Figure 12:
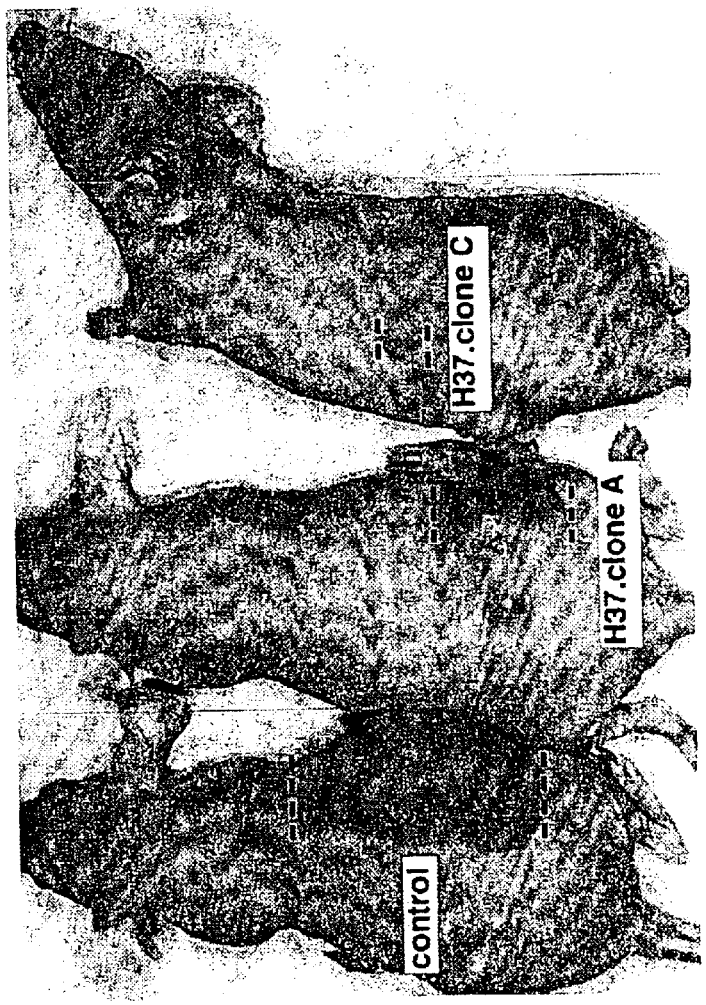
FIG. 12 is a photograph showing that the H37 gene suppresses A9 cell growth in vivo in nude mice. The picture shows appearances of representative tumors from each cell type, photograph taken at day 27 after inoculation.

Strikingly, when the H37 gene was transfected into one of (above-mentioned) homozygous deletion cell lines, NCI H740, cell growth was "most" dramatically suppressed as predicted from the fact that this cell line does not make the H37 gene endogenously (FIGS. 8 & 9). The suppressive effect of this gene in soft agar assays is consistent with the finding that H37 suppresses in vivo tumorigenicity; building upon the above-mentioned in vitro data, A9 cells were injected with or without recombinant H37 into nude mice and compared tumor growth in vivo. As shown in FIG. 12, the H37 gene suppresses the growth of these fibrosarcoma cells in mice. This data is in strong support of the concept that H37 is indeed "the" tumor suppressor gene contained in the 3p21.3 region since our in vivo experiment was the replica of Killary et al. (PNAS, USA. 1992 November; 89:10877–10881) which was the first "functional" (rather than cytogenetic) proof in the field that the locus contains the tumor suppressive activity. In Killary's experiment, in vivo growth of A9 cells were suppressed when transfected with a 2-megabase piece of human chromosome encompassing 3p21–22 identical to our data achieved using a single gene contained in the region.

In addition, differences in transcription level of the H37 tumor suppressor gene in the cancer vs. adjacent normal tissue pairs in primary lung cancer patients were examined via Northern analysis as shown in FIG. 9 (N=normal, T=tumor). In this analysis, 9 out of 11 samples (82%, i.e. patients #1, 2, 3, 4, 5, 6, 7, 8, 11) showed H37 gene expression level decrease in the tumor tissue as compared to the (normal) level in their normal tissue counterpart. This data provides evidence that an alteration (in this case a reduction) in H37 gene expression is involved in the oncogenesis.

Without being bound by a specific theory, a potential mechanism by which this "non-structurally mutated" gene may be inactivated or altered includes disturbances in regulatory elements. A good example of for this si promoter hypermethylation as shown in the recently characterized 3p21.3 gene RASSF1 (Dammann et al., Nat Genet 25, 315–9 (2000) which is believed to be of lesser importance in NSCLC (Agathanggelou et al., Oncogene 20, 1509–18 (2001)). Alternatively, tumor suppression by "haploinsufficiency" (characterized by having an intact remaining allele) (Largaespada et al., J Exp Med 193, F15-8 (2001)) may contribute to the observed biological characteristics of H37.

Figure 16:
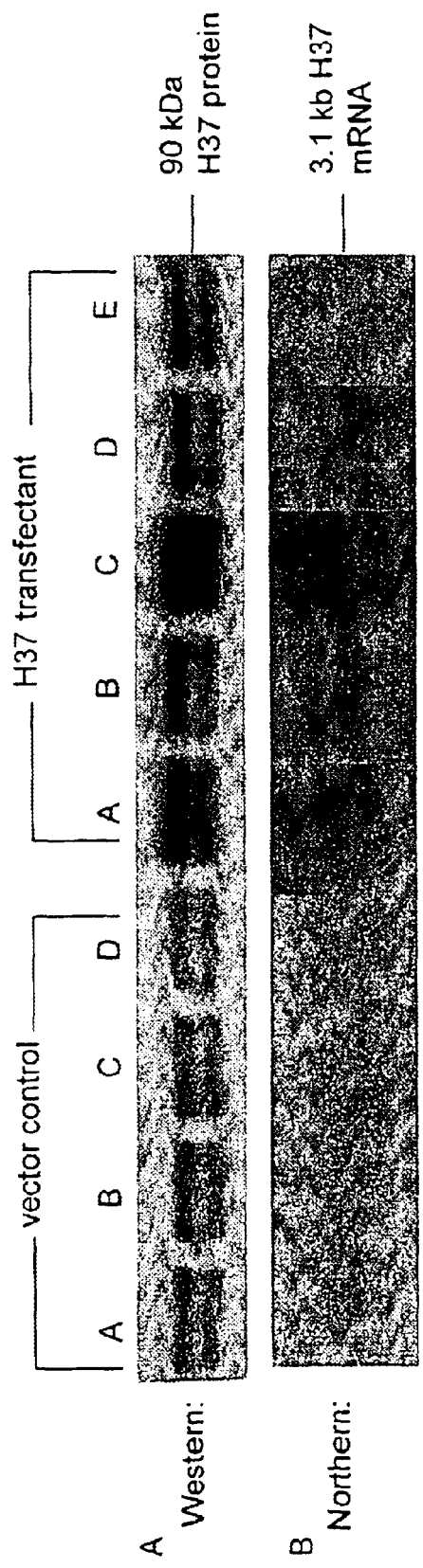
FIGS. 16A and 16B are comparisons of Western and Northern blots showing the expression of H37 protein and mRNA in transfected A9 cell clones.

In order to study the H37 expression at a protein level, polyclonal antibodies recognizing the H37 protein were generated using either 17-mer peptide or c-terminal half of the recombinant H37 as epitopes (FIG. 15) By use of thus generated antibodies, H37 expression levels in single-cell-expanded clones of transfected cells were confirmed at the protein level which correlate well with H37 mRNA transcript levels (FIG. 16). In addition, reduced expression of H37 mRNA was observed in 82% of primary non-small cell lung cancers (NSCLC) tested compared with adjacent normal tissues. Moreover, as demonstrated by immunohistochemistry, 73% of NSCLC contain reduced level of H37 protein compared with adjacent normal bronchial cells. Altogether, these results support the H37's role as a tumor suppressor gene.

Figure 17:
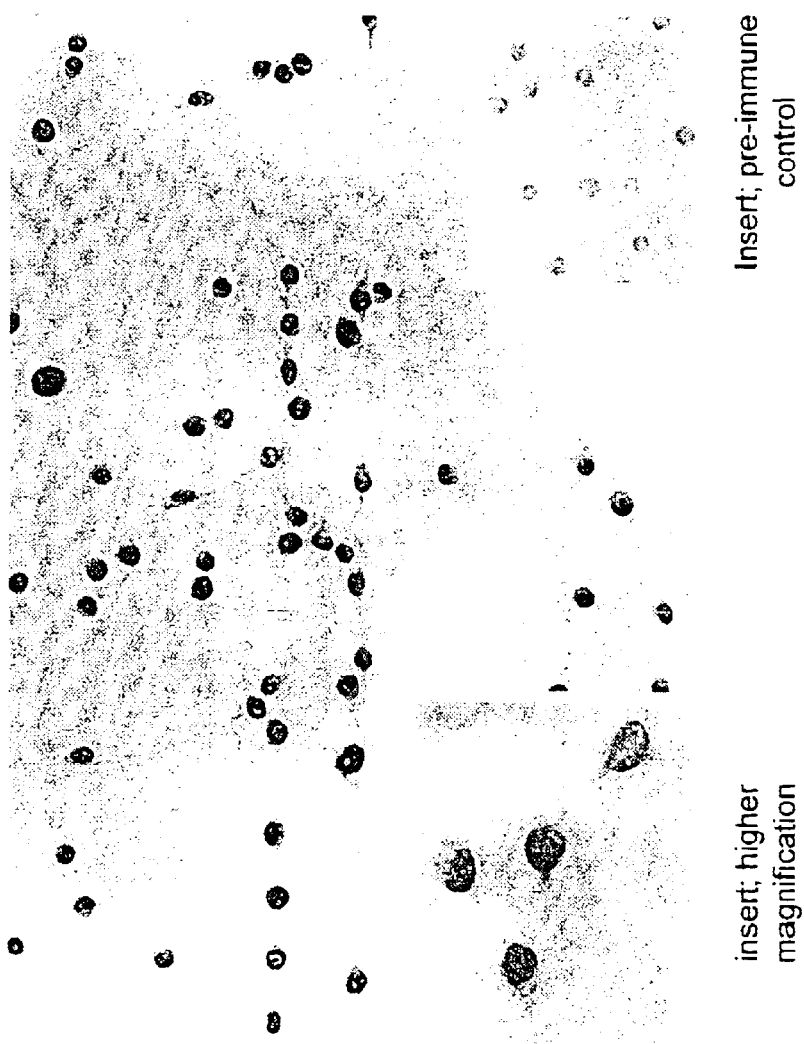
FIG. 17 is a photograph of immunohistochemical staining of A9 cells using the antibody raised against the H37 protein demonstrating cellular localization of the protein into the nucleus.
Figure 19C:
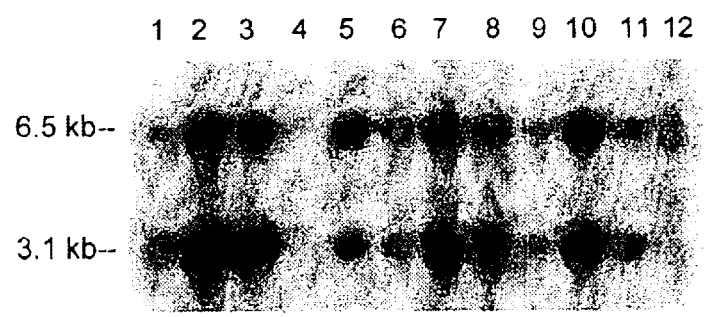
Figure 20A:
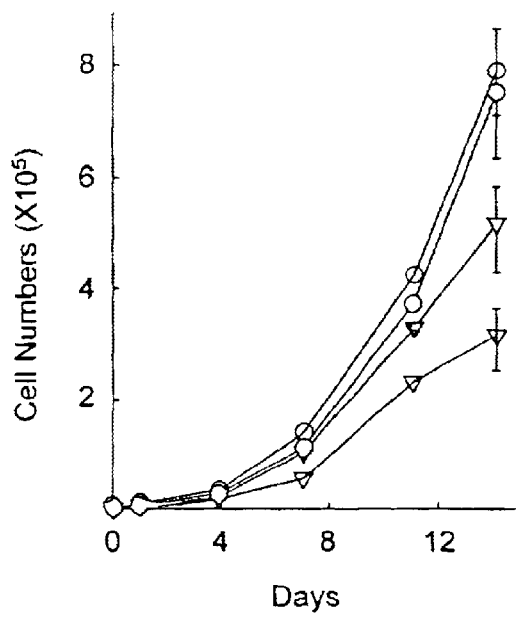
FIG. 20 shows the effects of H37 transfection on MCF-7 cell growth characteristics. All the experiments were done immediately following the two-week selection in G418. The MCF-7 cells used were pooled populations of two pBK-CMV transfected cell lines (neo1 and 2) and two H37 transfected lines (H37.1 and .2). Neol and H37.1 vs. neo2 and H37.2 are different in lipid:DNA ratio during transfection. (A) Growth curves of H37-transfected MCF-7 cells. The cells were plated in triplicate in 60 mm dishes ($10^4$ cells in 4 ml media per dish). After plating (day 0), seeding density was measured at day 1, and cells were counted at day 4, 7, and 11 by Coulter cell counter (○, neo1; ●, neo2; ▽, H37.1; ▼, H37.2). (B) Soft agar colony assay. Cells ($2 \times 10^4$/60 mm dish) were cultured in soft-agar medium. Three weeks later, cells were stained in tetrazolium dye, and colonies of >20 cells were counted. The insert shows a representative colony each from the neo and the H37 transfectants. The soft agar assay was performed separately for each pair of cell lines i.e. neo1 & H37.1 vs. neo2 & H37.2. (C) Comparison of H37 gene and protein expression in various control cell lines vs. MCF-7 transfectants. Upper panels represent Northern blot analysis: (1–5, lung cancer) 1, NCI-H596; 2, A 427; 3, Calu-1; 4, SW 900; 5, SK-Lu-1; (6–9, MCF-7) 6, neo1; 7, neo2; 8, H37.1; 9, H37.2). Lower panels represent Western blot analysis: 1, CaOv-3 (ovarian cancer); (2–4, lung cancer) 2, NCI-H1299; 3, Calu-6; 4, NCIH838; (5–8, MCF-7) 5, neo1; 6, neo2; 7, H37.1; 8, H37.2. 18S rRNA and 55 kDa (β-tubulin are shown as a loading control for Northern and Western blot analyses respectively.
Figure 20C:
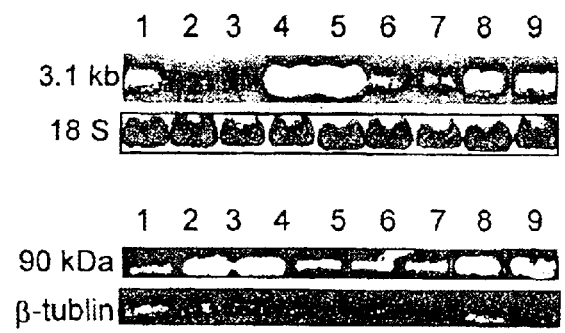
Figure 20B:
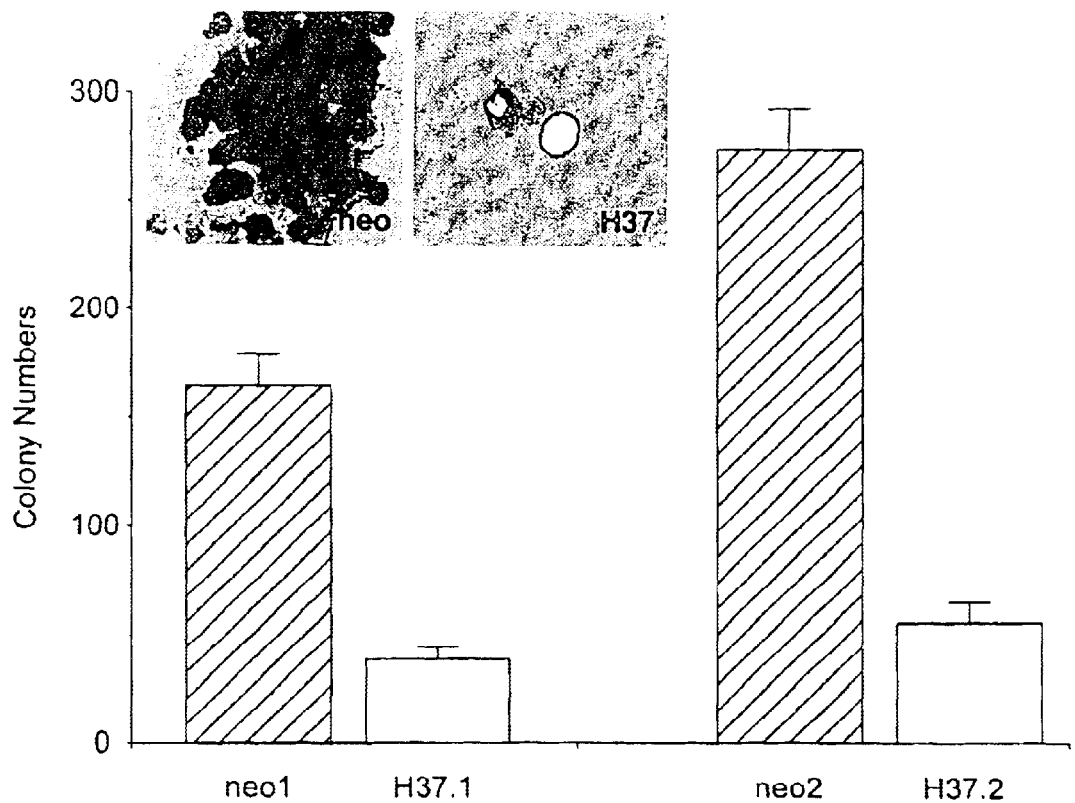
Figure 21A:
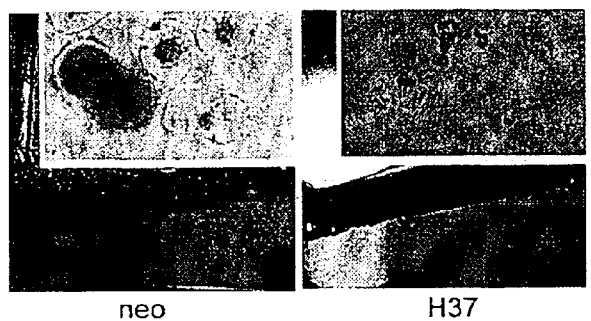
FIG. 21 shows the effects of H37 transfection on NCI-H740 and A9 cells. (A) NCI-H740 cells. The entire flask view of the cell suspension was photographed after one-month selection in G418 (100 μg/ml) following transfection (inserts: close-up view of colonies). (B-D) A9 cells. Single-cell-expanded clones of the two empty vector controls (neo1, and 2) and the two H37 transfectants (H37.1 and .2) were selected. (B) Detection of H37 mRNA and protein expression. Northern (upper panels, 18 S ribosomal RNA as a loading control) and Western (bottom panels, 55 kDa (β-tubulin as a loading control) blot analyses were performed to compare the H37 expression levels in each transfectant. (C) Growth curves and soft agar assay. Cells were plated in triplicate in 6 well plate (5000 cells in 2 ml media per well). After plating (day 0), seeding density was measured at day 1, and cells were counted at day 4, 7, and 11 by Coulter cell counter ((○, neo1; ●, neo2; ▽, H37.1; ▼, H37.2). Cells were cultured in soft agar (4000 cells/35 mm dish) and were grown up to two weeks before colonies were stained in tetrazolium dye for photograph. (D) Tumor formation in nude mice. $1 \times 10^6$ cells of the A9 transfectants were injected into mid-back region of mice (10 mice per each group). Tumors were measured in three dimensions on the indicated days (○, parent; ●, neo(pool): pooled population of cells transfected with the empty vector; ▽, H37.1; ▼, H37.2).
Figure 21B:
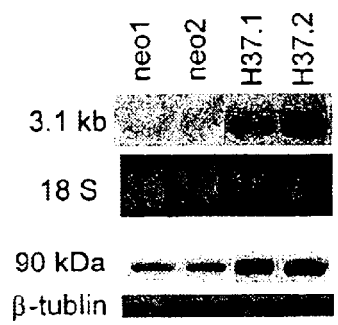
Figure 21C:
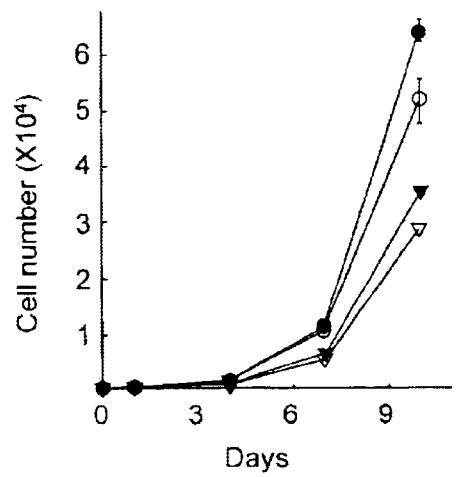
Figure 21D:
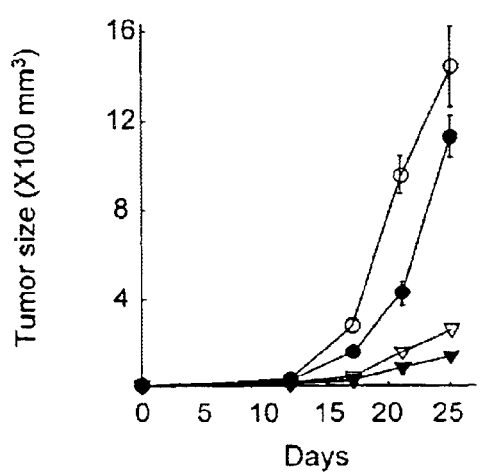

As expected from the presence of such functional/structural motifs in the H37 protein as a bipartite nuclear signal, two zinc finger motifs, and two RNA binding motifs, H37 localizes into the nucleus in a cell (FIG. 17). This finding suggests that H37 may function as an important transcriptional factor which somehow interferes with transcription of a set of genes involved in cellular proliferation analogous to many other tumor suppressor genes, i.e. p53, RB, BRCA1.

As discussed in detail below, the above-mentioned in vitro and in vivo data illustrating the tumor suppressive function of the H37 gene provides the basis for a variety of diagnostic and therapeutic methods. In illustrative diagnostic methods, the status of the H37 gene is evaluated as an indicator of cancer and oncogenic processes. In illustrative therapeutic methods, the H37 gene is introduced into cells having disregulated cell growth as a means to suppress such disregulated growth.

I. Diagnostic Methods

A. General Diagnostic Protocols and Their Uses

As disclosed herein, H37 exhibits specific properties that are analogous to those found in a family of molecules whose polynucleotides, polypeptides, and anti-polypeptide antibodies are used in well known diagnostic assays that examine conditions associated with dysregulated cell growth such as cancer (see, e.g., both its specific pattern of tissue expression as well as its altered expression in lung cancers as described for example in Examples 3 and 5). The best-known member of this class is PSA, the archetypal marker that has been used by medical practitioners for years to identify and monitor the presence of prostate cancer (see, e.g., Merrill et al., J. Urol. 163(2): 503–5120 (2000); Polascik et al., J. Urol. Aug; 162(2):293–306 (1999) and Fortier et al., J. Nat. Cancer Inst. 91(19): 1635–1640(1999)). A variety of other diagnostic markers are also used in this context including Rb, p53 and K-ras (see, e.g., D'Amico et al., J Thorac Cardiovasc Surg 1999 April; 117(4):736–743; Tulchinsky et al., Int J Mol Med 1999 July 4(1):99–102 and Minimoto et al., Cancer Detect Prev 2000;24(1):1–12). Therefore, this disclosure of the H37 polynucleotides and polypeptides (as well as the H37 polynucleotide probes and anti-H37 antibodies used to evaluate the presence of these molecules) and their properties allows skilled artisans to utilize these molecules in methods that are analogous to those used, for example, in a variety of diagnostic assays directed to examining conditions associated with cancer.

Typical embodiments of diagnostic methods which utilize the H37 polynucleotides, polypeptides and antibodies are analogous to those methods from well-established diagnostic assays which employ, e.g., PSA polynucleotides, polypeptides and antibodies. For example, just as PSA polynucleotides are used as probes (for example in Northern analysis, see, e.g., Sharief et al., Biochem. Mol. Biol. Int. 33(3):567–74(1994)) and primers (for example in PCR analysis, see, e.g., Okegawa et al., J. Urol. 163(4): 1189–1190 (2000)) to observe the presence and/or the level of PSA mRNAs in methods of monitoring PSA expression or the metastasis of prostate cancers, the H37 polynucleotides described herein can be utilized in the same way to detect H37 underexpression or the metastasis of lung and other cancers having an alteration in the expression of this gene. Alternatively, just as PSA polypeptides are used to generate antibodies specific for PSA which can then be used to observe the presence and/or the level of PSA proteins in methods to monitor PSA protein underexpression (see, e.g., Stephan et al., Urology 55(4):560–3 (2000)) or the metastasis of prostate cells (see, e.g., Alanen et al., Pathol. Res. Pract. 192(3):233–7 (1996)), the H37 polypeptides described herein can be utilized to generate antibodies for use in detecting H37 underexpression or the metastasis of lung cells and cells of other cancers having an alteration in the expression of this gene.

Specifically, because metastases involves the movement of cancer cells from an organ of origin (such as the lung or etc.) to a different area of the body (such as a lymph node), assays which examine a biological sample for the presence of cells having an alteration in the expression of H37 polynucleotides and/or polypeptides can be used to provide evidence of metastasis. For example, when a biological sample from tissue that normally contains H37-expressing cells is found to have an influx of cells with reduced H37 expression, this finding is indicative of metastasis.

Alternatively H37 polynucleotides and/or polypeptides can be used to provide evidence of cancer, for example, when cells in a biological sample that normally expresses H37 or express H37 at a different level ate found to have a decreased expression of H37 (see, e.g., the H37 expression in lung cancer cells). In such assays, artisans may further wish to generate supplementary evidence of metastasis by testing the biological sample for the presence of a second tissue restricted marker (in addition to H37) such as RB, PSA, PSCA etc. (see, e.g., Alanen et al., Pathol. Res. Pract. 192(3): 233–237 (1996)).

Just as PSA polynucleotide fragments and polynucleotide variants are employed by skilled artisans for use in methods of monitoring PSA, H37 polynucleotide fragments and polynucleotide variants are used in an analogous manner. In particular, typical PSA polynucleotides used in methods of monitoring PSA are probes or primers which consist of fragments of the PSA cDNA sequence. Illustrating this, primers used to PCR amplify a PSA polynucleotide must include less than the whole PSA sequence to function in the polymerase chain reaction. In the context of such PCR reactions, skilled artisans generally create a variety of different polynucleotide fragments that can be used as primers in order to amplify different portions of a polynucleotide of interest or to optimize amplification reactions (see, e.g., Caetano-Anoles, G. Biotechniques 25(3): 472–476, 478–480 (1998); Robertson et al., Methods Mol. Biol. 98:121–154 (1998)). An additional illustration of the use of such fragments is provided in Example 3, where a H37 polynucleotide fragment is used as a probe to show the expression of H37 RNAs in cancer cells. In addition, variant polynucleotide sequences are typically used as primers and probes for the corresponding mRNAs in PCR and Northern analyses (see, e.g., Sawai et al., Fetal Diagn. Ther. 1996 November–December 11(6):407–13 and Current Protocols In Molecular Biology, Volume 2, Unit 2, Frederick M. Ausubel et al. eds., 1995)). Polynucleotide fragments and variants are useful in this context where they are capable of binding to a target polynucleotide sequence (e.g. the H37 polynucleotide shown in SEQ ID NO: 1) under conditions of high stringency.

Furthermore, PSA polypeptides which contain an epitope that can be recognized by an antibody are used in methods of monitoring PSA. H37 polypeptide fragments and polypeptide analogs or variants can also be used in an analogous manner. This practice of using polypeptide fragments or polypeptide variants to generate antibodies (such as anti-PSA antibodies) is typical in the art with a wide variety of systems such as fusion proteins being used by practitioners (see, e.g., Current Protocols In Molecular Biology, Volume 2, Unit 16, Frederick M. Ausubel et al. eds., 1995). In this context, each epitope(s) functions to provide the architecture with which an antibody. Typically, skilled artisans create a variety of different polypeptide fragments that can be used in order to generate immune responses specific for different portions of a polypeptide of interest (see, e.g., U.S. Pat. Nos. 5,840,501 and 5,939,533). For example it may be preferable to utilize a polypeptide comprising one of the H37 biological motifs or available in the art. Polypeptide fragments, variants or analogs are typically useful in this context as long as they comprise an epitope capable of generating an antibody specific for a target polypeptide sequence (e.g. the H37 polypeptide shown in SEQ ID NO: 2).

As shown herein, the H37 polynucleotides and polypeptides (as well as the H37 polynucleotide probes and anti-H37 antibodies used to evaluate the presence of these molecules) exhibit specific properties that make them useful in diagnosing cancers such as cancers of the lung. Diagnostic assays that measure the presence of H37 gene products, in order to evaluate the presence or onset of a disease condition described herein, such as lung cancer, are used to identify patients for preventive measures or further monitoring, as has been done so successfully with PSA. Moreover, these materials satisfy a need in the art for molecules having similar or complementary characteristics to PSA in situations where, for example, a definite diagnosis of metastasis of prostatic origin cannot be made on the basis of a test for a single marker alone (see, e.g., Alanen et al., Pathol. Res. Pract. 192(3): 233–237 (1996)), and consequently, materials such as H37 polynucleotides and polypeptides (as well as the H37 polynucleotide probes and anti-H37 antibodies used to evaluate the presence of these molecules) must be employed to confirm metastases.

Finally, in addition to their use in diagnostic assays, the H37 polynucleotides disclosed herein have a number of other specific utilities such as their use in the identification of oncogenetic associated chromosomal abnormalities in the 3p21–22 chromosomal region to which the H37 gene maps. Moreover, in addition to their use in diagnostic assays, the H37-related proteins and polynucleotides disclosed herein have other utilities such as their use in the forensic analysis of tissues of unknown origin (see, e.g., Takahama K Forensic Sci Int 1996 Jun. 28; 80(1–2): 63–9).

The polynucleotides of the preceding paragraphs have a number of different specific uses. The human H37 gene maps to the chromosomal location 3p21–22. For example, because the H37 gene maps to this chromosome, polynucleotides that encode different regions of the H37 protein are used to characterize cytogenetic abnormalities of this chromosomal locale, such as abnormalities that are identified as being associated with various cancers. In certain genes, a variety of chromosomal abnormalities including rearrangements have been identified as frequent cytogenetic abnormalities in a number of different cancers (see e.g. Krajinovic et al., Mutat. Res. 382(3–4): 81–83 (1998); Johansson et al., Blood 86(10): 3905–3914 (1995) and Finger et al., P.N.A.S. 85(23): 9158–9162 (1988)). Thus, polynucleotides encoding specific regions of the H37 protein provide new tools that can be used to delineate, with greater precision than previously possible, cytogenetic abnormalities in the chromosomal region that encodes H37 that may contribute to the malignant phenotype. In this context, these polynucleotides satisfy a need in the art for expanding the sensitivity of chromosomal screening in order to identify more subtle and less common chromosomal abnormalities (see e.g. Evans et al., Am. J. Obstet. Gynecol 171(4): 1055–1057 (1994)).

Another aspect of the present invention relates to methods for detecting H37 polynucleotides and H37-related proteins, as well as methods for identifying a cell that expresses H37. The expression profile of H37 makes it a diagnostic marker for aberrant cell growth. Accordingly, the status of H37 gene products provides information useful for predicting a variety of factors including susceptibility to advanced stage disease, rate of progression, and/or tumor aggressiveness. As discussed in detail herein, the status of H37 gene products in patient samples can be analyzed by a variety protocols that are well known in the art including immunohistochemical analysis, the variety of Northern blotting techniques including in situ hybridization, RT-PCR analysis (for example on laser capture micro-dissected samples), Western blot analysis and tissue array analysis.

More particularly, the invention provides assays for the evaluation of H37 polynucleotides in a biological sample, such lung, and other tissues, cell preparations, and the like. H37 polynucleotides which can be evaluated include, for example, a H37 gene or fragment thereof, H37 mRNA, alternative splice variant H37 mRNAs, and recombinant DNA or RNA molecules that contain a H37 polynucleotide. A number of methods for amplifying and/or detecting the presence of H37 polynucleotides are well known in the art and can be employed in the practice of this aspect of the invention.

In one embodiment, a method for detecting an H37 mRNA in a biological sample comprises producing cDNA from the sample by reverse transcription using at least one primer; amplifying the cDNA so produced using an H37 polynucleotides as sense and antisense primers to amplify H37 cDNAs therein; and detecting the presence of the amplified H37 cDNA. Optionally, the sequence of the amplified H37 cDNA can be determined.

In another embodiment, a method of detecting a H37 gene in a biological sample comprises first isolating genomic DNA from the sample; amplifying the isolated genomic DNA using H37 polynucleotides as sense and antisense primers; and detecting the presence of the amplified H37 gene. Any number of appropriate sense and antisense probe combinations can be designed from the nucleotide sequence provided for the H37 and used for this purpose.

The invention also provides assays for detecting the presence of an H37 protein in a tissue or other biological sample such as lung and other tissues, and the like. Methods for detecting a H37-related protein are also well known and include, for example, immunoprecipitation, immunohistochemical analysis, Western blot analysis, molecular binding assays, ELISA, ELIFA and the like. For example, a method of detecting the presence of a H37-related protein in a biological sample comprises first contacting the sample with a H37 antibody, a H37-reactive fragment thereof, or a recombinant protein containing an antigen binding region of a H37 antibody; and then detecting the binding of H37-related protein in the sample.

Methods for identifying a cell that expresses (or under expresses) H37 are exemplary embodiments of the invention. In one embodiment, an assay for identifying a cell that underexpresses a H37 gene comprises detecting the presence of lowered H37 mRNA concentrations in the cell. Methods for the evaluation of particular mRNAs in cells are well known and include, for example, hybridization assays using complementary DNA probes (such as in situ hybridization using labeled H37 riboprobes, Northern blot and related techniques) and various nucleic acid amplification assays (such as RT-PCR using complementary primers specific for H37, and other amplification type detection methods, such as, for example, branched DNA, SISBA, TMA and the like). Alternatively, an assay for identifying a cell that expresses a H37 gene comprises evaluating the presence of H37-related protein in the cell. Various methods for the detection of proteins are well known in the art and are employed for the detection of H37-related proteins and cells that express H37-related proteins.

H37 expression analysis is also useful as a tool for identifying and evaluating agents that modulate H37 gene expression. For example, H37 expression is significantly downregulated in lung cancer. Identification of a molecule or biological agent that augments H37 expression in cancer cells is of therapeutic value. For example, such an agent can be identified by using a screen that quantifies H37 expression by RT-PCR, nucleic acid hybridization or antibody binding.

B. Illustrative Methods for Monitoring the Status of H37-Related Genes and Their Products Oncogenesis is known to be a multistep process where cellular growth becomes progressively dysregulated and cells progress from a normal physiological state to precancerous and then cancerous states (see, e.g., Alers et al., Lab Invest. 77(5): 437–438 (1997) and Isaacs et al., Cancer Surv. 23: 19–32 (1995)). In this context, examining a biological sample for evidence of dysregulated cell growth (such as aberrant H37 expression in cancers) allows for early detection of such aberrant physiology, before a pathologic state such as cancer has progressed to a stage that therapeutic options are more limited and or the prognosis is worse. In such examinations, the status of H37 in a biological sample of interest can be compared, for example, to the status of H37 in a corresponding normal sample (e.g. a sample from that individual or alternatively another individual that is not affected by a pathology). An alteration in the status of H37 in the biological sample (as compared to the normal sample) provides evidence of dysregulated cellular growth. In addition to using a biological sample that is not affected by a pathology as a normal sample, one can also use a predetermined normative value such as a predetermined normal level of mRNA expression (see, e.g., Grever et al., J. Comp. Neurol. 1996 Dec. 9; 376(2):306–14 and U.S. Pat. No. 5,837,501) to compare H37 status in a sample.

The term "status" in this context is used according to its art accepted meaning and refers to the condition or state of a gene and its products. Typically, skilled artisans use a number of parameters to evaluate the condition or state of a gene and its products. These include, but ate not limited to the location of expressed gene products (including the location of H37 expressing cells) as well as the level, and biological activity of expressed gene products (such as H37 mRNA, polynucleotides and polypeptides). Typically, an alteration in the status of H37 comprises a change in the location of H37 underexpressing cells and/or an decrease in H37 mRNA and/or protein expression.

H37 status in a sample can be analyzed by a number of means well known in the art, including without limitation, immunohistochemical analysis, in situ hybridization, RT-PCR analysis on laser capture micro-dissected samples, Western blot analysis, and tissue array analysis. Typical protocols for evaluating the status of the H37 gene and gene products are found, for example in Ausubel et al. eds., 1995, Current Protocols In Molecular Biology, Units 2 (Northern Blotting), 4 (Southern Blotting), 15 (Immunoblotting) and 18 (PCR Analysis). Thus, the status of H37 in a biological sample is evaluated by various methods utilized by skilled artisans including, but not limited to genomic Southern analysis (to examine, for example perturbations in the H37 gene), Northern analysis and/or PCR analysis of H37 mRNA (to examine, for example alterations in the polynucleotide sequences or expression levels of H37 mRNAs), and, Western and/or immunohistochemical analysis (to examine, for example alterations in polypeptide sequences, alterations in polypeptide localization within a sample, alterations in expression levels of H37 proteins and/or associations of H37 proteins with polypeptide binding partners). Detectable H37 polynucleotides include, for example, a H37 gene or fragment thereof, H37 mRNA, alternative splice variants, H37 mRNAs, and recombinant DNA or RNA molecules containing a H37 polynucleotide.

The expression profile of H37 makes it a diagnostic marker for local and/or metastasized disease, and provides information on the growth or oncogenic potential of a biological sample. In particular, the status of H37 provides information useful for predicting susceptibility to particular disease stages, progression, and/or tumor aggressiveness. The invention provides methods and assays for deter g H37 status and diagnosing cancers that express H37, such as cancers of the lung. For example, because H37 mRNA is underexpressed in lung cancers relative to normal lung tissue, assays that evaluate the levels of H37 mRNA transcripts or proteins in a biological sample can be used to diagnose a disease associated with H37 dysregulation, and can provide prognostic information useful in defining appropriate therapeutic options.

The expression status of H37 provides information including the presence, stage and location of dysplastic, precancerous and cancerous cells, predicting susceptibility to various stages of disease, and/or for gauging tumor aggressiveness. Moreover, the expression profile makes it useful as an imaging reagent for metastasized disease. Consequently, an aspect of the invention is directed to the various molecular prognostic and diagnostic methods for examining the status of H37 in biological samples such as those from individuals suffering from, or suspected of suffering from a pathology characterized by dysregulated cellular growth, such as cancer.

As described above, the status of H37 in a biological sample can be examined by a number of well-known procedures in the art. For example, the status of H37 in a biological sample taken from a specific location in the body can be examined by evaluating the sample for the presence or absence of H37 expressing cells (e.g. those that express H37 mRNAs or proteins). This examination can provide evidence of dysregulated cellular growth, for example, when H37 under-expressing cells are found in a biological sample that normally contains cells having higher levels of H37, because such alterations in the status of H37 in a biological sample are often associated with dysregulated cellular growth. Specifically, one indicator of dysregulated cellular growth is the metastases of cancer cells from an organ of origin (such as the lung) to a different area of the body (such as a lymph node). In this context, evidence of dysregulated cellular growth is important for example because occult lymph node metastases can be detected in a substantial proportion of patients with cancer, and such metastases are associated with known predictors of disease progression (see, e.g., Murphy et al., Prostate 42(4): 315–317 (2000); Su et al., Semin. Surg. Oncol. 18(1): 17–28 (2000) and Freeman et al., J Urol 1995 August 154(2 Pt 1):474–8).

In one aspect, the invention provides methods for monitoring H37 gene products by determining the status of H37 gene products expressed by cells from an individual suspected of having a disease associated with dysregulated cell growth (such as hyperplasia or cancer) and then comparing the status so determined to the status of H37 gene products in a corresponding normal sample. The presence of aberrant H37 gene products in the test sample relative to the normal sample provides an indication of the presence of dysregulated cell growth within the cells of the individual.

In another aspect, the invention provides assays useful in determing the presence of cancer in an individual, comprising detecting a significant decrease in H37 mRNA or protein expression in a test cell or tissue sample relative to expression levels in the corresponding normal cell or tissue. The presence of altered H37 expression in any of these tissues is useful to indicate the emergence, presence and/or severity of a cancer, since the corresponding normal tissues express H37 mRNA.

In a related embodiment, H37 status is determined at the protein level rather than at the nucleic acid level. For example, such a method comprises determining the level of H37 protein expressed by cells in a test tissue sample and comparing the level so determined to the level of H37 expressed in a corresponding normal sample. In one embodiment, the presence of H37 protein is evaluated, for example, using immunohistochemical methods. H37 antibodies or binding partners capable of detecting H37 protein expression are used in a variety of assay formats well known in the art for this purpose.

In a further embodiment, one can evaluate the status H37 nucleotide and amino acid sequences in a biological sample in order to identify perturbations in the structure of these molecules. These perturbations can include insertions, deletions, substitutions and the like. Such evaluations are useful because perturbations in the nucleotide and amino acid sequences are observed in a large number of proteins associated with a growth dysregulated phenotype (see, e.g., Marrogi et al., 1999, J. Cutan. Pathol. 26(8):369–378). For example, a mutation in the sequence of H37 may be indicative of the presence or promotion of a tumor. Such assays therefore have diagnostic and predictive value where a mutation in H37 indicates a potential loss of function or increase in tumor growth.

A wide variety of assays for observing perturbations in nucleotide and amino acid sequences are well known in the art. For example, the size and structure of nucleic acid or amino acid sequences of H37 gene products are observed by the Northern, Southern, Western, PCR and DNA sequencing protocols discussed herein. In addition, other methods for observing perturbations in nucleotide and amino acid sequences such as single strand conformation polymorphism analysis ate well known in the art (see, e.g., U.S. Pat. No. 5,382,510 issued Sep. 7, 1999, and U.S. Pat. No. 5,952,170 issued Jan. 17, 1995).

Additionally, one can examine the methylation status of the H37 gene in a biological sample. Aberrant demethylation and/or hypermethylation of CpG islands in gene 5' regulatory regions frequently occurs in immortalized and transformed cells, and can result in altered expression of various genes. For example, promoter hypermethylation of the pi-class glutathione S-transferase (a protein expressed in normal prostate but not expressed in >90% of prostate carcinomas) appears to permanently silence transcription of this gene and is the most frequently detected genomic alteration in prostate carcinomas (De Marzo et al., Am. J. Pathol. 155(6): 1985–1992 (1999)). In addition, this alteration is present in at least 70% of cases of high-grade prostatic intraepithelial neoplasia (PIN) (Brooks et al, Cancer Epidemiol. Biomarkers Prev., 1998, 7:531–536). In another example, expression of the LAGE-I tumor specific gene (which is not expressed in normal prostate but is expressed in 25–50% of prostate cancers) is induced by deoxy-azacytidine in lymphoblastoid cells, suggesting that tumoral expression is due to demethylation (Lethe et al., Int. J. Cancer 76(6): 903–908 (1998)). A variety of assays for examining methylation status of a gene are well known in the art. For example, one can utilize, in Southern hybridization approaches, methylation-sensitive restriction enzymes which cannot cleave sequences that contain methylated CpG sites to assess the methylation status of CpG islands. In addition, MSP (methylation specific PCR) can rapidly profile the methylation status of all the CpG sites present in a CpG island of a given gene. This procedure involves initial modification of DNA by sodium bisulfite (which will convert all unmethylated cytosines to uracil) followed by amplification using primers specific for methylated versus unmethylated DNA. Protocols involving methylation interference can also be found for example in Current Protocols In Molecular Biology, Unit 12, Frederick M. Ausubel et al. eds., 1995.

Biopsied tissue or peripheral blood can be conveniently assayed for the presence of cancer cells using for example, Northern, dot blot or RT-PCR analysis to detect H37 expression. The presence of RT-PCR amplifiable H37 mRNA provides an indication of the presence of cancer. RT-PCR assays are well known in the art. RT-PCR detection assays for tumor cells in peripheral blood are currently being evaluated for use in the diagnosis and management of a number of human solid tumors. In the cancer field, these include RT-PCR assays for the detection of cells expressing PSA and PSM (Verkaik et al., 1997, Urol. Res. 25:373–384; Ghossein et al., 1995, J. Clin. Oncol. 13:1195–2000; Heston et al., 1995, Clin. Chem. 41:1687–1688).

A further aspect of the invention is an assessment of the susceptibility that an individual has for developing cancer. In one embodiment, a method for predicting susceptibility to cancer comprises detecting H37 mRNA or H37 protein in a tissue sample, a decrease in its presence indicating susceptibility to cancer, wherein the degree of H37 mRNA expression correlates to the degree of susceptibility. In a specific embodiment, the presence of H37 in lung or other tissue is examined, with the relative decrease of H37 in the sample providing an indication of lung cancer susceptibility (or the emergence or existence of a lung tumor). Similarly, one can evaluate the integrity H37 nucleotide and amino acid sequences in a biological sample, in order to identify perturbations in the structure of these molecules such as insertions, deletions, substitutions and the like. The presence of one or more perturbations in H37 gene products in the sample is an indication of cancer susceptibility (or the emergence or existence of a tumor).

The invention also comprises methods for gauging tumor aggressiveness. In one embodiment, a method for gauging aggressiveness of a tumor comprises determining the level of H37 mRNA or H37 protein expressed by tumor cells, comparing the level so determined to the level of H37 mRNA or H37 protein expressed in a corresponding normal tissue taken from the same individual or a normal tissue reference sample, wherein the degree of H37 mRNA or H37 protein expression in the tumor sample relative to the normal sample indicates the degree of aggressiveness. In a specific embodiment, aggressiveness of a tumor is evaluated by determining the extent to which H37 is expressed in the tumor cells, with lower expression levels indicating more aggressive tumors. Another embodiment is the evaluation of the integrity of H37 nucleotide and amino acid sequences in a biological sample, in order to identify perturbations in the structure of these molecules such as insertions, deletions, substitutions and the like. The presence of one or more perturbations indicates more aggressive tumors.

Another embodiment of the invention is directed to methods for observing the progression of a malignancy in an individual over time. In one embodiment, methods for observing the progression of a malignancy in an individual over time comprise determing the level of H37 mRNA or H37 protein expressed by cells in a sample of the tumor, comparing the level so determined to the level of H37 mRNA or H37 protein expressed in an equivalent tissue sample taken from the same individual at a different time, wherein the degree of H37 mRNA or H37 protein expression in the tumor sample over time provides information on the progression of the cancer. In a specific embodiment, the progression of a cancer is evaluated by determing H37 expression in the tumor cells over time, where decreased expression over time indicates a progression of the cancer. Also, one can evaluate the integrity H37 nucleotide and amino acid sequences in a biological sample in order to identify perturbations in the structure of these molecules such as insertions, deletions, substitutions and the like, where the presence of one or more perturbations indicates a progression of the cancer.

The above diagnostic approaches can be combined with any one of a wide variety of prognostic and diagnostic protocols known in the art. For example, another embodiment of the invention is directed to methods for observing a coincidence between the underexpression of H37 gene and H37 gene products (or perturbations in H37 gene and H37 gene products) and a factor that is associated with malignancy, as a means for diagnosing and prognosticating the status of a tissue sample. A wide variety of factors associated with malignancy can be utilized, such as the expression of genes associated with malignancy (e.g. RB, p53, p16 for lung cancer, PSA, PSCA and PSM expression for prostate cancer etc.) as well as gross cytological observations (see, e.g., Bocking et al., 1984, Anal. Quant. Cytol. 6(2):74–88; Epstein, 1995, Hum. Pathol. 26(2):223–9; Thorson et al., 1998, Mod. Pathol. 11(6):543–51; Baisden et al., 1999, Am. J. Surg. Pathol. 23(8):918–24). Methods for observing a coincidence between the expression of H37 gene and H37 gene products (or perturbations in H37 gene and H37 gene products) and another factor that is associated with malignancy are useful, for example, because the presence of a set of specific factors that coincide with disease provides information crucial for diagnosing and prognosticating the status of a tissue sample.

In one embodiment, methods for observing a coincidence between the expression of H37 gene and H37 gene products (or perturbations in H37 gene and H37 gene products) and another factor associated with malignancy entails detecting the underexpression of H37 mRNA or protein in a tissue sample, detecting the underexpression of RB mRNA or protein in a tissue sample and observing a coincidence of H37 mRNA or protein and RB mRNA or protein underexpression. In a specific embodiment, the expression of H37 and RB mRNA in lung tissue is examined, where the coincidence of H37 and RB mRNA underexpression in the sample indicates the existence of lung cancer, lung cancer susceptibility or the emergence or status of a lung tumor.

Methods for detecting and quantifying the expression of H37 mRNA or protein are described herein, and standard nucleic acid and protein detection and quantification technologies are well known in the art. Standard methods for the detection and quantification of H37 mRNA include in situ hybridization using labeled H37 riboprobes, Northern blot and related techniques using H37 polynucleotide probes, RT-PCR analysis using primers specific for H37, and other amplification type detection methods, such as, for example, branched DNA, SISBA, TMA and the like. In a specific embodiment, semi-quantitative RT-PCR is used to detect and quantify H37 mRNA expression. Any number of primers capable of amplifying H37 can be used for this purpose, including but not limited to the various primer sets specifically described herein. In a specific embodiment, polyclonal or monoclonal antibodies specifically reactive with the wild-type H37 protein can be used in an immunohistochemical assay of biopsied tissue.

C. Preferred Diagnostic Embodiments of the Invention

As illustrated above, the status of H37 gene may be evaluated by a variety of methods well known in the art. The evaluation of the status of the H37 gene provides information useful in diagnostic and prognostic protocols which assess cells which may have disregulated growth. In preferred embodiments, the invention consists of methods of detecting evidence of disregulated growth in a cell such as a cell suspected of being cancerous, by examining the status of the H37 gene by any of a number of art accepted protocols such as a genomic Southerns to evaluate gross perturbations of genomic DNA, Northern and PCR analysis to evaluate the levels H37 mRNAs or immunological methods to examine H37 proteins. Such protocols are used to examine the level of H37 expression as well as the presence or absence of mutations within the H37 mRNA or proteins. In this context, these methods are used to compare the status of H37 in the test cell to the status of H37 gene in a corresponding normal cell or to a specific known standard, where an alteration in the status of H37 gene in the test cell relative to the normal cell provides evidence of disregulated growth within the test cell.

In specific illustrative embodiments of these methods, the status of the H37 gene is determined by a protocol selected from the group consisting of Southern hybridization, Northern hybridization, Western blotting, polymerase chain reaction, polynucleotide sequencing, and methylation-specific PCR. In a preferred embodiment of this method, the status of H37 gene is examined by evaluating the level of mRNA transcripts within the cell. In another preferred embodiment, the cell analyzed in this method is from a biopsied tissue sample. In a specific embodiment of this method, the test cell is a human cell. In a more specific embodiment of this method, the test cell is suspected of being a tumor cell. In a highly preferred embodiment, the test cell suspected of being a tumor is selected from the group consisting of a breast cell, a lung cell or a cervical cell.

A related embodiment of this method consists of evaluating a neoplasm in a patient by determining the quantity of functional H37 gene products in cells from neoplastic tissue of the patient, and comparing the quantity of functional H37 gene products in neoplastic cells to the quantity of functional H37 gene products in non-neoplastic cells of the patient, wherein a reduced quantity of functional H37 gene products in the neoplastic cells is indicative of an altered prognosis. In specific illustrative embodiments of these methods, the status of functional H37 gene products is evaluated by a protocol selected from the group consisting of Southern hybridization, Northern hybridization, Western blotting, polymerase chain reaction, polynucleotide sequencing, and methylation-specific PCR. In another preferred embodiment, the neoplastic cell analyzed in this method is from a biopsied tissue sample. In a specific embodiment of this method, the neoplastic cell is a human cell. In a highly preferred embodiment, neoplastic cell is selected from the group consisting of a lung cell, a breast cell or a cervical cell.

The identification of H37 as a tumor suppressor gene allows the skilled artisan to include protocols which assess and monitor the status of this gene in normal and diseased tissue in the arsenal of diagnostic methods used to examine various disease states. In this context, the invention disclosed herein has a number of embodiments. One embodiment includes a method for monitoring human H37 gene products (e.g. H37 polynucleotides and/or polypeptides) by determining the status of H37 gene products expressed by cells in a tissue sample from an individual and then comparing the status so determined to the status of H37 gene products in a corresponding normal sample (including, for example, human cells growing in culture that express normal levels of H37); and then identifying the presence of aberrant H37 gene products in the sample relative to the normal sample. A preferred embodiment of the invention is a method of monitoring the presence of cancer in an individual by monitoring a decrease in H37 mRNA or protein expression in the test sample relative to the normal tissue sample provides an indication of the presence or status of a disease syndrome such as precancerous dysplasia and hyperplasia and cancer. In specific aspects of this embodiment, the cancer occurs in breast, ovarian or lung tissue. Skilled artisans in this technology understand that a related embodiment includes a method for monitoring human H37 gene products (e.g. H37 polynucleotides and/or polypeptides) by determining the status of H37 gene products expressed by a dysplastic, neoplastic or growth altered cells (including, for example, human cells growing in culture) and then comparing the status so determined to the status of H37 gene products in a corresponding normal sample; and then identifying the presence of aberrant H37 gene products in the sample relative to the normal sample, wherein the data obtained from such comparisons is used to obtain information on mechanisms relating to cell growth, and in particular, disregulated cell growth.

Another embodiment of the invention is a method for evaluating a neoplasm in a patient comprising examining the quantity of functional H37 gene products in cells from neoplastic tissue of the patient, and comparing the quantity of functional H37 gene products in neoplastic cells to the quantity of functional H37 gene products in non-neoplastic cells of the patient, wherein a reduced quantity of functional H37 gene products in the neoplastic cells is indicative of growth disregulation. Typically in such embodiments, the status of the H37 gene is determined by a protocol selected from the group consisting of Southern hybridization, Northern hybridization, Western blotting, polymerase chain reaction and polynucleotide sequencing.

Yet another embodiment of the invention is a method of examining a test biological sample comprising a human breast, ovarian or lung cell for evidence of altered cell growth, the method comprising evaluating the levels of H37 polynucleotides in the biological sample, wherein a decrease in the levels of H37 polynucleotides in the test sample relative to a normal tissue sample provide evidence of altered cell growth; and wherein the levels of H37 polynucleotides in the cell are evaluated by contacting the sample with a polynucleotide probe (including primers utilized in PCR analyses) that specifically hybridizes to a H37 nucleotide sequence shown in SEQ ID NO: 1 (which equivalently hybridizes to a nucleotide sequence shown in SEQ ID NO: 3) and evaluating the presence of a hybridization complex formed by the hybridization of the polynucleotide probe with H37 polynucleotides in the sample. In preferred embodiments, the probe hybridizes under stringent conditions such as those described in Example 3. In preferred embodiments of the invention the presence of a hybridization complex is evaluated by Northern analysis and/or polymerase chain reaction. In another aspect of this embodiment, these methods further include evaluating the test biological sample for the presence of an additional factor that is associated with altered cell growth (e.g. a decrease in the expression of another tumor suppressor gene known in the art such as Rb and/or an increase in the expression of an oncogene known in the art such as c-ras). In a specific embodiment of the invention, a decrease in the levels of H37 polynucleotides in the test sample relative to a normal tissue sample provide evidence of lung cancer. In another specific embodiments of the invention, the H37 polynucleotides in the test sample are mRNA.

Yet another embodiment of the invention is a method of examining a test biological sample comprising, for example, a human breast, ovarian or lung cell for evidence of altered cell growth, the method comprising evaluating the levels of H37 polypeptides in the biological sample, wherein a decrease in the levels of H37 polypeptides in the test sample relative to a normal tissue sample provide evidence of altered cell growth; and wherein the levels of H37 polypeptides in the cell are evaluated by contacting the sample with an antibody that immunospecifically binds to a H37 polypeptide sequence shown in SEQ ID NO: 2 and evaluating the presence of a complex formed by the binding of the antibody with H37 polypeptides in the sample. Yet another embodiment of the invention is a method of examining a test biological sample comprising, for example, a human breast, ovarian or lung cell for evidence of altered cell growth, the method comprising evaluating the levels of H37 polypeptides in the biological sample, wherein a decrease in the levels of H37 polypeptides in the test sample relative to a normal tissue sample provide evidence of altered cell growth; and wherein the levels of H37 polypeptides in the cell are evaluated by contacting the sample with an antibody that immunospecifically binds to a H37 polypeptide sequence shown in SEQ ID NO: 4 and evaluating the presence of a complex formed by the binding of the antibody with H37 polypeptides in the sample. In these embodiments, the presence of a complex is typically evaluated by a method selected from the group consisting of ELISA analysis, Western analysis and immunohistochemistry. In preferred embodiments of the invention, a decrease in the levels of H37 polypeptides in the test sample relative to a normal tissue sample provide evidence of cancer such as lung, ovarian, breast, kidney, skeletal muscle or heart cancer. In these methods skilled artisan may further evaluate the test biological sample for the presence of an additional factor that is associated with altered cell growth.

II. Therapeutic Methods

The identification of H37 as a gene that exhibits decreased levels of expression in cancers of the lung (and possibly other cancers), opens a number of therapeutic approaches to the treatment of such cancers. Based on its nuclear localization and presence of two zinc finger motifs in its protein structure, it is possible that H37 functions as a transcription factor involved in modulating the activity of tumor-promoting genes or genes that have some role in tumorigenesis. Accordingly, therapeutic approaches aimed at modulating or restoring the activity of the H37 protein are expected to be useful for patients suffering from lung cancer and other cancers which exhibit decreased levels of H37 expression.

A. Therapeutic Vectors

A large variety of vectors for use in the therapeutic methods described herein can be generated by any of the methods known to the art for the insertion of DNA fragments into a vector, as described, for example, in Maniatis, T, Fritsch, E. F., and Sambrook, J. (1989): Molecular Cloning (A Laboratory manual), Cold Spring Harbor Laboratory, Cold Spring Harbor, N.Y.; and Ausubel, F. M., Brent, R., Kingston, R. E., Moore, D. D., Seidruan, J. G., Smith, J. A., and Struhl, K. (1992): In addition, Current Protocols in Molecular Biology, John Wiley & Sons, New York, may be used to construct H37 encoding gene expression vectors consisting of appropriate transcriptional/translational control signals and the desired H37 cDNA sequence.

Expression of a nucleic acid sequence encoding a H37 may be regulated by a second nucleic acid sequence so that the H37 is expressed in a host infected or transfected with the recombinant DNA molecule. For example, expression of H37 may be controlled by any promoter/enhancer element known in the art. The promoter activation may be tissue specific or inducible by a metabolic product or administered substance. Promoters/enhancers which may be used to control H37 gene expression include, but are not limited to, the native H37 promoter, the cytomegalovirus (CMV) promoter/enhancer (Karasuyama, H., et al., 1989, J. Exp. Med., 169:13), the human β-actin promoter (Gunning, P., et al., 1987, Proc. Natl. Acad. Sci. USA, 84:4831–4835), the glucocorticoid-inducible promoter present in the mouse mammary tumor virus long terminal repeat (HHTV LTR) (1(Klessig, D. F., et al., 1984, Mol. Cell Biol., 4:1354–1362), the long terminal repeat sequences of Moloney murine leukemia virus (MULV LTR) (Weiss, R., et al., 1985, RNA Tumor Viruses, Cold Spring Harbor Laboratory, Cold Spring Harbor, N.Y.), the SV40 early region promoter (Bernoist and Chambon, 1981, Nature 290:304–310), the promoter contained in the 3' long terminal repeat of Rous sarcoma virus (RSV) (Yamamoto et al., 1980, Cell 22:787–797), the herpes simplex virus (HSV) thymidine kinase promoter/enhancer (Wagner et al., 1981, Proc. Natl. Acad. Sci. U.S.A. 78:1441–1445), the regulatory sequences of the metallothionine gene (Brinster et al., 1982, Nature 296:39–42), the adenovirus promoter (Yamada et al., 1985, Proc. Nail. Acad. Sci. U.S.A. 82(11):3567–71), and the herpes simplex virus LAT promoter (Wolfe, J. H., et al., 1992, Nature Genetics, 1:379–384).

Expression vectors compatible with mammalian host cells for use in genetic therapy of tumor or cancer cells, include, but are not limited to: plasmids, retroviral vectors, adenovirus vectors, herpes viral vectors, and non-replicative avipox viruses, as disclosed, for example, by U.S. Pat. No. 5,174,993. In a specific embodiment, a plasmid vector derived from pBK-CMV (Stratagene) was constructed for expression of H37 in mammalian cells by placing the coding sequence for H37 under control of the CMV promoter.

In another specific embodiment, a plasmid vector derived from pCHV-Neo-Bam (Baker, S. J., et al., Science, 1990, 249:912–915), can be constructed for expression of H37 in mammalian cells by placing the coding sequence for H37 under control of the cytomegalovirus (CMV) promoter/enhancer sequences. In another specific embodiment, a retroviral vector, pLLRNL (Miller, A. D., et al., 1985, Proc. Natl. Acad. Sci., USA, 5:431) can be used to construct a vector able to transduce mammalian cells and express H37 protein under the control of the MULV LTR promoter, the CKV promoter, the β-actin promoter or any other effective promoter. In yet another specific embodiment, an adenovirus type 5 (Ad5) deletion mutant, Ad-d1324, and a plasmid, pTG5955 (Rosenfeld, M. A., et al., Cell, 1992, 68:143–155) can be used to construct an adenovirus vector able to infect mammalian cells and express H37 protein under the control of the adenovirus type 2 (Ad2) major late promoter, the CHV promoter, the —-actin promoter or any other effective promoter.

B. Methods of Treatment

Expression vectors may be introduced into cells (such as tumor cells) by a variety of art accepted methods such as calcium phosphate transfection, liposome (for example, LIPOFECTIN)-mediated transfection, DEAE Dextran-mediated transfection, polybrene-mediated transfection, electroporation and any other method of introducing nucleic acid into a cell. A viral expression vector may be introduced into a target cell in an expressible form by infection or transduction. Such a viral vector includes, but is not limited to: a retrovirus, an adenovirus, a herpes virus and an avipox virus. When H37 is expressed in any abnormally proliferating cell, the cell replication cycle is inhibited, resulting in a reduction in the mass of the abnormal tissue, i.e., the tumor or cancer.

A vector able to introduce the gene construct into a target cell and able to express H37 therein in cell proliferation-suppressing amounts can be administered by any effective method. For example, a physiologically appropriate solution containing an effective concentration of active vectors can be administered topically, intraocularly, parenterally, orally, intranasally, intravenously, intramuscularly, subcutaneously or by any other effective means. In particular, the vector may be directly injected into a target cancer or tumor tissue by a needle in amounts effective to treat the tumor cells of the target tissue. Alternatively, a cancer or tumor present in a body cavity such as in the eye, gastrointestinal tract, genitourinary tract (e.g., the urinary bladder), pulmonary and bronchial system and the like can receive a physiologically appropriate composition (e.g., a solution such as a saline or phosphate buffer, a suspension, or an emulsion, which is sterile except for the vector) containing an effective concentration of active vectors via direct injection with a needle or via a catheter or other delivery tube placed into the cancer or tumor afflicted hollow organ. Any effective imaging device such as X-ray, sonogram, or fiberoptic visualization system may be used to locate the target tissue and guide the needle or catheter tube.

In another embodiment, a physiologically appropriate solution containing an effective concentration of active vectors can be administered systemically into the blood circulation to treat a cancer or tumor which cannot be directly reached or anatomically isolated. In yet another embodiment, target tumor or cancer cells can be treated by introducing H37 protein into the cells by any known method. For example, liposomes are artificial membrane vesicles that are available to deliver drugs, proteins and plasmid vectors both in vitro or in vivo (Mannino, R. J. et al., 1988, Biotechniques, 6:682–690) into target cells (Newton, A. C. and Huestis, W. H., Biochemistry, 1988, 27:4655–4659; Tanswell, A. K. et al., 1990, Biochmica et Biophysica Acta, 1044:269–274; and Ceccoll, J. et al. Journal of Investigative Dermatology, 1989, 93:190–194). Thus, H37 protein can be encapsulated at high efficiency with liposome vesicles and delivered into mammalian cells in vitro or in vivo. Liposome-encapsulated H37 protein may be administered topically, intraocularly, parentetally, intranasally, intratracheally, intrabronchially, intramuscularly, subcutaneously or by any other effective means at a dose efficacious to treat the abnormally proliferating cells of the target tissue. The liposomes may be administered in any physiologically appropriate composition containing an effective concentration of encapsulated H37 protein.

C. Ex Vivo Treatment of Cells

In a preferred embodiment of the invention, a growth disregulated cell such as a cancer cell is transduced with a retrovirus vector, an adenovirus vector, a plasmid vector or any other appropriate vector capable of expressing the H37 protein in that tumor cell. A dose of H37 protein expressing retrovirus vector or adenovirus vector or plasmid vector or any other appropriate vector is administered to a cell sample at a dose sufficient to transduce enough cells in the sample to produce a reduction in tumor cell numbers. The cell proliferation of the treated cancer cells will be slowed or terminated followed by a process similar to normal cellular differentiation or cell senescence. Analogously, blood or bone marrow or other tissue is treated ex vivo using an effective dose of a liposome-encapsulated H37 protein.

D. In Vivo Treatment of Cells

Methods of administering viral vectors are well known. In general, the skilled artisan will appreciate that a retroviral vector, an adenovirus vector, a plasmid vector, or any other appropriate vector capable of expressing the H37 protein can be administered in vivo to a growth disregulated cell such as a cancer cell by a wide variety of manipulations. All such manipulations have in common the goal of placing the vector in sufficient contact with the target tumor to permit the vector to transduce or transfect the target cells. In a preferred embodiment, cancers present in the epithelial linings of hollow organs may be treated by infusing the vector suspension into a hollow fluid filled organ, or by spraying or misting into a hollow air filled organ. Thus, the target cell may be present in or among the epithelial tissue in the lining of pulmonary bronchial tree, the lining of the gastrointestinal tract, the lining of the female reproductive tract, genitourinary tract, milk duct tract, bladder, the gall bladder and any other organ tissue accessible to contact with the vector. In another preferred embodiment, the target cell may be located in or on the lining of the central nervous system, such as, for example, the spinal cord, spinal toots or brain, so that vectors infused in the cerebrospinal fluid will contact and transduce the cells of the tumor in that space.

In another preferred embodiment, the target cell is a solid tumor. The skilled artisan will appreciate that the vector can be administered to the tumor by direct injection of the vector suspension into the tumor so that vectors will contact and transduce or transfect the tumor cells inside the tumor. In yet another preferred embodiment, the cancer may be a cancer of the blood, blood forming organs or any organ directly perfused by the blood, so that vectors injected into the blood stream will contact and treat the cells of the cancer. Thus, the cancer may be a leukemia, a lymphoma or other tumor type and the tumor cell may be present in the blood, the bone marrow, the spleen, the thymus, the liver and any other blood perfused organ. The skilled artisan will understand that the vector is administered in a composition comprising the vector together with a carrier or vehicle suitable for maintaining the transduction or transfection efficiency of the chosen vector and promoting a safe infusion. Such a carrier may be a pH balanced physiological buffer, such as a phosphate, citrate or bicarbonate buffers a saline solution, a slow release composition and any other substance useful for safely and effectively placing the vector in contact with abnormally proliferating cells to be treated.

E. Preferred Embodiments

As described above, the H37 gene may be utilized in a therapeutic context in a manner analogous to therapeutic methods used with other tumor suppressor genes such as RB and p53. Such methods are provided, for example in U.S. Pat. No. 5,922,236, which is incorporated herein by reference and which recites a variety of the methodologies and reagents illustrated herein.

In an illustrative embodiment, the invention consists of a method of inhibiting proliferation of a cell comprising introducing into the cell an expression vector which comprises a polynucleotide that encodes a polypeptide having an amino acid sequence as shown in SEQ ID NO: 2; wherein following the introduction, the polypeptide is expressed in the tumor cell so that proliferation of the cell is inhibited. In a specific embodiment, the polynucleotide of this method comprises the nucleotide sequence as shown in SEQ ID NO: 1 from nucleotide (ATG nt #127) to and including (TGA nt #2572). Specific embodiments of H37 proteins comprise a polypeptide having the amino acid sequence of human H37 as shown in FIG. 1. Alternatively, embodiments of H37 proteins comprise variant polypeptides having alterations in the amino acid sequence of human H37 as shown in FIG. 1.

In general, naturally occurring allelic variants of human H37 will share a high degree of structural identity and homology (e.g., 90% or more identity). Typically, allelic variants of the H37 proteins will contain conservative amino acid substitutions within the H37 sequences described herein or will contain a substitution of an amino acid from a corresponding position in a H37 homologue. One class of H37 allelic variants will be proteins that share a high degree of homology with at least a small region of a particular H37 amino acid sequence, but will further contain a radical departure from the sequence, such as a non-conservative substitution, truncation, insertion or frame shift.

Conservative amino acid substitutions can frequently be made in a protein without altering either the conformation or the function of the protein. Such changes include substituting any of isoleucine (I), valine (V), and leucine (L) for any other of these hydrophobic amino acids; aspartic acid (D) for glutamic acid (E) and vice versa; glutamine (Q) for asparagine N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments.

Embodiments of the invention disclosed herein include a wide variety of art accepted variants of H37 proteins such as polypeptides having amino acid insertions, deletions and substitutions. H37 variants can be made using methods known in the art such as site-directed mutagenesis, alanine scanning, and PCR mutagenesis. Site-directed mutagenesis [Carter et al., *Nucl. Acids Res.*, 13.4331 (1986); Zoller et al., *Nucl. Acids Res.*, 10:6487 (1987)], cassette mutagenesis [Wells et al., Gene, 34:315 (1985)], restriction selection mutagenesis [Wells et al., *Philos. Trans. R. Soc. London SerA*, 317:415 (1986)] or other known techniques can be performed on the cloned DNA to produce the H37 variant DNA. Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions [Creighton, *The Proteins*, (W. H. Freeman & Co., N.Y.); Chothia, J. Mol. Biol., 150:1 (1976)]. If alanine substitution does not yield adequate amounts of variant, an isosteric amino acid can be used.

The tumor suppressor function of the above-mentioned variants can be confirmed by the procedures provided in the Examples below.

In a preferred embodiment of this method of inhibiting proliferation of a cell, the cell in which the H37 or H37 variant is introduced is a human tumor cell. In a highly preferred embodiment, the tumor cell is a breast carcinoma cell, a lung carcinoma cell or a cervical carcinoma cell. In yet another embodiment of this invention, the expression vector is a viral vector. In a specific embodiment of this invention, the viral vector is a cytomegalovirus vector, a retroviral vector, an adenoviral vector or a herpes viral vector. Alternatively, the expression vector is a plasmid. In yet another embodiment of this invention, the H37 polynucleotide is operably linked to a H37 gene enhancer or promoter, a retroviral long-terminal repeat, a cytomegalovirus promoter, a β-actin promoter, a glucocorticoid-inducible promoter, a SV40 early region promoter or a herpes simplex virus thymidine kinase promoter. In yet another embodiment of this invention, the expression vector is introduced into the cell by viral infection, liposome-mediated transfection, polybrene-mediated transfection or $CaPO_4$-mediated transfection. In one specific embodiment of this invention, the expression vector is introduced into the cell in vitro. In another specific embodiment of the invention, the expression vector is introduced into the cell in vivo.

III. Compositions of Matter

As disclosed herein, H37 exhibits specific properties that are analogous to those found in a family of molecules whose polynucleotides, polypeptides, and anti-polypeptide antibodies are used in well known diagnostic assays that examine conditions associated with dysregulated cell growth such as cancer (see, e.g., both its specific pattern of tissue expression as well as its altered expression in lung cancers as described for example in Examples 3 and 5). In addition, as disclosed herein, H37 exhibits specific properties that are analogous to those found in a family of molecules whose polynucleotides, polypeptides, and anti-polypeptide antibodies are used to identify and characterize a wide variety of syndromes characterized by aberrant cell growth as well as models for characterizing them that ate well described in the art (see e.g. WO73349A1, which is incorporated herein by reference). In this context, the methods of the invention provided herein ate shown have a number of different utilities. In particular, the identification of the one or more molecules which modulate cellular growth and differentiation (particularly one shown to be associated with pathological conditions) is a crucial element in many typical protocols that are employed in the art for a variety of purposes. Such uses include for example, the use of H37 polynucleotide and polypeptide compositions in the characterization of the physiological roles of these molecules and the biological pathways they influence as well as the development of agonists and antagonists for such molecules and their pathways. Consequently, a wide variety of protocols based on methods pertaining to such interactions are described for these purposes.

In this context, the disclosure provided herein allows for example, a comprehensive characterization of the role of H37 in normal physiological processes as well as its associated pathological conditions including aberrant cell growth such as cancer. As is known in the art, an understanding of the processes involved in pathologies such as cancer is considered a crucial step in the quest to develop new diagnostic and therapeutic modalities for these pathologies. As illustrated above, in view of the disclosure presented herein one skilled in the art will generate H37 compositions of matter that can be used, for example in diagnostic, therapeutic and analytical contexts.

As is known in the art, the identification and characterization of processes involved in aberrant cell growth (e.g. oncogenesis) are of utmost importance to medical practitioners because it is a crucial step in the development of new diagnostic and therapeutic modalities for pathologies associated with these phenomena. Consequently, artisans can use H37 polynucleotide and polypeptide compositions in the characterization of the physiological roles of these molecules and their associated biological pathways, for example in methods of inhibiting proliferation of a human cell selected from the group consisting of a breast cancer cell, an ovarian cancer cell and a lung cancer cell comprising introducing into the cell an expression vector which comprises a polynucleotide that encodes a polypeptide having an amino acid sequence as shown in SEQ ID NO: 2; wherein following the introduction, the polypeptide is expressed in the cell so that proliferation of the cell is inhibited. As noted above, by using H37 polynucleotide and polypeptide compositions in these methods, crucial aspects of cell physiology (e.g. those identified herein as associated with pathological conditions) can be elucidated.

Included herein are pharmaceutical compositions. In this context "Pharmaceutically acceptable" refers to a non-toxic, inert, and/or composition that is physiologically compatible with humans or other mammals. A "pharmaceutical excipient" comprises a material such as an adjuvant, a carrier, pH-adjusting and buffering agents, tonicity adjusting agents, wetting agents, preservative, and the like. In this context, a variety of aqueous carriers may be used, e.g., water, buffered water, 0.8% saline, 0.3% glycine, hyaluronic acid and the like. These compositions may be sterilized by conventional, well-known sterilization techniques, or may be sterile filtered. The resulting aqueous solutions may be packaged for use as is, or lyophilized, the lyophilized preparation being combined with a sterile solution prior to administration. In addition, the compositions may contain pharmaceutically acceptable auxiliary substances as required to approximate physiological conditions, such as pH-adjusting and buffering agents, tonicity adjusting agents, wetting agents, preservatives, and the like, for example, sodium acetate, sodium lactate, sodium chloride, potassium chloride, calcium chloride, sorbitan monolaurate, triethanolamine oleate, etc. for physiological treatment intended for parenteral, topical, oral, nasal, intrathecal, or local (e.g. as a cream or topical ointment) administration.

Typically H37 pharmaceutical compositions for physiological treatment are intended for parenteral, topical, oral, nasal, intrathecal, or local (e.g. as a cream or topical ointment) administration. The pharmaceutical compositions for analytical protocols are intended for parenteral, topical, oral, nasal, intrathecal, or local (e.g. as a cream or topical ointment) administration as well as one of the various administrative routes by which a nucleic acid molecule is transfected into a mammalian cell including lipids such as lipofectin as well as other molecules artisans use for this purpose such as CaPO4 etc. For illustrative molecules used in such compositions, see, e.g., Ausubel et al., Current Protocols in Molecular Biology, Wiley Interscience Publishers, (1995), Volume I, section 9. Preferably, the pharmaceutical compositions are administered parentally, e.g., intravenously, subcutaneously, intradermally, or intramuscularly. Thus, the invention provides compositions for parenteral administration which comprise a solution of the appropriate nucleic acids dissolved or suspended in an acceptable carrier, preferably an aqueous carrier.

Analytical compositions typically include a H37 nucleic acid molecule designed for use as a probe such as a PCR primer in a method used to monitor H37 in a cell as well as H37 antisense molecules designed to modulate H37 activity. Other specifically contemplated nucleic acid related embodiments of the invention disclosed herein are genomic DNA, cDNAs, ribozymes, and antisense molecules, as well as nucleic acid molecules based on an alternative backbone, or including alternative bases, whether derived from natural sources or synthesized, and include molecules capable of inhibiting the RNA or protein expression of H37. For example, antisense molecules can be RNAs or other molecules, including peptide nucleic acids (PNAs) or non-nucleic acid molecules such as phosphorothioate derivatives, that specifically bind DNA or RNA in a base pair-dependent manner. A skilled artisan can readily obtain these classes of nucleic acid molecules using the H37 polynucleotides and polynucleotide sequences disclosed herein.

Antisense technology entails the administration of exogenous oligonucleotides that bind to a target polynucleotide located within the cells. The term "antisense" refers to the fact that such oligonucleotides are complementary to their intracellular targets, e.g., H37. See for example, Jack Cohen, Oligodeoxynucleotides, Antisense Inhibitors of Gene Expression, CRC Press, 1989; and Synthesis 1:1–5 (1988). The H37 antisense oligonucleotides of the present invention include derivatives such as S-oligonucleotides (phosphorothioate derivatives or S-oligos, see, Jack Cohen, supra), which exhibit enhanced cancer cell growth inhibitory action. S-oligos (nucleoside phosphorothioates) are isoelectronic analogs of an oligonucleotide (O-oligo) in which a nonbridging oxygen atom of the phosphate group is replaced by a sulfur atom. The S-oligos of the present invention can be prepared by treatment of the corresponding O-oligos with 3H-1,2-benzodithiol-3-one-1,1-dioxide, which is a sulfur transfer reagent. See Iyer, R. P. et al, J. Org. Chem. 55:4693–4698 (1990); and Iyer, R. P. et al., J. Am. Chem. Soc. 112:1253–1254 (1990). Additional H37 antisense oligonucleotides of the present invention include morpholino antisense oligonucleotides known in the art (see, e.g., Partridge et al., 1996, Antisense & Nucleic Acid Drug Development 6:169–175).

The H37 antisense oligonucleotides of the present invention typically can be RNA or DNA that is complementary to and stably hybridizes with the first 100 5' codons or last 100 3' codons of the H37 genomic sequence or the corresponding mRNA. Absolute complementarity is not required, although high degrees of complementarity are preferred. Use of an oligonucleotide complementary to this region allows for the selective hybridization to H37 mRNA and not to mRNA specifying other regulatory subunits of protein kinase. In one embodiment, H37 antisense oligonucleotides of the present invention are 15 to 30-mer fragments of the antisense DNA molecule that have a sequence that hybridizes to H37 mRNA. Optionally, H37 antisense oligonucleotide is a 30-mer oligonucleotide that is complementary to a region in the first 10 5'-codons or last 10 3' codons of H37. Alternatively, the antisense molecules are modified to employ ribozymes in the inhibition of H37 expression, see, e.g., L. A. Couture & D. T. Stinchcomb; *Trends Genet* 12: 510–515 (1996).

The compositions of the invention have a number of embodiments. One embodiment includes a composition comprising an isolated H37 polynucleotide that encodes the amino acid sequence shown in SEQ ID NO: 2. A preferred embodiment includes a pharmaceutical composition comprising an effective amount of that encodes the H37 amino acid sequence shown in SEQ ID NO: 1 in admixture with a pharmaceutically acceptable carrier. Yet another embodiment of the invention is a composition comprising an antisense H37 polynucleotide which hybridizes to H37 mRNA in a mammalian cell such that the growth of the cell is modulated, wherein the polynucleotide hybridizes to a complement of the H37 polynucleotide shown in SEQ ID NO: 1 under stringent conditions.

Another embodiment of the invention is a composition comprising an isolated H37 polypeptide having the amino acid sequence shown in SEQ ID NO: 2. A related embodiment of the invention is a pharmaceutical composition comprising an effective amount of H37 polypeptide in admixture with a pharmaceutically acceptable carrier. In this context, "effective" means capable of modulating the growth of at least one mammalian cell.

IV. Kits

For use in the diagnostic and therapeutic applications described or suggested above, kits are also provided by the invention. Such kits may comprise a carrier means being compartmentalized to receive in close confinement one or more container means such as vials, tubes, and the like, each of the container means comprising one of the separate elements to be used in the method. For example, one of the container means may comprise a probe that is or can be detectably labeled. Such probe may be an antibody or polynucleotide specific for a H37 protein or a H37 gene or message, respectively. Alternatively, the one of the container means may comprise an expression vector for transducing a target cell. Where the kit utilizes nucleic acid hybridization to detect the target nucleic acid, the kit may also have containers containing nucleotide(s) for amplification of the target nucleic acid sequence and/or a container comprising a reporter-means, such as a biotin-binding protein, such as avidin or streptavidin, bound to a reporter molecule, such as an enzymatic, florescent, or radioisotope label.

The kit of the invention will typically comprise the container described above and one or more other containers comprising materials desirable from a commercial and user standpoint, including buffers, diluents, filters, needles, syringes, and package inserts with instructions for use. A label may be present on the container to indicate that the composition is used for a specific therapy or non-therapeutic application, and may also indicate directions for either in vivo or in vitro use, such as those described above.

The kits of the invention have a number of embodiments. A typical embodiment is a kit comprising a container, a label on said container, and a composition contained within said container; wherein the composition includes a polynucleotide that hybridizes to a complement of the H37 polynucleotide shown in SEQ ID NO: 1 under stringent conditions, the label on said container indicates that the composition can be used to evaluate the presence of H37 in at least one type of mammalian cell, and instructions for using the H37 polynucleotide for evaluating the presence of H37 RNA or DNA in at least one type of mammalian cell.

EXAMPLES

Various aspects of the invention are further described and illustrated by way of the several examples that follow, none of which are intended to limit the scope of the invention.

Example 1

Materials and Methods

Cell Culture

Cells (N4CF-7 human breast cancer cells, HBL-100 human breast cells, CaOv-3 human ovarian cancer cells, Calu-6 human lung cancer cells, A9 mouse fibrosarcoma cells, and NCI H740 human lung cancer cells) were obtained from ATCC (American Type Culture Collection). Cells were cultured in RPMI medium 1640, supplemented with 10% fetal bovine serum, 2 mM glutamine, and 1% penicillin G-streptomycin-fungizone solution.

Generation of the H37 Expression Vector

The full-length H37 cDNA (nucleotides 1–3091 as shown in FIG. 1) was subcloned in the pBK-CMV eukaryotic expression vector (Stratagene) in our differential cloning experiment using MCF-7/HER-2 cDNA library (Nucleic Acids Res. Oct. 15, 1999; 27(20):4008–17). The gene is transcribed via a CM7 immediate early promoter.

In Vitro Translation of the H37 Gene

Prior to transfection, in vitro translation experiment was performed to confirm that the cloned H37 cDNA makes the protein product of the expected size. The cDNA insert was translated into polypeptides in a TNT coupled reticulocyte system (Promega) according to the manufacturer's protocol.

Gene Transfection

1. Adherent Cells

For MCF-7 (human breast cancer cells), CaOv-3 (human ovarian cancer cells), Calu-6 (human lung cancer cells) and A9 (mouse fibrosarcoma cells), the H37 gene was transfected into cells by lipofectamine (Life Technologies, Inc.) according to the manufacturer's protocol. Cells were selected in medium containing geneticin (G418) at the concentration of 600 µg/ml (MCF-7), 500 µg/ml (CaOv-3), 300 µg/ml (Calu-6), and 300 µg/ml (A9), respectively. Even after the 2 week initial selection, the transfected cells were strictly maintained in the same concentration of the G418 to avoid reversion of the cells. As a control, cells were also transfected with the empty vector pBK-CMV.

2. Suspension Cells

For NCI H740 cells, the H37 gene was transfected in DMRIE-C (Life Technologies) according to the manufacturer's protocol. Cell lumps were dissociated to single cells in 0.1% pluronic solution (GIBCO.BRL) prior to transfection. The transfected cells were selected in geneticin at 100 µg/ml concentration for up to a month after which the antibiotic was removed. As a control, cells were also transfected with empty vector described above.

Northern Blot Analysis

The transfected cells were tested for the H37 mRNA expression level by Northern blot analysis. Total RNAs were isolated from each cell line with Trizol Reagent (GIBCO-BRL) according to the manufacturer's protocol. Twenty-five µg of total RNA was loaded onto a 1% formaldehyde-agarose gel and electrophoresed at 70 V for 4 h. The RNA was transferred to a nylon membrane in 10×SSC. The purified H37 cDNA insert was random labeled in a 50 µl reaction mix which contained 50 ng template, [γ-$^{32}$P]dCTP, 20 µg BSA, and 6 U Klenow. Incorporated counts were eluted from a G-50 Sephadex spin column (Pharmacia). Approximately 3×10$^6$ d.p.m./ml hybridization solution were used. The hybridization was carried out in 50% formamide, 2×SSC, 0.1% SDS, 10 mg/ml salmon sperm DNA, and 10% dextran sulfate, at 42° C. for 16 h. Membranes were washed in 2×SSC, 0.1% SDS at 25° C. for 10 min (three times), and in the same solution at 65° C. for 5 min (twice). The washed membranes were exposed with an intensifying screen to Kodak-XAR film at −70° C.

Single-Cell-Clonal Expansion (A9 Cells)

The A9 cells were transfected with the pBK-CMV H37 cDNA vector described above (adherent cells). Upon selection in G418 for 2 weeks, cells were plated into 10 cm dishes at a very low density and individual colonies were selected by use of cloning rings and expanded. Total RNA was extracted from each expanded cell line to determine the mRNA expression level. During the selection and expansion, all the transfected cells were strictly maintained in G418.

In Vitro Proliferation Assay

For MCF-7 and CaOv-3 cells, pools of transfected cells, both vector control and H37 transfectant populations, were examined immediately following two week selection in G418. For A9 cells, after 2 week selection in G418, single-cell-clonal populations were generated (see below), and selected high-expression clones were used for the assays. Throughout the proliferation assays, all the cells were strictly maintained in G418 of the proper concentrations to avoid vector loop-out.

1. Cell Counting

Cells were plated triplicate either in 60 mm dish (104 cells in 4 ml media per dish) for MCF-7 and CaOv-3 cells or in 6 well plate (5000 cells in 2 ml media per well) for A9 cells. After plating (day 0), seeding density was measured at day 1, and cells were counted at day 4, 7, and 11 by Coulter cell counter.

2. Soft Agar Colony Assay

Cells were plated in 0.4% (bottom) and 0.2% (top) soft agar layers containing G418 at above-mentioned concentration for each cell line. Cells were plated triplicate in 60 mm dishes (2×10$^4$ cells per dish) for MCF-7 cells (mass transfection), in 12 well plates (4000 cells per well) for CaOv-3 cells (mass transfection), and in 35 mm dishes (4000 cells per dish) for A9 single cell expanded clones. Cells were incubated at 37° C. for up to three weeks before colonies were stained in Tetrazolium dye for counting and photograph.

Animal Experiments—A9 Tumor Growth on Nude Mice

Approximately one month old nude mice were obtained from Charles River Laboratories. Mice were quarantined for two weeks prior to tumor cell injections. 1×10$^6$ cells were injected subcutaneously into mid-back region of mice (10 mice per each group). Tumor growth was observed and measured twice a week.

Example 2

Suppression of Tumor Cell Growth

In order to prove that the growth suppressions observed upon the H37 gene transfection were not merely transfection artifacts, the A9 (mouse fibrosarcoma) cells containing the recombinant H37 gene along with the several other genes were also transfected (i.e. other novel genes found in our differential screening which have been ful-length cloned and translated into protein products in vitro in a manner analogous to the H37 construct) (Nucleic Acids Res. Oct. 15, 1999;27(20):4008–17).

Cells were seeded in 6 well plates, 10$^5$ cells per well (triplicate for each plasmid). The next day, 1.5 µg of respective plasmid (H13, H17, H37, C40, H41 and pBK-CMV vector for control) was transfected into cells by lipofectamine (Life Technologies, Inc.) in Opti-memI serum-free media (Life Technologies, Inc.). After 5 hours, the transfection media was replaced with regular RPMI media. After 72 hours, G418 antibiotic was added in concentration of 300 µg/ml for selection for one week by which time all of non-transfected parental A9 cells were killed. The surviving cells were counted in Coulter cell counter.

Figure 13:
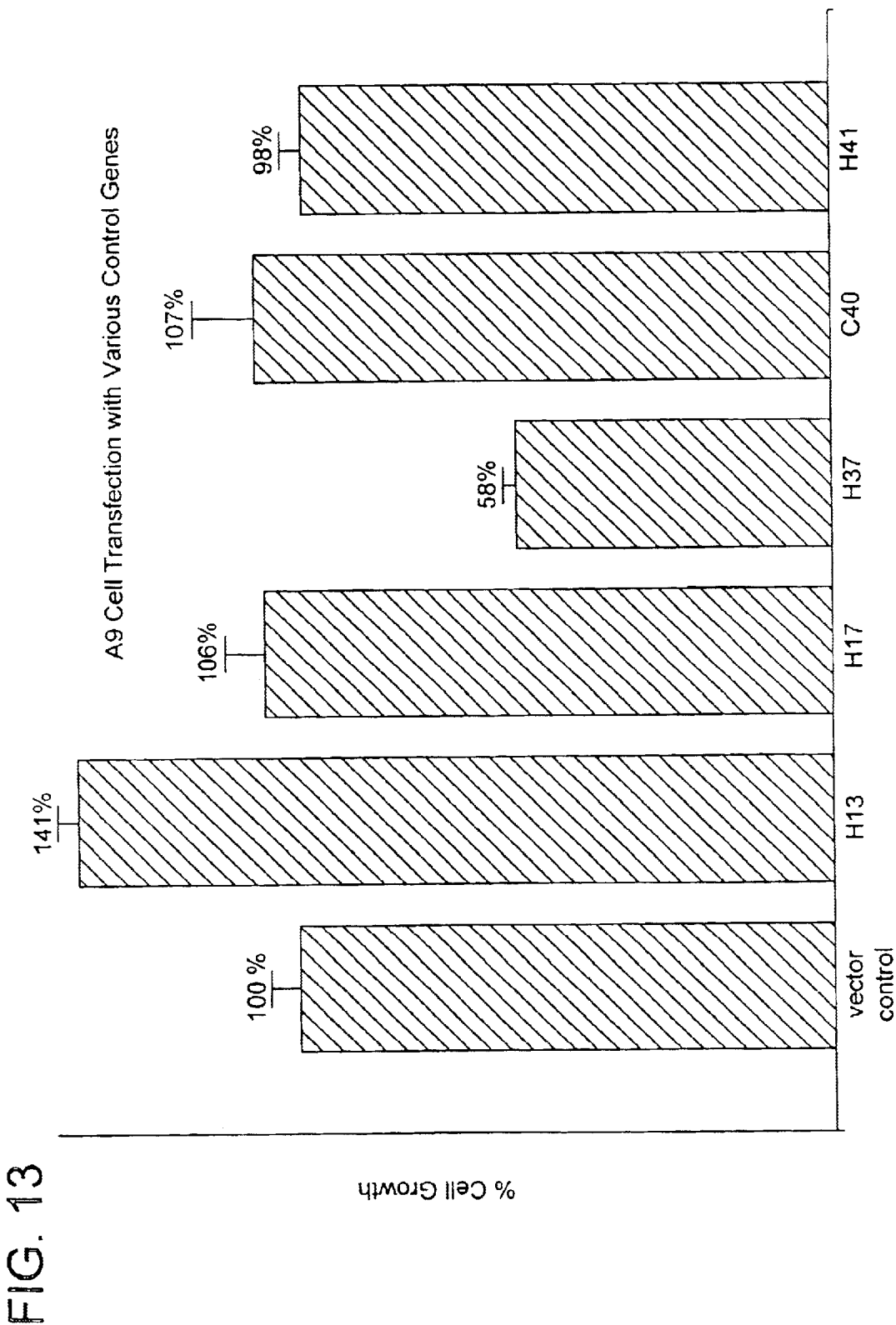
FIG. 13 is a bar graph showing the growth of A9 cells transfected with H37 and a series of control genes that are described in Oh et al. Nucleic Acids Res. Oct. 15, 1999; 27(20):4008–17. The numbers above the bars indicate % cell growth of each transfectant compared with the control transfectant.
Figure 14:
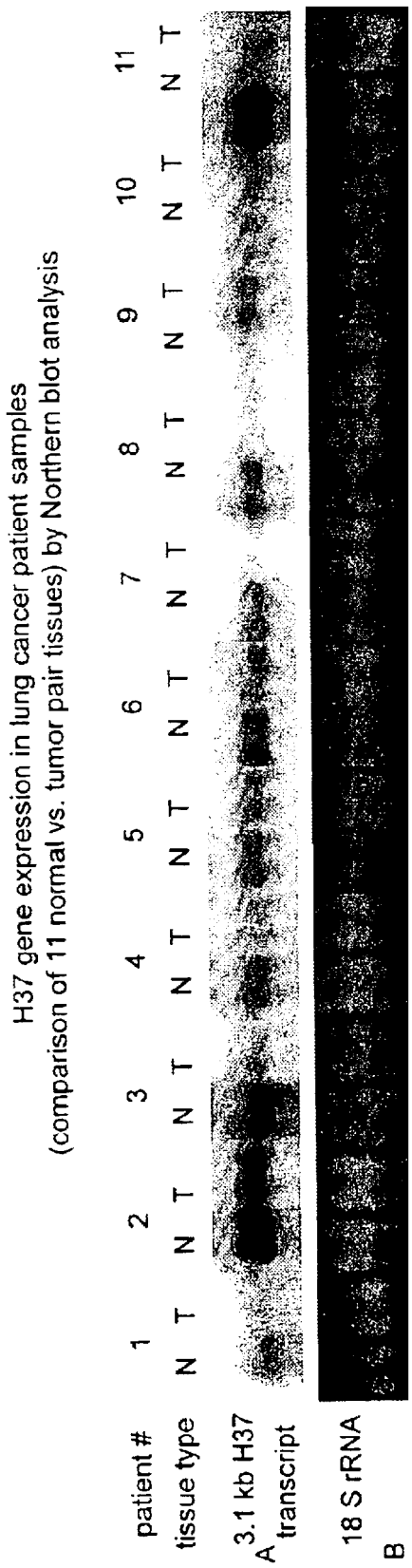
FIGS. 14A and 14B are a Northern blot analysis showing the expression of H37 in patient lung cancer samples (A=autoradiogram, B=gel loading control.

As shown in FIG. 13, only the H37 gene suppressed A9 cell growth (by 58% of vector control), the other genes either did not affect (i.e. H17, C40, H41) or increased cell growth (i.e. H13). As other genes transfected in parallel with H37 did not show the same growth suppressive effect provides evidence that the growth suppression observed upon H37 gene transfection is specific to the H37 gene and is not the result of some sort of transfection artifact occurring non-specifically in our experimental system.

In addition, we performed soft agar assay with MCF-7 cells transfected with various plasmid above in order to prove that H37 suppression of MCF-7 cells in soft agar is specific to the gene. Similarly we have not found any evidence for growth suppression in soft agar induced by "other" genes in our assay system.

We performed additional experiments in order to address the possibility that the growth suppression caused by the H37 gene may be due to this gene product being toxic to the cells and not a true biological suppression of the gene, i.e. the overexpression of exogenous protein is just killing the cells. In particular, we examined H37 transfected HBL-100 human breast cells which are immortalized but not transformed, and thus share characteristics that are very similar to the characteristics of normal breast cells (and have characteristics that are district from malignant cancer cells). We found that the H37 gene transfection does "not" suppress growth of this cell line. This provides evidence that the H37 gene may have a greater role in suppressing tumor growth in later stage of cancer development (more aggressive cancer) than in the early stages of growth disregulation. Moreover, this experimental data provides evidence that the H37 gene product is not being just toxic to cells but indeed biologically suppresses aggressive cancer cell growth.

In Vivo Experiments

A9 cells with or without the recombinant H37 gene were injected into nude mice and tumor growth in vivo was examined. These studies show that the H37 gene suppresses the growth of the mouse fibrosarcoma cells in mice (FIG. 12). The design and rationale for this in vivo experiment was based on the observation of Killary et al. in 1992 (PNAS, USA. 89:10877–10881) entitled "Definition of tumor suppressor locus within human chromosome 3p21–p22". This study was the first demonstration which provided direct "functional" (rather than cytogenetic) proof that the locus indeed contains a tumor suppressor gene(s). In the Killary experiment, suppression of the in vivo growth of A9 (mouse fibrosarcoma) cells in nude mice was accomplished by transfecting a 2-megabase piece of human chromosome encompassing 3p21–p22. Then, our in vivo experiment was to support the concept that the H37 gene, which is contained within that 2-megabase chromosome, is the gene responsible for this suppression. In support of our hypothesis, we were able to reproduce Killary's experiment by transfecting a single gene, H37, into the same cell line. This data provides direct "functional" proof that H37 is the tumor suppressor gene sought after for years by lung cancer researchers. Since this gene has a tumor suppressive activity, it has a good potential to have important medical (commercial) values if developed into gene therapy (i.e. in a fashion analogous to the p53 gene).

Example 3

H37 Gene Expression in Lung Cancer Patient Samples (Comparison of 11 Normal vs. Tumor Pair Tissues) by Northern Blot Analysis As shown in FIG. 9, differences in transcription level of the H37 tumor suppressor gene in the cancer vs. adjacent normal tissue pairs in primary lung cancer patients were examined via Northern analysis (N=normal, T=tumor).

Twenty µg each of total RNAs (obtained from 11 non-small cell lung cancer patients) was electrophoresed in formaldehyde gel, transferred to nylon membrane, and hybridized with random-primed, $^{32}$P-labeled H37 cDNA probe.

As expected from the previous observation that LOH (Loss of Heterozygosity) at chromosomal 3p21–22 occurs in >90% of non-small cell lung cancer cells, we found that 9 out of 11 samples (82%, i.e. patients #1, 2, 3, 4, 5, 6, 7, 8, 11) showed H37 gene expression level decrease in the tumor tissue as compared to the (normal) level in their normal tissue counterpart. This data provides evidence that an alteration (in this case a reduction) of H37 gene expression is involved in the oncogenesis.

Example 4

Generation of Polyclonal Antibodies Recognizing H37 Protein

Generally, polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. Typically a peptide can be designed from a coding region of H37. The peptide can be conjugated to keyhole limpet hemocyanin (KLH) and used to immunize a rabbit. Alternatively the immunizing agent may include all or portions of the H37 protein, or fusion proteins thereof For example, the H37 amino acid sequence can be fused to any one of a variety of known fusion protein partners that are well known in the art such as maltose binding protein, LacZ, thioredoxin or an immunoglobulin constant region (see e.g. *Current Protocols In Molecular Biology*, Volume 2, Unit 16, Frederick M. Ausubul et al. eds., 1995; Linsley, P. S., Brady, W., Urnes, M., Grosmaire, L., Damle, N., and Ledbetter, L.(1991) *J. Exp. Med.* 174, 561–566).

It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate).

The specific scheme we used to generate H37 antisera is shown in FIG. 15. As shown in FIG. 15A, polyclonal antibodies generated against either the recombinant protein or the peptide. For the recombinant proteins, the two bacterial MBP (maltose binding protein) fusion proteins were produced using the pMAL-c2 (NEB) vector containing H37 cDNA a.a. 408–815 (c-terminal half of the protein) or a.a. 571–815 (c-terminal ⅓ of the protein). After IPTG induction, 801-K cells (NEB) were collected by centrifugation, resuspended in Column buffer (20 mM Tris-HCl, 200 mM NaCl and 1 mM EDTA) containing 1 mM PMSF, and lysed by multiple freeze & thaw cycles and sonication. Cellular proteins were recovered in the supernatants after centrifugation at 9,000×g at 4° C. for 20 mm. The MBP-H37 fusion proteins were purified via amylose resin column and eluted in Column buffer containing 10 mM maltose. The fusion proteins were injected (subcutaneously) into rabbits using Freund's complete adjuvant for an initial round followed by multiple boosts using Freund's incomplete adjuvant. The polydonal "peptide" antibody was generated using 17-mer (a.a. 27–43 of SEQ ID NO: 2/ERESRSRRRDSDYKRSS) as an epitope.

As shown in FIG. 15B & C, both recombinant and peptide antibodies specifically recognize the 90 kDa H37 protein (in vitro-translated), but not the "luciferase" control (used for the translation reaction) nor a unrelated gene H13.

Confirmation of H37 Gene Expression at a Protein Level by Western Blot

Upon generation of the polyclonal antibodies, we wanted to demonstrate the H37 gene expression at the "protein" level in the cells which have been transfected with the H37 gene, and in the individual cell clones selected based on high expression level of H37 "mRNA" by Northern blot analysis.

A9 individual cell clones (either vector control or H37 transfected) were lysed in ripa buffer to obtain total cell extract. Approximately 40 μg each of lysate was electrophoresed in SDS-PAGE gel and transferred to PVDF membrane; the membrane was blocked in 3% milk solution, incubated with the primary antibody (polyclonal raised against c-terminal half of H37 protein, 1:700 dilution), and the secondary antibody (anti-rabbit IgG, Transduction laboratories). The bands were visualized using ECL Cheriluminescent Reagent (Amersham). This data illustrated a good correlation between H37 gene expression at the mRNA level and corresponding protein expression in individual transfectant cell clones.

Cellular Localization of the H37 Gene Product Into the Nucleus

Based on the functional/structural motifs present in the H37 protein (i.e. a bipartite nuclear signal, two zinc finger motifs, and two RNA binding motifs), it was speculated that the H37 protein may be located in the nucleus and have a DNA/RNA binding function. In order to elucidate cellular localization of H37 which may then suggest potential cellular functions of the protein, we utilized the generated polyclonal antibodies in immunohistochemical staining of cells.

A9 cells were cultured in 4-well chambered slides (Nunc) for 72 h, washed in PBS and fixed either in 4%/formaldehyde containing 0.1% Triton X-100 for 15 min. Endogenous peroxidase activity was quenched by treating with 3% $H_2O_2$ for 15 min. Cells were incubated in 10% normal goat serum and 0.05% saponin in PBS for 5 h to block non-specific binding and increase permeability. Primary antibodies (H37 polyclonal antibody raised against c-terminal half of the recombinant protein) and pre-immune serum were diluted (1:2000) in blocking solution and incubated with the slides overnight at 4° C. in a humidified chamber. The cells were incubated with goat anti-rabbit secondary antibodies (1:75; Zymed) for 30 min. followed by rabbit peroxidase anti-peroxidase complexes (PAP; 1:75; zymed) for 30 min. Antibody complexes were visualized by DAB (3,3'diaminobenzidine) chromagen (Sigma).

As shown in FIG. 17, the H37 antibody stains mainly nucleus as compared to its pre-immune counterpart which lacks staining. It may be inferred that H37 is functioning in the nucleus as a transcription factor inhibiting expression of a series of genes important in cell proliferation. There are many other tumor suppressor genes in this category, i.e. p53, RB, BRCA1.

Example 5

Reduction of H37 Protein Expression in Primary Non-Small Cell Lung Cancer (NSCLC) Tissues Materials & Methods Tumor Specimens and Immunohistochemical Staining Based on the observation that H37 mRNA level is reduced in lung cancer compared with adjacent normal tissues, we H37 protein expression in NSCLC was investigated by the immunohistological method. Fifty-five primary NSCLC tumors were obtained from patients undergoing surgical resection at UCLA medical center from 1995 to 2000. Specimens containing both tumor and adjacent normal tissues were fixed in formalin and embedded in paraffin block. Four μm thick sections cut from blocks were baked, deparaffinized in xylene, and rehydrated through a series of ethanol. Antigen retrieval was performed by incubating the sections at 100° C. in 10 mM sodium citrate buffer (pH 6.0) for 20 min. Endogenous peroxidase activity was quenched by treating with 3% hydrogen peroxide solution for 15 min. Slides were incubated with 2% BSA to block nonspecific antibody binding and then reacted with the primary rabbit polyclonal anti-H37 serum (1:2500 dilution) at 4° C. overnight. After washed in phosphate buffer saline (PBS), slides were incubated with the streptavidin-biotin-peroxidase complex (Dako). Sections were visualized by DAB (3,3'diaminobenzidine) chromagen (Dako). Normal rabbit IgG at the same concentration as the primary antibodies served as negative controls.

Of 62 tumors examined, 46 (73%) showed immunohistochemical H37 protein expression reduced compared with that of normal bronchial epithelial cells (See FIG. 18), whereas 16 (27%) showed similar H37 immunoreactivity between tumor and normal elements. As shown in Table I below, H37 expression was reduced in 82% of adenocarcinoma (32 of 39) and 65% of squamous cell carcinoma (11/17). Tumors with decreased immunoreactivity were further classed into "strongly reduced" vs. "moderately reduced" according to the degree of reduction (See Table I). In adenocarcinoma, the "strongly reduced" expression was observed most preferentially in poorly differentiated subtypes. In squamous cell carcinomas, not only less fraction of samples show reduced staining, but among the reduced tumors, less fraction of them showed "strongly reduced" pattern than adenocarcinoma. Six samples of large cell undifferentiated carcinoma were obtained for this study. Three of them showed strongly reduced immunoreactivity, but there was no difference between the normal and the tumor cells for the rest of samples. Overall, 73% of NSCLCs used in our study showed decrease in H37 immunoreactivity in tumor cells. These results shows that H37 protein expression is a useful marker for the diagnosis and/or prognosis of patients with cancers such as surgically resected NSCLC.

TABLE I

Reduced immunostaining of H37 according to histology and differentiation state of the 62 NSCLC studied

| | H37 expression | | |
|---|---|---|---|
| Histology/Differentiation | Reduced (— —/—)[a] | Not reduced | % reduced |
| Adenocarcinoma (n = 39) | 21/11 | 7 | 82 |
| Well (n = 4) | 2/2 | 0 | |
| Moderate (n = 9) | 5/3 | 1 | |
| Moderate to poor (n = 8) | 3/4 | 1 | |
| Poor(n = 18) | 11/2 | 5 | |
| Squamous cell carcinoma (n = 17) | 5/6 | 6 | 65 |
| Well (n = 4) | 3/0 | 1 | |
| Moderate (n = 3) | 0/1 | 2 | |
| Moderate to poor (n = 2) | 0/1 | 1 | |
| Poor (n = 8) | 2/4 | 2 | |
| Large cell carcinoma (n = 6) | 3/0 | 3 | 50 |
| Total (n = 62) | 29/17 | 16 | 73 |

[a] — —immunoreactivity in tumor is markedly reduced, i.e. more than about a three fold decrease by visualization;
—immunoreactivity in tumor is moderately reduced, i.e. less than about a three fold decrease.

Throughout this application, various publications are referenced. The disclosures of these publications are hereby incorporated by reference herein in their entireties.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

What is claimed is:

1. A method of examining a test biological sample comprising a human breast, ovarian or lung cell for evidence of altered cell growth that is indicative of a breast, ovarian or lung cancer, the method comprising evaluating levels of H37 polynucleotides that encode the H37 polypeptide shown in SEQ ID NO: 2 in a test biological sample, wherein a decrease in the levels of said H37 polynucleotides in the test biological sample relative to a normal tissue sample provide evidence of altered cell growth that is indicative of a breast, ovarian or lung cancer; and wherein the levels of said H37 polynucleotides in a sample are evaluated by contacting the sample with a polynucleotide probe that specifically hybridizes to a H37 nucleotide sequence shown in SEQ ID NO: 1 and evaluating the presence of a hybridization complex formed by the hybridization of the polynucleotide probe with said H37 polynucleotides in the sample.

2. The method of claim 1, wherein the presence of a hybridization complex is evaluated by Northern analysis.

3. The method of claim 1, wherein the presence of a hybridization complex is evaluated by polymerase chain reaction.

4. The method of claim 1, wherein the H37 polynucleotides in the test sample are mRNA.

5. The method of claim 1, wherein a decrease in the levels of H37 polynucleotides in the test sample relative to a normal tissue sample provide evidence of lung cancer.

6. A method of examining a test biological sample comprising a human breast, ovarian or lung cell for evidence of altered cell growth that is indicative of a breast, ovarian or lung cancer, the method comprising evaluating levels of H37 polypeptides having the sequence shown in SEQ ID NO: 2 in a test biological sample, wherein a decrease in the levels of said H37 polypeptides in the test biological sample relative to a normal tissue sample provide evidence of altered cell growth that is indicative of a breast, ovarian or lung cancer; and wherein the levels of said H37 polypeptides in a sample are evaluated by contacting the sample with an antibody that immunospecifically binds to a H37 polypeptide sequence shown in SEQ ID NO: 2 and evaluating the presence of a complex formed by the binding of the antibody with said H37 polypeptides in the sample.

7. The method of claim 6, wherein the presence of a complex is evaluated by a method selected from the group consisting of ELISA analysis, Western analysis and immunohistochemistry.

8. The method of claim 6, wherein a decrease in the levels of H37 polypeptides in the test sample relative to a normal tissue sample provide evidence of cancer.

9. The method of claim 8, wherein a decrease in the levels of H37 polypeptides in the test sample relative to a normal tissue sample provide evidence of lung cancer.

* * * * *

SEQUENCE LISTING

<160> NUMBER OF SEQ ID NOS: 7

<210> SEQ ID NO 1
<211> LENGTH: 3094
<212> TYPE: DNA
<213> ORGANISM: Homo Sapiens
<220> FEATURE:
<221> NAME/KEY: CDS
<222> LOCATION: (127)...(2572)

<400> SEQUENCE: 1

```
ggcacgagcc gccgaacctt gttggaggtt ctggggcgca gaaccgctac tgctgcttcg      60
gtctctcctt gggaaaaaat aaaatttgaa ccttttggag ctgtgtgcta aatcttcagt     120 gggaca atg ggt tca gac aaa aga gtg agt aga aca gag cgt agt gga        168
       Met Gly Ser Asp Lys Arg Val Ser Arg Thr Glu Arg Ser Gly
         1               5                  10 aga tac ggt tcc atc ata gac agg gat gac cgt gat gag cgt gaa tcc       216
Arg Tyr Gly Ser Ile Ile Asp Arg Asp Asp Arg Asp Glu Arg Glu Ser
 15                  20                  25                  30 cga agc agg cgg agg gac tca gat tac aaa aga tct agt gat gat cgg       264
Arg Ser Arg Arg Arg Asp Ser Asp Tyr Lys Arg Ser Ser Asp Asp Arg
                 35                  40                  45 agg ggt gat aga tat gat gac tac cga gac tat gac agt cca gag aga       312
Arg Gly Asp Arg Tyr Asp Asp Tyr Arg Asp Tyr Asp Ser Pro Glu Arg
             50                  55                  60 gag cgt gaa aga agg aac agt gac cga tcc gaa gat ggc tac cat tca       360
Glu Arg Glu Arg Arg Asn Ser Asp Arg Ser Glu Asp Gly Tyr His Ser
         65                  70                  75 gat ggt gac tat ggt gag cac gac tat agg cat gac atc agt gac gag       408
Asp Gly Asp Tyr Gly Glu His Asp Tyr Arg His Asp Ile Ser Asp Glu
     80                  85                  90 agg gag agc aag acc atc atg ctg cgc ggc ctt ccc atc acc atc aca       456
Arg Glu Ser Lys Thr Ile Met Leu Arg Gly Leu Pro Ile Thr Ile Thr
 95                 100                 105                 110 gag agc gat att cga gaa atg atg gag tcc ttc gaa ggc cct cag cct       504
Glu Ser Asp Ile Arg Glu Met Met Glu Ser Phe Glu Gly Pro Gln Pro
                115                 120                 125 gcg gat gtg agg ctg atg aag agg aaa aca ggt gta agc cgt ggt ttc       552
Ala Asp Val Arg Leu Met Lys Arg Lys Thr Gly Val Ser Arg Gly Phe
            130                 135                 140 gcc ttc gtg gag ttt tat cac ttg caa gat gct acc agc tgg atg gaa       600
Ala Phe Val Glu Phe Tyr His Leu Gln Asp Ala Thr Ser Trp Met Glu
        145                 150                 155 gcc aat cag aaa aag ttg gtg att caa gga aag cac att gca atg cat       648
Ala Asn Gln Lys Lys Leu Val Ile Gln Gly Lys His Ile Ala Met His
    160                 165                 170 tat agc aat ccc aga cct aag ttt gaa gat tgg ctt tgt aac aag tgc       696
Tyr Ser Asn Pro Arg Pro Lys Phe Glu Asp Trp Leu Cys Asn Lys Cys
175                 180                 185                 190 tgc ctt aac aat ttc agg aaa aga cta aaa tgc ttc cga tgt gga gca       744
Cys Leu Asn Asn Phe Arg Lys Arg Leu Lys Cys Phe Arg Cys Gly Ala
                195                 200                 205 gac aag ttt gac tct gaa cag gaa gtg cct cct gga acc aca gag tcg       792
Asp Lys Phe Asp Ser Glu Gln Glu Val Pro Pro Gly Thr Thr Glu Ser
            210                 215                 220 gtt cag tct gtg gat tac tac tgt gat acg atc att ctt cgg aac ata       840
Val Gln Ser Val Asp Tyr Tyr Cys Asp Thr Ile Ile Leu Arg Asn Ile
        225                 230                 235
```

-continued

```
gct ccg cac act gtg gtg gat tcc atc atg aca gca ctg tct cct tac      888
Ala Pro His Thr Val Val Asp Ser Ile Met Thr Ala Leu Ser Pro Tyr
240                 245                 250 gcg tct tta gct gtc aat aac atc cgc ctc ata aaa gac aaa cag acc      936
Ala Ser Leu Ala Val Asn Asn Ile Arg Leu Ile Lys Asp Lys Gln Thr
255                 260                 265                 270 cag cag aac aga ggc ttc gca ttt gtg cag ctg tcc tct gca atg gat      984
Gln Gln Asn Arg Gly Phe Ala Phe Val Gln Leu Ser Ser Ala Met Asp
                275                 280                 285 gct tct cag ctg ctt cag ata tta cag agt ctc cat cct cct ttg aaa     1032
Ala Ser Gln Leu Leu Gln Ile Leu Gln Ser Leu His Pro Pro Leu Lys
            290                 295                 300 att gat ggc aaa act att ggg gtt gat ttt gca aaa agt gcc aga aaa     1080
Ile Asp Gly Lys Thr Ile Gly Val Asp Phe Ala Lys Ser Ala Arg Lys
        305                 310                 315 gac ttg gtc ctc tca gat ggt aac cgc gtc agc gcc ttc tct gta gct     1128
Asp Leu Val Leu Ser Asp Gly Asn Arg Val Ser Ala Phe Ser Val Ala
320                 325                 330 agt acg gct att gct gct gct cag tgg tca tcc acc cag tct caa agt     1176
Ser Thr Ala Ile Ala Ala Ala Gln Trp Ser Ser Thr Gln Ser Gln Ser
335                 340                 345                 350 ggt gaa gga ggc agt gtt gac tac agt tat ctg caa cca ggt caa gat     1224
Gly Glu Gly Gly Ser Val Asp Tyr Ser Tyr Leu Gln Pro Gly Gln Asp
                355                 360                 365 ggc tat gcc caa tat gct cag tat tca cag gat tat cag cag ttt tat     1272
Gly Tyr Ala Gln Tyr Ala Gln Tyr Ser Gln Asp Tyr Gln Gln Phe Tyr
            370                 375                 380 caa caa caa gct gga gga ttg gaa tct gat gca tca tct gca tca ggc     1320
Gln Gln Gln Ala Gly Gly Leu Glu Ser Asp Ala Ser Ser Ala Ser Gly
        385                 390                 395 aca gca gtg acc acc acc tca gcg gct gta gtg tcc cag agt cct cag     1368
Thr Ala Val Thr Thr Thr Ser Ala Ala Val Val Ser Gln Ser Pro Gln
400                 405                 410 ctg tat aat caa acc tcc aat cca cct ggc tct ccg act gag gaa gca     1416
Leu Tyr Asn Gln Thr Ser Asn Pro Pro Gly Ser Pro Thr Glu Glu Ala
415                 420                 425                 430 cag cct agc act agc aca agt aca cag gcc cca gcc gct tcc cct act     1464
Gln Pro Ser Thr Ser Thr Ser Thr Gln Ala Pro Ala Ala Ser Pro Thr
                435                 440                 445 ggt gta gtt cct ggt acc aaa tat gca gta cct gac acg tcc act tac     1512
Gly Val Val Pro Gly Thr Lys Tyr Ala Val Pro Asp Thr Ser Thr Tyr
            450                 455                 460 cag tat gat gaa tct tca gga tat tac tat gat ccg aca aca ggg ctc     1560
Gln Tyr Asp Glu Ser Ser Gly Tyr Tyr Tyr Asp Pro Thr Thr Gly Leu
        465                 470                 475 tat tat gac ccc aac tcg caa tac tac tat aat tcc ttg acc cag cag     1608
Tyr Tyr Asp Pro Asn Ser Gln Tyr Tyr Tyr Asn Ser Leu Thr Gln Gln
480                 485                 490 tac ctt tac tgg gat ggg gaa aaa gag acc tac gtg cca gct gca gag     1656
Tyr Leu Tyr Trp Asp Gly Glu Lys Glu Thr Tyr Val Pro Ala Ala Glu
495                 500                 505                 510 tct agc tcc cac cag cag tcg ggc ctg cct cct gca aaa gag ggg aaa     1704
Ser Ser Ser His Gln Gln Ser Gly Leu Pro Pro Ala Lys Glu Gly Lys
                515                 520                 525 gag aag aag gag aaa ccc aag agc aaa aca gcc cag cag att gcc aaa     1752
Glu Lys Lys Glu Lys Pro Lys Ser Lys Thr Ala Gln Gln Ile Ala Lys
            530                 535                 540 gac atg gaa cgc tgg gct aag agt ttg aat aag cag aaa gaa aac ttt     1800
Asp Met Glu Arg Trp Ala Lys Ser Leu Asn Lys Gln Lys Glu Asn Phe
        545                 550                 555
```

```
aaa aat agc ttt cag cct gtc aat tcc ttg agg gaa gaa gaa agg aga    1848
Lys Asn Ser Phe Gln Pro Val Asn Ser Leu Arg Glu Glu Glu Arg Arg
        560                 565                 570 gaa tct gct gca gca gac gct ggc ttt gct ctc ttt gag aag aag gga    1896
Glu Ser Ala Ala Ala Asp Ala Gly Phe Ala Leu Phe Glu Lys Lys Gly
575                 580                 585                 590 gcc tta gct gaa agg cag cag ctc atc cca gaa ttg gtg cga aat gga    1944
Ala Leu Ala Glu Arg Gln Gln Leu Ile Pro Glu Leu Val Arg Asn Gly
                595                 600                 605 gat gag gag aat ccc ctc aaa agg ggt ctg gtt gct gct tac agt ggt    1992
Asp Glu Glu Asn Pro Leu Lys Arg Gly Leu Val Ala Ala Tyr Ser Gly
            610                 615                 620 gac agt gac aat gag gag gag ctg gtg gag aga ctt gag agt gag gaa    2040
Asp Ser Asp Asn Glu Glu Glu Leu Val Glu Arg Leu Glu Ser Glu Glu
        625                 630                 635 gag aag cta gct gac tgg aag aag atg gcc tgt ctg ctc tgc cgg cgc    2088
Glu Lys Leu Ala Asp Trp Lys Lys Met Ala Cys Leu Leu Cys Arg Arg
    640                 645                 650 cag ttc ccg aac aaa gat gcc cta gtc agg cac cag caa ctc tca gac    2136
Gln Phe Pro Asn Lys Asp Ala Leu Val Arg His Gln Gln Leu Ser Asp
655                 660                 665                 670 ctt cac aag caa aac atg gac atc tac cga cga tcc agg ctg agc gag    2184
Leu His Lys Gln Asn Met Asp Ile Tyr Arg Arg Ser Arg Leu Ser Glu
                675                 680                 685 cag gag ctg gaa gcc ttg gag cta agg gag aga gag atg aaa tac cga    2232
Gln Glu Leu Glu Ala Leu Glu Leu Arg Glu Arg Glu Met Lys Tyr Arg
            690                 695                 700 gac cga gct gca gaa aga cgg gag aag tac ggc att cca gaa cct cca    2280
Asp Arg Ala Ala Glu Arg Arg Glu Lys Tyr Gly Ile Pro Glu Pro Pro
        705                 710                 715 gag ccc aag cgc aag aag cag ttt gat gcc ggc act gtg aat tac gag    2328
Glu Pro Lys Arg Lys Lys Gln Phe Asp Ala Gly Thr Val Asn Tyr Glu
720                 725                 730 caa ccc acc aaa gat ggc att gac cac agt aac att ggc aac aag atg    2376
Gln Pro Thr Lys Asp Gly Ile Asp His Ser Asn Ile Gly Asn Lys Met
735                 740                 745                 750 ctg cag gcc atg ggc tgg cgg gaa ggc tct ggc ttg gga cga aag tgt    2424
Leu Gln Ala Met Gly Trp Arg Glu Gly Ser Gly Leu Gly Arg Lys Cys
                755                 760                 765 caa ggc att acg gct ccc att gag gct caa gtt cgg cta aag gga gct    2472
Gln Gly Ile Thr Ala Pro Ile Glu Ala Gln Val Arg Leu Lys Gly Ala
            770                 775                 780 ggc cta gga gcc aaa ggc agc gca tat ggt ttg tcg ggc gcc gat tcc    2520
Gly Leu Gly Ala Lys Gly Ser Ala Tyr Gly Leu Ser Gly Ala Asp Ser
        785                 790                 795 tac aaa gat gct gtc cgg aaa gcc atg ttt gcc cgg ttc act gag atg    2568
Tyr Lys Asp Ala Val Arg Lys Ala Met Phe Ala Arg Phe Thr Glu Met
800                 805                 810 gag t gagagagaga gagagagaga gatgacaagg agcacaagaa gtggtccatc       2622
Glu
815 tcccgaattc gctgttaccg cctgtctctt taagggcatg ccttgtgctg ttaatagatc  2682 ttagggtgaa ccacttcatt ctgcagggtt ctccctccca ccttaaagaa gttcccctta  2742 tgtgggttgc ctggtgaatg gccttccttc ccgccagagg gcttgtgaac agaccggaga  2802 ggacagtgga ttgtttatac tccagtgtac atagtgtaat gtagcgtgtt tacatgtgta  2862 gcctatgttg tggtccatca gcccctcaca ttcctagggg tttgagatgc tgtaggtggt  2922
```

```
atgtgacacc aaagccacct ctgtcatttg ttgtgatgtc tttttcttggc aaaaagccttg      2982 tgtatatttg tatattacac atttgtacag aattttggaa gattttcagt ctagttgcca      3042
aatctggctc ctttacaaaa gaaatacctt gagaaaaaaa aaaaaaaaaa aa              3094
```

<210> SEQ ID NO 2
<211> LENGTH: 815
<212> TYPE: PRT
<213> ORGANISM: Homo Sapiens

<400> SEQUENCE: 2

```
Met Gly Ser Asp Lys Arg Val Ser Arg Thr Glu Arg Ser Gly Arg Tyr
1               5                   10                  15

Gly Ser Ile Ile Asp Arg Asp Arg Asp Glu Arg Glu Ser Arg Ser
            20                  25                  30

Arg Arg Arg Asp Ser Asp Tyr Lys Arg Ser Ser Asp Asp Arg Arg Gly
        35                  40                  45

Asp Arg Tyr Asp Asp Tyr Arg Asp Tyr Asp Ser Pro Glu Arg Glu Arg
    50                  55                  60

Glu Arg Arg Asn Ser Asp Arg Ser Glu Asp Gly Tyr His Ser Asp Gly
65                  70                  75                  80

Asp Tyr Gly Glu His Asp Tyr Arg His Asp Ile Ser Asp Glu Arg Glu
                85                  90                  95

Ser Lys Thr Ile Met Leu Arg Gly Leu Pro Ile Thr Ile Thr Glu Ser
            100                 105                 110

Asp Ile Arg Glu Met Met Glu Ser Phe Glu Gly Pro Gln Pro Ala Asp
        115                 120                 125

Val Arg Leu Met Lys Arg Lys Thr Gly Val Ser Arg Gly Phe Ala Phe
    130                 135                 140

Val Glu Phe Tyr His Leu Gln Asp Ala Thr Ser Trp Met Glu Ala Asn
145                 150                 155                 160

Gln Lys Lys Leu Val Ile Gln Gly Lys His Ile Ala Met His Tyr Ser
                165                 170                 175

Asn Pro Arg Pro Lys Phe Glu Asp Trp Leu Cys Asn Lys Cys Cys Leu
            180                 185                 190

Asn Asn Phe Arg Lys Arg Leu Lys Cys Phe Arg Cys Gly Ala Asp Lys
        195                 200                 205

Phe Asp Ser Glu Gln Glu Val Pro Pro Gly Thr Thr Glu Ser Val Gln
    210                 215                 220

Ser Val Asp Tyr Tyr Cys Asp Thr Ile Ile Leu Arg Asn Ile Ala Pro
225                 230                 235                 240

His Thr Val Val Asp Ser Ile Met Thr Ala Leu Ser Pro Tyr Ala Ser
                245                 250                 255

Leu Ala Val Asn Asn Ile Arg Leu Ile Lys Asp Lys Gln Thr Gln Gln
            260                 265                 270

Asn Arg Gly Phe Ala Phe Val Gln Leu Ser Ser Ala Met Asp Ala Ser
        275                 280                 285

Gln Leu Leu Gln Ile Leu Gln Ser Leu His Pro Pro Leu Lys Ile Asp
    290                 295                 300

Gly Lys Thr Ile Gly Val Asp Phe Ala Lys Ser Ala Arg Lys Asp Leu
305                 310                 315                 320

Val Leu Ser Asp Gly Asn Arg Val Ser Ala Phe Ser Val Ala Ser Thr
                325                 330                 335

Ala Ile Ala Ala Ala Gln Trp Ser Ser Thr Gln Ser Gln Ser Gly Glu
            340                 345                 350
```

-continued

```
Gly Gly Ser Val Asp Tyr Ser Tyr Leu Gln Pro Gly Gln Asp Gly Tyr
        355                 360                 365
Ala Gln Tyr Ala Gln Tyr Ser Gln Asp Tyr Gln Gln Phe Tyr Gln Gln
        370                 375                 380
Gln Ala Gly Gly Leu Glu Ser Asp Ala Ser Ser Ala Ser Gly Thr Ala
385                 390                 395                 400
Val Thr Thr Thr Ser Ala Ala Val Val Ser Gln Ser Pro Gln Leu Tyr
                405                 410                 415
Asn Gln Thr Ser Asn Pro Pro Gly Ser Pro Thr Glu Glu Ala Gln Pro
            420                 425                 430
Ser Thr Ser Thr Ser Thr Gln Ala Pro Ala Ala Ser Pro Thr Gly Val
                435                 440                 445
Val Pro Gly Thr Lys Tyr Ala Val Pro Asp Thr Ser Thr Tyr Gln Tyr
        450                 455                 460
Asp Glu Ser Ser Gly Tyr Tyr Tyr Asp Pro Thr Thr Gly Leu Tyr Tyr
465                 470                 475                 480
Asp Pro Asn Ser Gln Tyr Tyr Tyr Asn Ser Leu Thr Gln Gln Tyr Leu
                485                 490                 495
Tyr Trp Asp Gly Glu Lys Glu Thr Tyr Val Pro Ala Ala Glu Ser Ser
                500                 505                 510
Ser His Gln Gln Ser Gly Leu Pro Pro Ala Lys Glu Gly Lys Glu Lys
                515                 520                 525
Lys Glu Lys Pro Lys Ser Lys Thr Ala Gln Gln Ile Ala Lys Asp Met
        530                 535                 540
Glu Arg Trp Ala Lys Ser Leu Asn Lys Gln Lys Glu Asn Phe Lys Asn
545                 550                 555                 560
Ser Phe Gln Pro Val Asn Ser Leu Arg Glu Glu Arg Arg Glu Ser
                565                 570                 575
Ala Ala Ala Asp Ala Gly Phe Ala Leu Phe Glu Lys Lys Gly Ala Leu
                580                 585                 590
Ala Glu Arg Gln Gln Leu Ile Pro Glu Leu Val Arg Asn Gly Asp Glu
        595                 600                 605
Glu Asn Pro Leu Lys Arg Gly Leu Val Ala Ala Tyr Ser Gly Asp Ser
610                 615                 620
Asp Asn Glu Glu Glu Leu Val Glu Arg Leu Glu Ser Glu Glu Glu Lys
625                 630                 635                 640
Leu Ala Asp Trp Lys Lys Met Ala Cys Leu Leu Cys Arg Arg Gln Phe
                645                 650                 655
Pro Asn Lys Asp Ala Leu Val Arg His Gln Gln Leu Ser Asp Leu His
            660                 665                 670
Lys Gln Asn Met Asp Ile Tyr Arg Arg Ser Arg Leu Ser Glu Gln Glu
        675                 680                 685
Leu Glu Ala Leu Glu Leu Arg Glu Arg Glu Met Lys Tyr Arg Asp Arg
        690                 695                 700
Ala Ala Glu Arg Arg Glu Lys Tyr Gly Ile Pro Glu Pro Pro Glu Pro
705                 710                 715                 720
Lys Arg Lys Lys Gln Phe Asp Ala Gly Thr Val Asn Tyr Glu Gln Pro
                725                 730                 735
Thr Lys Asp Gly Ile Asp His Ser Asn Ile Gly Asn Lys Met Leu Gln
            740                 745                 750
Ala Met Gly Trp Arg Glu Gly Ser Gly Leu Gly Arg Lys Cys Gln Gly
        755                 760                 765
```

```
Ile Thr Ala Pro Ile Glu Ala Gln Val Arg Leu Lys Gly Ala Gly Leu
    770             775                 780

Gly Ala Lys Gly Ser Ala Tyr Gly Leu Ser Gly Ala Asp Ser Tyr Lys
785             790                 795                 800

Asp Ala Val Arg Lys Ala Met Phe Ala Arg Phe Thr Glu Met Glu
                805                 810                 815

<210> SEQ ID NO 3
<211> LENGTH: 3094
<212> TYPE: DNA
<213> ORGANISM: Homo sapiens
<220> FEATURE:
<221> NAME/KEY: CDS
<222> LOCATION: (127)...(2572)

<400> SEQUENCE: 3
ggcacgagcc gccgaacctt gttggaggtt ctggggcgca gaaccgctac tgctgcttcg      60
gtctctcctt ggaaaaaat aaatttgaa cctttggag ctgtgtgcta atcttcagt         120 gggaca atg ggt tca gac aaa aga gtg agt aga aca gag cgt agt gga      168
       Met Gly Ser Asp Lys Arg Val Ser Arg Thr Glu Arg Ser Gly
       1               5                   10 aga tac ggt tcc atc ata gac agg gat gac cgt gat gag cgt gaa tcc   216
Arg Tyr Gly Ser Ile Ile Asp Arg Asp Asp Arg Asp Glu Arg Glu Ser
15              20                  25                  30 cga agc agg cgg agg gac tca gat tac aaa aga tct agt gat gat cgg   264
Arg Ser Arg Arg Arg Asp Ser Asp Tyr Lys Arg Ser Ser Asp Asp Arg
                35                  40                  45 agg ggt gat aga tat gat gac tac cga gac tat gac agt cca cag aga   312
Arg Gly Asp Arg Tyr Asp Asp Tyr Arg Asp Tyr Asp Ser Pro Gln Arg
            50                  55                  60 gag cgt gaa aga agg aac agt gac cga tcc gaa gat ggc tac cat tca   360
Glu Arg Glu Arg Arg Asn Ser Asp Arg Ser Glu Asp Gly Tyr His Ser
        65                  70                  75 gat ggt gac tat ggt gag cac gac tat agg cat gac atc agt gac gag   408
Asp Gly Asp Tyr Gly Glu His Asp Tyr Arg His Asp Ile Ser Asp Glu
    80                  85                  90 agg gag agc aag acc atc atg ctg cgc ggc ctt ccc atc acc atc aca   456
Arg Glu Ser Lys Thr Ile Met Leu Arg Gly Leu Pro Ile Thr Ile Thr
95              100                 105                 110 gag agc gat att cga gaa atg atg gag tcc ttc gaa ggc cct cag cct   504
Glu Ser Asp Ile Arg Glu Met Met Glu Ser Phe Glu Gly Pro Gln Pro
                115                 120                 125 gcg gat gtg agg ctg atg aag agg aaa aca ggt gta agc cgt ggt ttc   552
Ala Asp Val Arg Leu Met Lys Arg Lys Thr Gly Val Ser Arg Gly Phe
            130                 135                 140 gcc ttc gtg gag ttt tat cac ttg caa gat gct acc agc tgg atg gaa   600
Ala Phe Val Glu Phe Tyr His Leu Gln Asp Ala Thr Ser Trp Met Glu
        145                 150                 155 gcc aat cag aaa aag ttg gtg att caa gga aag cac att gca atg cat   648
Ala Asn Gln Lys Lys Leu Val Ile Gln Gly Lys His Ile Ala Met His
    160                 165                 170 tat agc aat ccc aga cct aag ttt gaa gat tgg ctt tgt aac aag tgc   696
Tyr Ser Asn Pro Arg Pro Lys Phe Glu Asp Trp Leu Cys Asn Lys Cys
175                 180                 185                 190 tgc ctt aac aat ttc agg aaa aga cta aaa tgc ttc cga tgt gga gca   744
Cys Leu Asn Asn Phe Arg Lys Arg Leu Lys Cys Phe Arg Cys Gly Ala
                195                 200                 205 gac aag ttt gac tct gaa cag gaa gtg cct cct gga acc aca gag tcg   792
Asp Lys Phe Asp Ser Glu Gln Glu Val Pro Pro Gly Thr Thr Glu Ser
            210                 215                 220
```

```
                                                    -continued gtt cag tct gtg gat tac tac tgt gat acg atc att ctt cgg aac ata         840
Val Gln Ser Val Asp Tyr Tyr Cys Asp Thr Ile Ile Leu Arg Asn Ile
        225                 230                 235 gct ccg cac act gtg gtg gat tcc atc atg aca gca ctg tct cct tac         888
Ala Pro His Thr Val Val Asp Ser Ile Met Thr Ala Leu Ser Pro Tyr
240                 245                 250 gcg tct tta gct gtc aat aac atc cgc ctc ata aaa gac aaa cag acc         936
Ala Ser Leu Ala Val Asn Asn Ile Arg Leu Ile Lys Asp Lys Gln Thr
255                 260                 265                 270 cag cag aac aga ggc ttc gca ttt gtg cag ctg tcc tct gca atg gat         984
Gln Gln Asn Arg Gly Phe Ala Phe Val Gln Leu Ser Ser Ala Met Asp
                275                 280                 285 gct tct cag ctg ctt cag ata tta cag agt ctc cat cct cct ttg aaa        1032
Ala Ser Gln Leu Leu Gln Ile Leu Gln Ser Leu His Pro Pro Leu Lys
        290                 295                 300 att gat ggc aaa act att ggg gtt gat ttt gca aaa agt gcc aga aaa        1080
Ile Asp Gly Lys Thr Ile Gly Val Asp Phe Ala Lys Ser Ala Arg Lys
305                 310                 315 gac ttg gtc ctc tca gat ggt aac cgc gtc agc gcc ttc tct gta gct        1128
Asp Leu Val Leu Ser Asp Gly Asn Arg Val Ser Ala Phe Ser Val Ala
320                 325                 330 agt acg gct att gct gct gct cag tgg tca tcc acc cag tct caa agt        1176
Ser Thr Ala Ile Ala Ala Ala Gln Trp Ser Ser Thr Gln Ser Gln Ser
335                 340                 345                 350 ggt gaa gga ggc agt gtt gac tac agt tat ctg caa cca ggt caa gat        1224
Gly Glu Gly Gly Ser Val Asp Tyr Ser Tyr Leu Gln Pro Gly Gln Asp
                355                 360                 365 ggc tat gcc caa tat gct cag tat tca cag gat tat cag cag ttt tat        1272
Gly Tyr Ala Gln Tyr Ala Gln Tyr Ser Gln Asp Tyr Gln Gln Phe Tyr
        370                 375                 380 caa caa caa gct gga gga ttg gaa tct gat gca tca tct gca tca ggc        1320
Gln Gln Gln Ala Gly Gly Leu Glu Ser Asp Ala Ser Ser Ala Ser Gly
385                 390                 395 aca gca gtg acc acc acc tca gcg gct gta gtg tcc cag agt cct cag        1368
Thr Ala Val Thr Thr Thr Ser Ala Ala Val Val Ser Gln Ser Pro Gln
400                 405                 410 ctg tat aat caa acc tcc aat cca cct ggc tct ccg act gag gaa gca        1416
Leu Tyr Asn Gln Thr Ser Asn Pro Pro Gly Ser Pro Thr Glu Glu Ala
415                 420                 425                 430 cag cct agc act agc aca agt aca cag gcc cca gcc gct tcc cct act        1464
Gln Pro Ser Thr Ser Thr Ser Thr Gln Ala Pro Ala Ala Ser Pro Thr
                435                 440                 445 ggt gta gtt cct ggt acc aaa tat gca gta cct gac acg tcc act tac        1512
Gly Val Val Pro Gly Thr Lys Tyr Ala Val Pro Asp Thr Ser Thr Tyr
        450                 455                 460 cag tat gat gaa tct tca gga tat tac tat gat ccg aca aca ggg ctc        1560
Gln Tyr Asp Glu Ser Ser Gly Tyr Tyr Tyr Asp Pro Thr Thr Gly Leu
465                 470                 475 tat tat gac ccc aac tcg caa tac tac tat aat tcc ttg acc cag cag        1608
Tyr Tyr Asp Pro Asn Ser Gln Tyr Tyr Tyr Asn Ser Leu Thr Gln Gln
480                 485                 490 tac ctt tac tgg gat ggg gaa aaa gag acc tac gtg cca gct gca gag        1656
Tyr Leu Tyr Trp Asp Gly Glu Lys Glu Thr Tyr Val Pro Ala Ala Glu
495                 500                 505                 510 tct agc tcc cac cag cag tcg ggc ctg cct cct gca aaa gag ggg aaa        1704
Ser Ser Ser His Gln Gln Ser Gly Leu Pro Pro Ala Lys Glu Gly Lys
                515                 520                 525 gag aag aag gag aaa ccc aag agc aaa aca gcc cag cag att gcc aaa        1752
Glu Lys Lys Glu Lys Pro Lys Ser Lys Thr Ala Gln Gln Ile Ala Lys
```

```
                      530                 535                 540
gac atg gaa cgc tgg gct aag agt ttg aat aag cag aaa gaa aac ttt     1800
Asp Met Glu Arg Trp Ala Lys Ser Leu Asn Lys Gln Lys Glu Asn Phe
        545                 550                 555 aaa aat agc ttt cag cct gtc aat tcc ttg agg gaa gaa gaa agg aga     1848
Lys Asn Ser Phe Gln Pro Val Asn Ser Leu Arg Glu Glu Glu Arg Arg
560                 565                 570 gaa tct gct gca gca gac gct ggc ttt gct ctc ttt gag aag aag gga     1896
Glu Ser Ala Ala Ala Asp Ala Gly Phe Ala Leu Phe Glu Lys Lys Gly
575                 580                 585                 590 gcc tta gct gaa agg cag cag ctc atc cca gaa ttg gtg cga aat gga     1944
Ala Leu Ala Glu Arg Gln Gln Leu Ile Pro Glu Leu Val Arg Asn Gly
                595                 600                 605 gat gag gag aat ccc ctc aaa agg ggt ctg gtt gct gct tac agt ggt     1992
Asp Glu Glu Asn Pro Leu Lys Arg Gly Leu Val Ala Ala Tyr Ser Gly
            610                 615                 620 gac agt gac aat gag gag gag ctg gtg gag aga ctt gag agt gag gaa     2040
Asp Ser Asp Asn Glu Glu Glu Leu Val Glu Arg Leu Glu Ser Glu Glu
        625                 630                 635 gag aag cta gct gac tgg aag aag atg gcc tgt ctg ctc tgc cgg cgc     2088
Glu Lys Leu Ala Asp Trp Lys Lys Met Ala Cys Leu Leu Cys Arg Arg
    640                 645                 650 cag ttc ccg aac aaa gat gcc cta gtc agg cac cag caa ctc tca gac     2136
Gln Phe Pro Asn Lys Asp Ala Leu Val Arg His Gln Gln Leu Ser Asp
655                 660                 665                 670 ctt cac aag caa aac atg gac atc tac cga cga tcc agg ctg agc gag     2184
Leu His Lys Gln Asn Met Asp Ile Tyr Arg Arg Ser Arg Leu Ser Glu
                675                 680                 685 cag gag ctg gaa gcc ttg gag cta agg gag aga gag atg aaa tac cga     2232
Gln Glu Leu Glu Ala Leu Glu Leu Arg Glu Arg Glu Met Lys Tyr Arg
            690                 695                 700 gac cga gct gca gaa aga cgg gag aag tac ggc att cca gaa cct cca     2280
Asp Arg Ala Ala Glu Arg Arg Glu Lys Tyr Gly Ile Pro Glu Pro Pro
        705                 710                 715 gag ccc aag cgc aag aag cag ttt gat gcc ggc act gtg aat tac gag     2328
Glu Pro Lys Arg Lys Lys Gln Phe Asp Ala Gly Thr Val Asn Tyr Glu
    720                 725                 730 caa ccc acc aaa gat ggc att gac cac agt aac att ggc aac aag atg     2376
Gln Pro Thr Lys Asp Gly Ile Asp His Ser Asn Ile Gly Asn Lys Met
735                 740                 745                 750 ctg cag gcc atg ggc tgg cgg gaa ggc tct ggc ttg gga cga aag tgt     2424
Leu Gln Ala Met Gly Trp Arg Glu Gly Ser Gly Leu Gly Arg Lys Cys
                755                 760                 765 caa ggc att acg gct ccc att gag gct caa gtt cgg cta aag gga gct     2472
Gln Gly Ile Thr Ala Pro Ile Glu Ala Gln Val Arg Leu Lys Gly Ala
            770                 775                 780 ggc cta gga gcc aaa ggc agc gca tat ggt ttg tcg ggc gcc gat tcc     2520
Gly Leu Gly Ala Lys Gly Ser Ala Tyr Gly Leu Ser Gly Ala Asp Ser
        785                 790                 795 tac aaa gat gct gtc cgg aaa gcc atg ttt gcc cgg ttc act gag atg     2568
Tyr Lys Asp Ala Val Arg Lys Ala Met Phe Ala Arg Phe Thr Glu Met
    800                 805                 810 gag t gagagagaga gagagagaga gatgacaagg agcacaagaa gtggtccatc        2622
Glu
815 tcccgaattc gctgttaccg cctgtctctt taagggcatg ccttgtgctg ttaatagatc   2682 ttagggtgaa ccacttcatt ctgcaggttc tccctcccac ccttaaagaa gttcccctta   2742 tgtgggttgc ctggtgaatg ccttccttcc ccgccagagg gcttgtgaac agaccggaga   2802
```

-continued

```
ggacagtgga ttgtttatac tccagtgtac atagtgtaat gtagcgtgtt tacatgtgta      2862
gcctatgttg tggtccatca gcccctcaca ttcctagggg tttgagatgc tgtaggtggt      2922
atgtgacacc aaagccacct ctgtcatttg ttgtgatgtc ttttcttggc aaaagccttg      2982
tgtatatttg tatattacac atttgtacag aattttggaa gattttcagt ctagttgcca      3042
aatctggctc ctttacaaaa gaaatacctt gagaaaaraa aaaaaaaaaa aa              3094
```

<210> SEQ ID NO 4
<211> LENGTH: 815
<212> TYPE: PRT
<213> ORGANISM: Homo sapiens

<400> SEQUENCE: 4

```
Met Gly Ser Asp Lys Arg Val Ser Arg Thr Glu Arg Ser Gly Arg Tyr
 1               5                  10                  15

Gly Ser Ile Ile Asp Arg Asp Asp Arg Asp Glu Arg Glu Ser Arg Ser
            20                  25                  30

Arg Arg Arg Asp Ser Asp Tyr Lys Arg Ser Ser Asp Asp Arg Arg Gly
        35                  40                  45

Asp Arg Tyr Asp Asp Tyr Arg Asp Tyr Asp Ser Pro Gln Arg Glu Arg
    50                  55                  60

Glu Arg Arg Asn Ser Asp Arg Ser Glu Asp Gly Tyr His Ser Asp Gly
65                  70                  75                  80

Asp Tyr Gly Glu His Asp Tyr Arg His Asp Ile Ser Asp Glu Arg Glu
                85                  90                  95

Ser Lys Thr Ile Met Leu Arg Gly Leu Pro Ile Thr Ile Thr Glu Ser
           100                 105                 110

Asp Ile Arg Glu Met Met Glu Ser Phe Glu Gly Pro Gln Pro Ala Asp
       115                 120                 125

Val Arg Leu Met Lys Arg Lys Thr Gly Val Ser Arg Gly Phe Ala Phe
   130                 135                 140

Val Glu Phe Tyr His Leu Gln Asp Ala Thr Ser Trp Met Glu Ala Asn
145                 150                 155                 160

Gln Lys Lys Leu Val Ile Gln Gly Lys His Ile Ala Met His Tyr Ser
                165                 170                 175

Asn Pro Arg Pro Lys Phe Glu Asp Trp Leu Cys Asn Lys Cys Cys Leu
            180                 185                 190

Asn Asn Phe Arg Lys Arg Leu Lys Cys Phe Arg Cys Gly Ala Asp Lys
        195                 200                 205

Phe Asp Ser Glu Gln Glu Val Pro Pro Gly Thr Thr Glu Ser Val Gln
    210                 215                 220

Ser Val Asp Tyr Tyr Cys Asp Thr Ile Ile Leu Arg Asn Ile Ala Pro
225                 230                 235                 240

His Thr Val Val Asp Ser Ile Met Thr Ala Leu Ser Pro Tyr Ala Ser
                245                 250                 255

Leu Ala Val Asn Asn Ile Arg Leu Ile Lys Asp Lys Gln Thr Gln Gln
            260                 265                 270

Asn Arg Gly Phe Ala Phe Val Gln Leu Ser Ser Ala Met Asp Ala Ser
        275                 280                 285

Gln Leu Leu Gln Ile Leu Gln Ser Leu His Pro Pro Leu Lys Ile Asp
    290                 295                 300

Gly Lys Thr Ile Gly Val Asp Phe Ala Lys Ser Ala Arg Lys Asp Leu
305                 310                 315                 320
```

-continued

```
Val Leu Ser Asp Gly Asn Arg Val Ser Ala Phe Ser Val Ala Ser Thr
                325                 330                 335

Ala Ile Ala Ala Ala Gln Trp Ser Ser Thr Gln Ser Gln Ser Gly Glu
            340                 345                 350

Gly Gly Ser Val Asp Tyr Ser Tyr Leu Gln Pro Gly Gln Asp Gly Tyr
        355                 360                 365

Ala Gln Tyr Ala Gln Tyr Ser Gln Asp Tyr Gln Gln Phe Tyr Gln Gln
    370                 375                 380

Gln Ala Gly Gly Leu Glu Ser Asp Ala Ser Ser Ala Ser Gly Thr Ala
385                 390                 395                 400

Val Thr Thr Thr Ser Ala Ala Val Val Ser Gln Ser Pro Gln Leu Tyr
                405                 410                 415

Asn Gln Thr Ser Asn Pro Pro Gly Ser Pro Thr Glu Glu Ala Gln Pro
            420                 425                 430

Ser Thr Ser Thr Ser Thr Gln Ala Pro Ala Ala Ser Pro Thr Gly Val
        435                 440                 445

Val Pro Gly Thr Lys Tyr Ala Val Pro Asp Thr Ser Thr Tyr Gln Tyr
    450                 455                 460

Asp Glu Ser Ser Gly Tyr Tyr Tyr Asp Pro Thr Thr Gly Leu Tyr Tyr
465                 470                 475                 480

Asp Pro Asn Ser Gln Tyr Tyr Tyr Asn Ser Leu Thr Gln Gln Tyr Leu
                485                 490                 495

Tyr Trp Asp Gly Glu Lys Glu Thr Tyr Val Pro Ala Ala Glu Ser Ser
            500                 505                 510

Ser His Gln Gln Ser Gly Leu Pro Pro Ala Lys Glu Gly Lys Glu Lys
        515                 520                 525

Lys Glu Lys Pro Lys Ser Lys Thr Ala Gln Gln Ile Ala Lys Asp Met
530                 535                 540

Glu Arg Trp Ala Lys Ser Leu Asn Lys Gln Lys Glu Asn Phe Lys Asn
545                 550                 555                 560

Ser Phe Gln Pro Val Asn Ser Leu Arg Glu Glu Arg Arg Glu Ser
                565                 570                 575

Ala Ala Ala Asp Ala Gly Phe Ala Leu Phe Glu Lys Lys Gly Ala Leu
            580                 585                 590

Ala Glu Arg Gln Gln Leu Ile Pro Glu Leu Val Arg Asn Gly Asp Glu
        595                 600                 605

Glu Asn Pro Leu Lys Arg Gly Leu Val Ala Ala Tyr Ser Gly Asp Ser
    610                 615                 620

Asp Asn Glu Glu Glu Leu Val Glu Arg Leu Glu Ser Glu Glu Glu Lys
625                 630                 635                 640

Leu Ala Asp Trp Lys Lys Met Ala Cys Leu Leu Cys Arg Arg Gln Phe
                645                 650                 655

Pro Asn Lys Asp Ala Leu Val Arg His Gln Gln Leu Ser Asp Leu His
            660                 665                 670

Lys Gln Asn Met Asp Ile Tyr Arg Arg Ser Arg Leu Ser Glu Gln Glu
        675                 680                 685

Leu Glu Ala Leu Glu Leu Glu Arg Glu Met Lys Tyr Arg Asp Arg
    690                 695                 700

Ala Ala Glu Arg Arg Glu Lys Tyr Gly Ile Pro Glu Pro Pro Glu Pro
705                 710                 715                 720

Lys Arg Lys Lys Gln Phe Asp Ala Gly Thr Val Asn Tyr Glu Gln Pro
                725                 730                 735

Thr Lys Asp Gly Ile Asp His Ser Asn Ile Gly Asn Lys Met Leu Gln
```

```
                740             745             750
Ala Met Gly Trp Arg Glu Gly Ser Gly Leu Gly Arg Lys Cys Gln Gly
            755             760             765

Ile Thr Ala Pro Ile Glu Ala Gln Val Arg Leu Lys Gly Ala Gly Leu
            770             775             780

Gly Ala Lys Gly Ser Ala Tyr Gly Leu Ser Gly Ala Asp Ser Tyr Lys
785             790             795             800

Asp Ala Val Arg Lys Ala Met Phe Ala Arg Phe Thr Glu Met Glu
                805             810             815

<210> SEQ ID NO 5
<211> LENGTH: 66
<212> TYPE: PRT
<213> ORGANISM: Homo Sapiens

<400> SEQUENCE: 5

Glu Glu Ile Leu Asn Ala Phe Arg Thr Pro Asp Gly Met Pro Val Lys
1               5                   10                  15

Asn Leu Gln Leu Lys Glu Tyr Asn Thr Gly Tyr Asp Tyr Gly Tyr Val
            20                  25                  30

Cys Val Glu Phe Ser Leu Leu Glu Asp Ala Ile Gly Cys Met Glu Ala
        35                  40                  45

Asn Gln Gly Thr Leu Met Ile Gln Asp Lys Glu Val Thr Leu Glu Tyr
    50                  55                  60

Val Ser
65

<210> SEQ ID NO 6
<211> LENGTH: 66
<212> TYPE: PRT
<213> ORGANISM: Mus Musculis

<400> SEQUENCE: 6

Ala Glu Ile Arg Gly Gln Leu Gln Ser His Gly Val Gln Ala Arg Glu
1               5                   10                  15

Val Arg Leu Met Arg Asn Lys Ser Ser Gly Gln Ser Arg Gly Phe Ala
            20                  25                  30

Phe Val Glu Phe Ser His Leu Gln Asp Ala Thr Arg Trp Met Glu Ala
        35                  40                  45

Asn Gln His Ser Leu Asn Ile Leu Gly Gln Lys Val Ser Met His Tyr
    50                  55                  60

Ser Asp
65

<210> SEQ ID NO 7
<211> LENGTH: 59
<212> TYPE: PRT
<213> ORGANISM: Drosophila Melangaster

<400> SEQUENCE: 7

Arg Glu Leu Tyr Ala Leu Phe Arg Ala Ile Gly Pro Ile Asn Thr Cys
1               5                   10                  15

Arg Ile Met Arg Asp Tyr Lys Thr Gly Tyr Ser Phe Gly Tyr Ala Phe
            20                  25                  30
```

```
-continued

Val Asp Phe Thr Ser Glu Met Asp Ser Gln Arg Ala Ile Lys Val Leu
        35                  40                  45

Asn Gly Ile Thr Val Arg Asn Lys Arg Leu Lys
    50                  55
```